(12) United States Patent
Park et al.

(10) Patent No.: US 11,332,474 B2
(45) Date of Patent: May 17, 2022

(54) COMPOUND AND ORGANIC LIGHT-EMISSION DEVICE

(71) Applicant: LG Display Co., Ltd., Seoul (KR)

(72) Inventors: Heejun Park, Paju-si (KR); Seonkeun Yoo, Gunpo-si (KR); Sangbeom Kim, Paju-si (KR); Soyoung Jang, Seoul (KR); Jicheol Shin, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 370 days.

(21) Appl. No.: 16/530,234

(22) Filed: Aug. 2, 2019

(65) Prior Publication Data

US 2020/0048273 A1 Feb. 13, 2020

(30) Foreign Application Priority Data

Aug. 7, 2018 (KR) .................. 10-2018-0091834

(51) Int. Cl.
| | | |
|---|---|---|
| *H01L 51/00* | (2006.01) | |
| *C07D 493/04* | (2006.01) | |
| *C07D 497/04* | (2006.01) | |
| *C07D 495/04* | (2006.01) | |
| *H01L 51/50* | (2006.01) | |

(52) U.S. Cl.
CPC ......... *C07D 493/04* (2013.01); *C07D 495/04* (2013.01); *C07D 497/04* (2013.01); *H01L 51/006* (2013.01); *H01L 51/0073* (2013.01); *H01L 51/5016* (2013.01); *H01L 51/5056* (2013.01); *H01L 51/5072* (2013.01)

(58) Field of Classification Search
None
See application file for complete search history.

(56) References Cited

U.S. PATENT DOCUMENTS

| | | | | |
|---|---|---|---|---|
| 2015/0333277 A1* | 11/2015 | Kim | ............... | H05B 33/20 |
| | | | | 257/40 |
| 2018/0123057 A1* | 5/2018 | Yamatani | ............. | C07D 209/80 |
| 2018/0287068 A1* | 10/2018 | Ha | ............ | C09K 11/06 |

FOREIGN PATENT DOCUMENTS

| | | | | |
|---|---|---|---|---|
| CN | 105778891 A | * | 6/2016 | ............ C09K 11/06 |
| KR | 10-2017-0127099 A | | 11/2017 | |
| KR | 10-1857518 B1 | | 5/2018 | |
| WO | WO-2015167223 A1 | * | 11/2015 | ........... C07D 403/04 |

OTHER PUBLICATIONS

Zhang et al. "A series of novel NIR fluorescent dyes: Synthesis, theoretical calculations and fluorescence imaging applications in living cells" Dyes and Pigments 2016, 125, 220-228. (Year: 2016).*

* cited by examiner

*Primary Examiner* — Robert S Loewe
(74) *Attorney, Agent, or Firm* — Polsinelli PC

(57) ABSTRACT

The present invention provides a novel compound of an amine derivative including a spiro compound. The novel compound has excellent hole transport characteristics. Thus, when the novel compound is applied to a hole transport layer, an auxiliary hole transport layer and an electron blocking layer of an organic light-emitting device, the device realizes low driving voltage, high efficiency, high thermal stability and long life-span. Further, when the novel compound is applied as a blue light-emitting material, the device realizes a low driving voltage and high efficiency.

20 Claims, 3 Drawing Sheets

COMPOUND AND ORGANIC LIGHT-EMISSION DEVICE

CROSS-REFERENCE TO RELATED APPLICATION

This application claims priority from Korean Patent Application No. 10-2018-0091834 filed on Aug. 7, 2018, in the Korean Intellectual Property Office, the disclosure of which is incorporated herein by reference in its entirety.

BACKGROUND

Field of the Disclosure

The present disclosure relates to a novel compound and an organic light-emission device including the same.

Description of the Background

An organic light-emission device (OLED) has a superior viewing angle and a contrast ratio compared to a liquid crystal display (LCD) and is lightweight and ultra-thin because no backlight is required unlike the LCD. In this organic light-emission device structure, when a driving voltage is applied to between a cathode and an anode, electrons and holes are injected from the cathode and the anode into a light emission layer, respectively. Thus, excitons are generated in the light-emission layer and fall to a ground state to emit light.

SUMMARY

One purpose of the present disclosure is to provide a novel material that is chemically and thermally stable and has a high hole mobility. Another purpose of the present disclosure is to provide an organic light-emitting device having high efficiency, low power consumption and long life-span by applying the novel material to a hole transport layer, an auxiliary hole transport layer and an electron blocking layer of the organic light-emitting device.

The purposes of the present disclosure are not limited to the above-mentioned purposes. Other purposes and advantages of the present disclosure, not mentioned above, may be understood from the following descriptions and more clearly understood from embodiments of the present disclosure. Further, it will be readily appreciated that the objects and advantages of the present disclosure may be realized by features and combinations thereof as disclosed in the claims.

In a first aspect of the present disclosure, there is provided a novel compound represent by Chemical Formula 1:

[Chemical Formula 1]

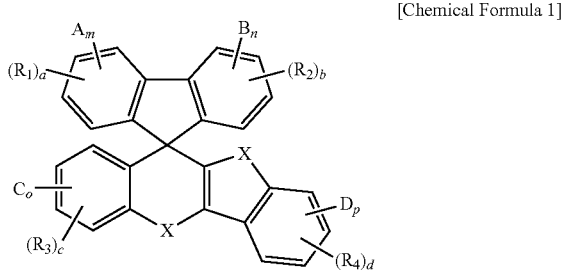

wherein, in the Chemical Formula 1, each of $R_1$ to $R_4$ independently represents one selected from a group consisting of hydrogen, deuterium, halogen, a substituted or unsubstituted C1 to C30 alkyl group, a substituted or unsubstituted C6 to C30 aryl group, a substituted or unsubstituted C2 to C60 heteroaryl group, a substituted or unsubstituted C3 to C30 cycloalkyl group, a C1 to C30 alkoxy group and a C6 to C30 aryloxy group;

wherein each of a and b independently denotes an integer of 0 to 4, wherein when a or b denotes an integer of 2 or greater, a $R_1$s or b $R_2$s are the same or different, wherein each of c and d independently denotes an integer of 0 to 4, wherein when c or d denotes an integer of 2 or greater, c $R_3$s or d $R_4$s are the same or different, wherein each of m and n independently denotes an integer of 0 to 4, wherein when m or n denotes an integer of 2 or greater, m As or n Bs are the same or different, wherein each of o and p independently denotes an integer of 0 to 4, wherein when o or p denotes an integer of 2 or greater, o Cs or p Ds are the same or different, wherein $0 \leq a+m \leq 4$, $0 \leq b+n \leq 4$, $0 \leq c+o \leq 4$ and $0 \leq d+p \leq 4$;

wherein X represents O or S;

wherein each of A to D is represented by Chemical Formula 2:

[Chemical Formula 2]

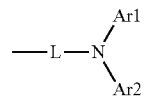

wherein, in the Chemical Formula 2, L represents a direct bond or represents one selected from a group consisting of a substituted or unsubstituted C1 to C10 alkylene group, a substituted or unsubstituted C6 to C30 arylene group or a divalent group of a heteroaromatic ring having 6 to 30 aromatic ring atoms;

wherein each of $Ar_1$ or $Ar_2$ independently represents one selected from a group consisting of a substituted or unsubstituted C6 to C60 aryl group or a monovalent group of a heteroaromatic ring having 6 to 60 aromatic ring atoms, wherein $Ar_1$ and $Ar_2$ are bonded to each other to form a ring.

In a second aspect of the present disclosure, there is provided an organic light-emission device including at least one organic material layer located between an anode and a cathode, wherein the organic material layer contains the novel compound defined above.

The novel compound has excellent hole transport characteristics. Thus, when the novel compound is used in a hole transport layer and an auxiliary hole transport layer of the organic light-emission device, the organic light-emission device may have a low driving voltage and high efficiency. Further, the novel compound has a high LUMO energy level that can block electrons. Thus, when the novel compound is contained in an electron blocking layer of the organic light-emitting device, the organic light-emitting device may have high efficiency.

Further specific effects of the present disclosure as well as the effects as described above will be described in conjunction with illustrations of specific details for carrying out the present disclosure.

DETAILED DESCRIPTIONS

Figure 1:
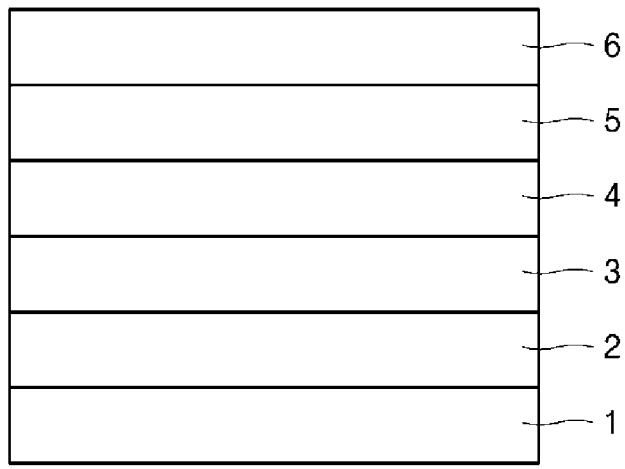
FIG. 1 to FIG. 4 are cross-sectional views schematically illustrating organic light-emission devices according to exemplary embodiments of the present disclosure respectively.

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one implementation of the present disclosure, there is provided a novel compound represent by Chemical Formula 1:

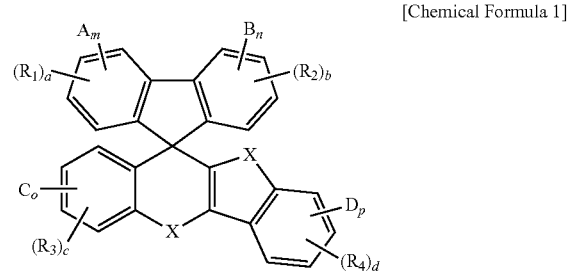

[Chemical Formula 1]

wherein, in the Chemical Formula 1, each of $R_1$ to $R_4$ independently represents one selected from a group consisting of hydrogen, deuterium, halogen, a substituted or unsubstituted C1 to C30 alkyl group, a substituted or unsubstituted C6 to C30 aryl group, a substituted or unsubstituted C2 to C60 heteroaryl group, a substituted or unsubstituted C3 to C30 cycloalkyl group, a C1 to C30 alkoxy group and a C6 to C30 aryloxy group;

each of a and b independently denotes an integer of 0 to 4, wherein when a or b denotes an integer of 2 or greater, each $R_1$ is the same or different and each $R_2$ is the same or different, each of c and d independently denotes an integer of 0 to 4, wherein when c or d denotes an integer of 2 or greater, each $R_3$ is the same or different and each $R_4$ is the same or different, wherein each of m and n independently denotes an integer of 0 to 4, wherein when m or n denotes an integer of 2 or greater, each A is the same or different and each B is the same or different, wherein each of o and p independently denotes an integer of 0 to 4, wherein when o or p denotes an integer of 2 or greater, each C is the same or different and each D is the same or different, wherein $0 \leq a+m \leq 4$, $0 \leq b+n \leq 4$, $0 \leq c+o \leq 4$ and $0 \leq d+p \leq 4$;

X represents O or S;

each of A to D is represented by Chemical Formula 2:

[Chemical Formula 2]

wherein, in the Chemical Formula 2, L represents a direct bond or represents one selected from a group consisting of a substituted or unsubstituted C1 to C10 alkylene group, a substituted or unsubstituted C6 to C30 arylene group or a divalent group of a heteroaromatic ring having 6 to 30 aromatic ring atoms; and each of $Ar_1$ or $Ar_2$ independently represents one selected from a group consisting of a substituted or unsubstituted C6 to C60 aryl group or a monovalent group of a heteroaromatic ring having 6 to 60 aromatic ring atoms, wherein $Ar_1$ and $Ar_2$ are bonded to each other to form a ring.

In one implementation, the compound represented by the Chemical Formula 1 may include a novel compound of an amine derivative including a spiro compound.

The novel compound has excellent hole transport characteristics, thus lowering a driving voltage of the device and thus improving efficiency and power consumption of the device.

In one implementation, the novel compound is chemically and thermally stable and has high hole mobility. Thus, when the novel compound is applied to a hole transport layer, an auxiliary hole transport layer and an electron blocking layer of the organic light-emission device, the organic light-emission device with high efficiency, low power consumption and long life span may be realized.

Further, the novel compound has a high LUMO energy level that can block electrons. Thus, when the compound is applied to an electron blocking layer of the organic light-emitting device, the novel compound may allow the light emission device to have high-efficiency.

In one implementation, the novel compound has a high glass transition temperature. Thus, the novel compound may allow the organic light-emitting device to have increased stability, thereby to realize the organic light-emission device with a long life-span.

In one implementation, when applying the novel compound to a blue light-emitting device, the novel compound may allow the device to have a low driving voltage and high efficiency.

An organic light-emission device emits light via an organic light-emission phenomenon in which electrical energy is converted into light energy in an organic light-emission layer. Materials constituting the organic light-emission device may be classified into a charge injection material used in a hole injection layer and an electron injection layer, a charge transport material used in a hole transport layer, an auxiliary hole transport layer, an electron blocking layer and an electron transport layer, and a light-emission material including a host material and dopants used in a light emission layer.

Examples of the material used for the hole transport layer, the auxiliary hole transport layer, and the electron blocking layer among the charge transport materials may include amine derivatives having carbazole and spiro fluorene frameworks. However, the amine derivatives containing the carbazole framework have low hole mobility, which limits the driving voltage, efficiency and life-span of the light emission device. The amine derivatives containing the spiro fluorene framework have low solubility in organic solvents and thus have difficulty in a solution process. Further, the light-emission material used in the light-emission layer of the organic light-emission device may employ a fluorescent light-emission material having the spiro fluorene framework. However, the fluorescent light-emission material having the spiro fluorene framework has lowered chemical and thermal stability, low efficiency, and short life-span, and thus, may have difficulty in fabricating an organic light-emission device with high efficiency long life span.

Since the novel compound represented by the Chemical Formula 1 has a spiro framework, the compound has high hole mobility. This novel compound may replace the amine derivative containing the carbazole framework and may be applied to the hole transport layer and the auxiliary hole transport layer, thereby increasing the efficiency and lowering the power consumption of the organic light-emission device.

At the same time, the novel compound represented by the Chemical Formula 1 is a spiro compound containing a heteroatom. Thus, the novel compound has a high solubility and is advantageous in a synthesis process and a purification process. The conventional spiro compound is usually problematic in the process because of the low solubility thereof. However, the novel compound represented by the Chemical Formula 1 solves this problem and thus may be used as a fluorescent light-emission material and has advantages in implementing the low driving voltage and high efficiency device.

In one implementation, each of Ar1 and Ar2 in Chemical Formula 2 may be selected from following substituents:

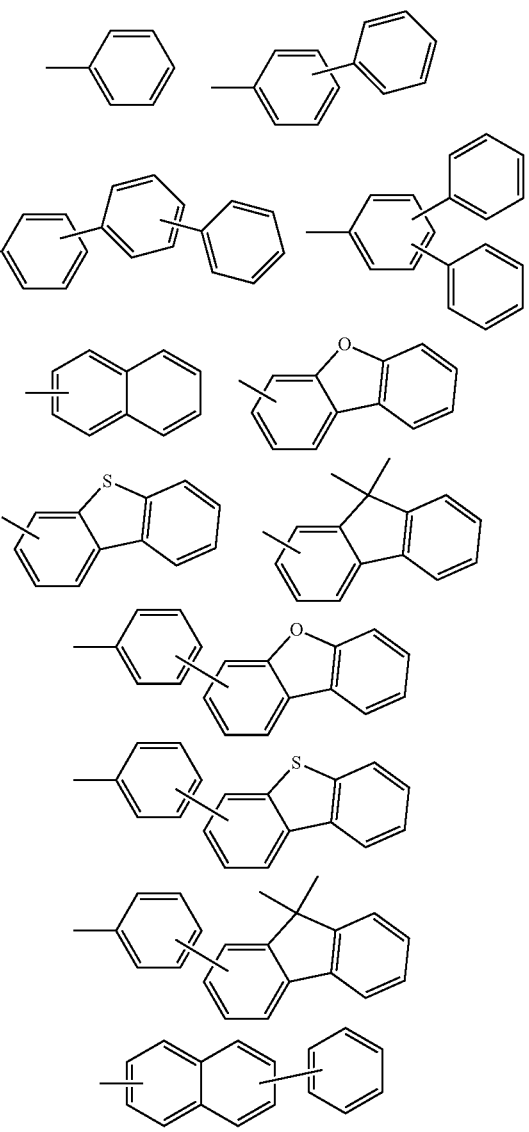

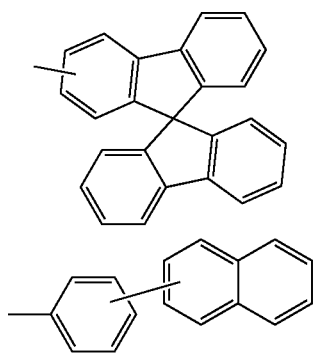
The compound represented by the Chemical Formula 1 may be represented by one of Chemical Formulas 1 to 176. Hereinafter, as used herein, the compound represented by the Chemical Formula 1 is denoted as "a compound 1", while a compound represented by the Chemical Formula 2 is denoted as "a compound 2".
1
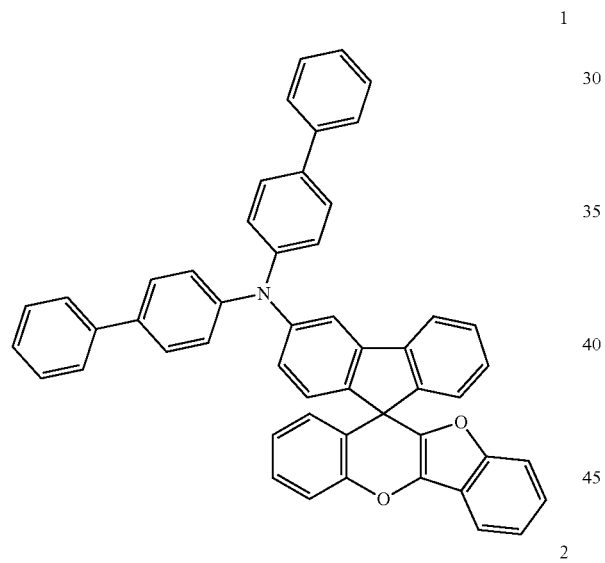
2
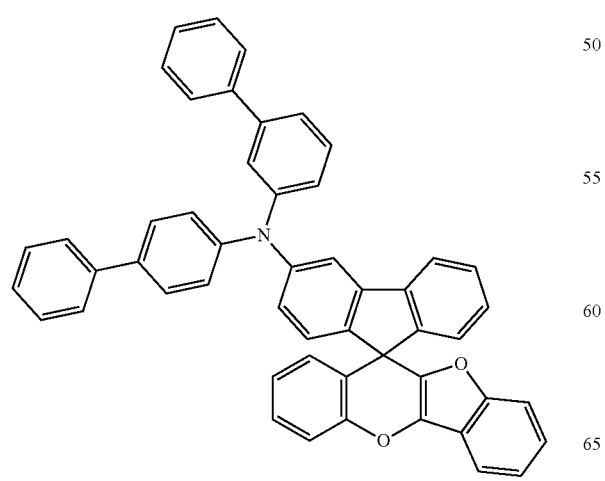
5
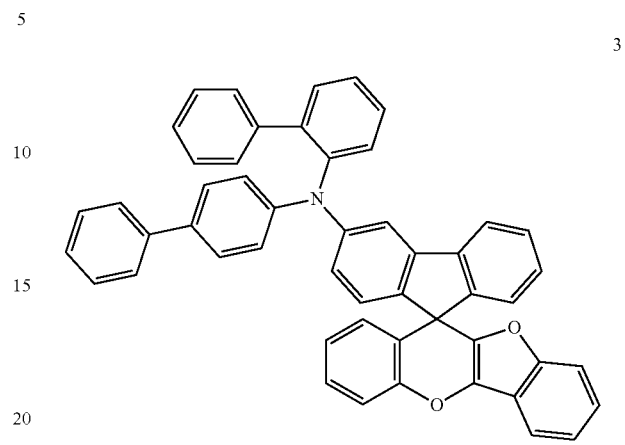
4
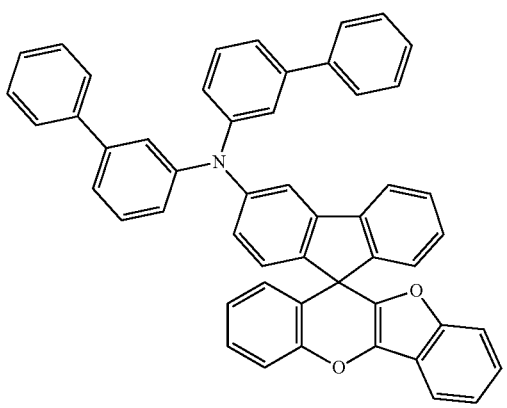
5
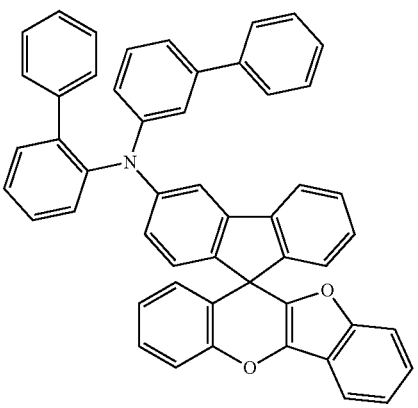

6
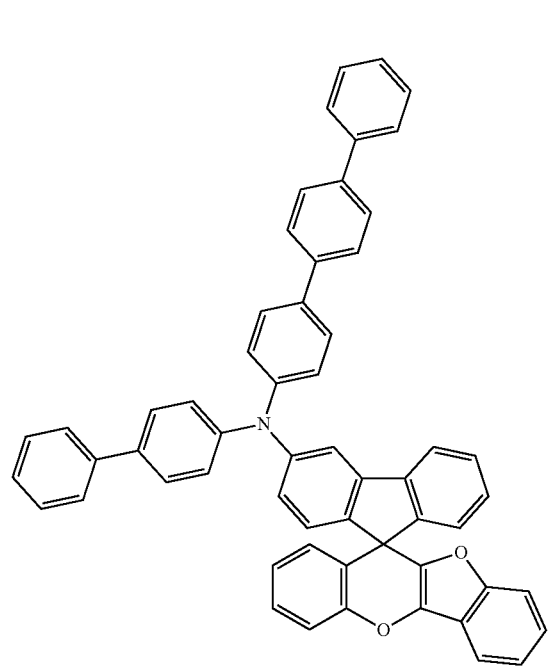
7
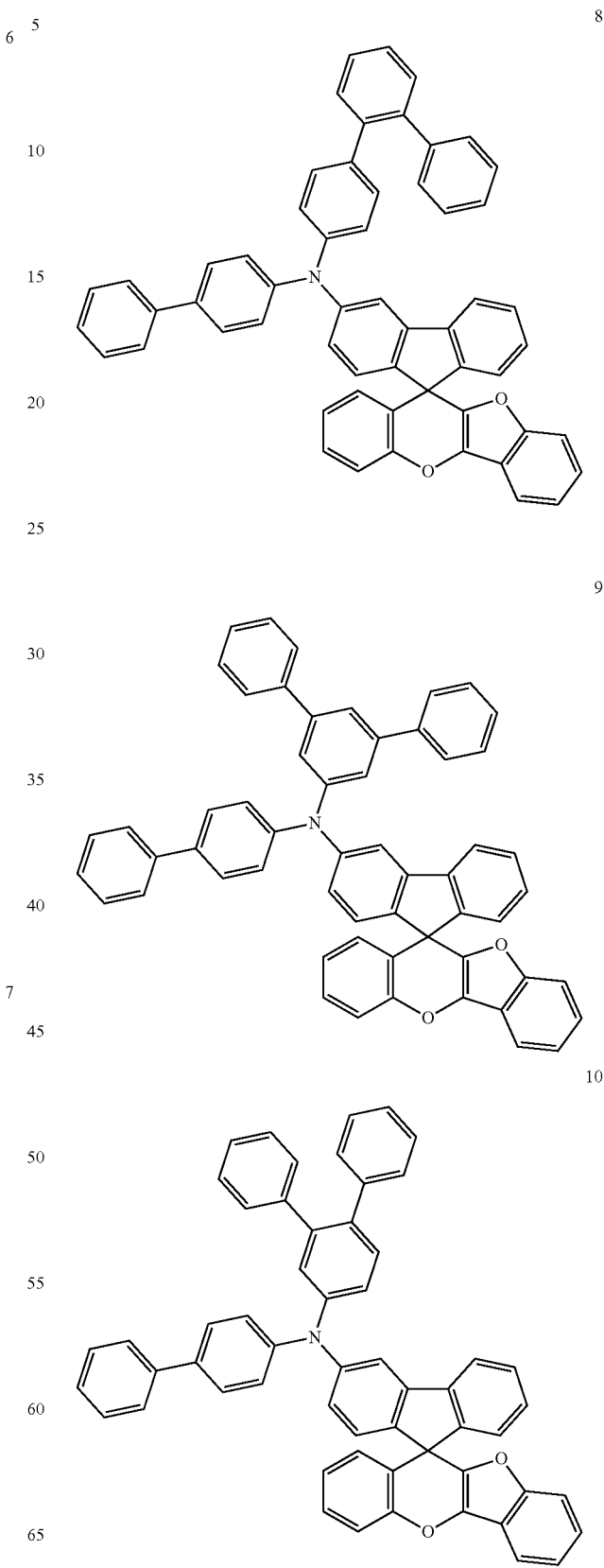

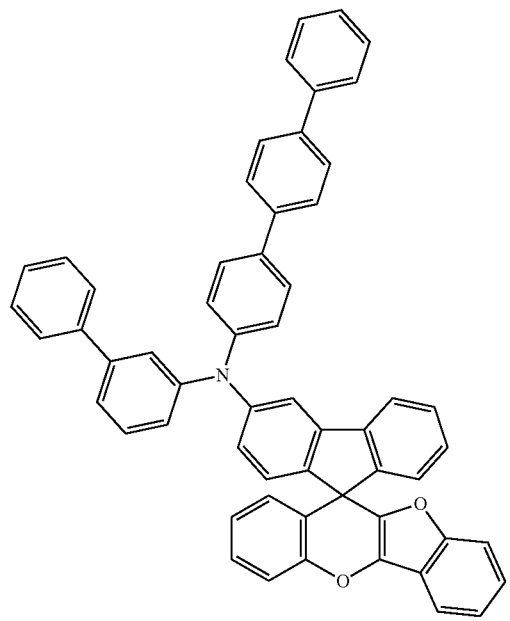
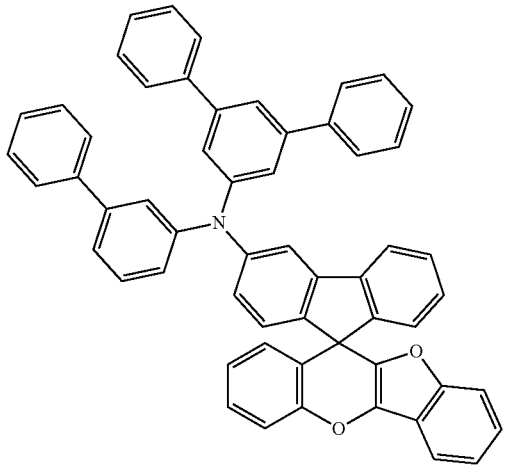
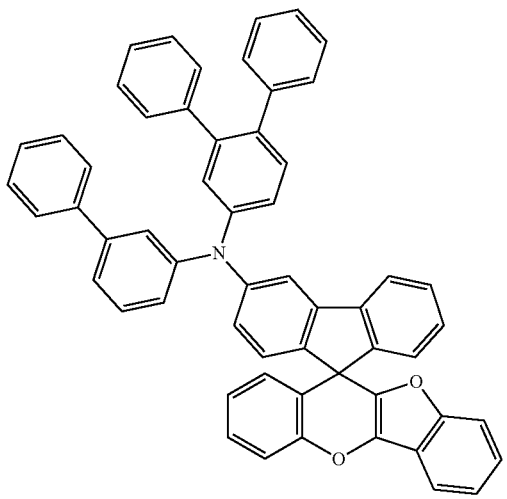
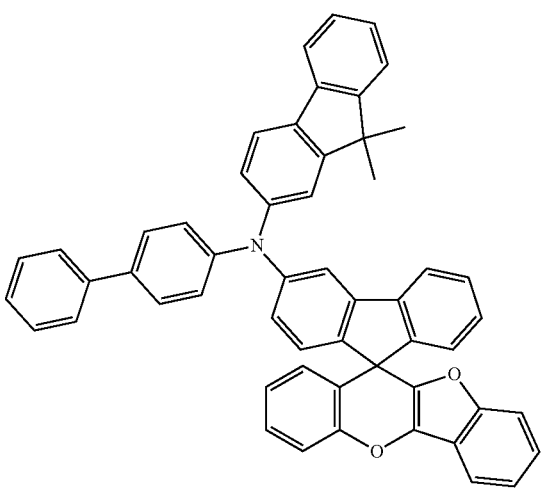

17
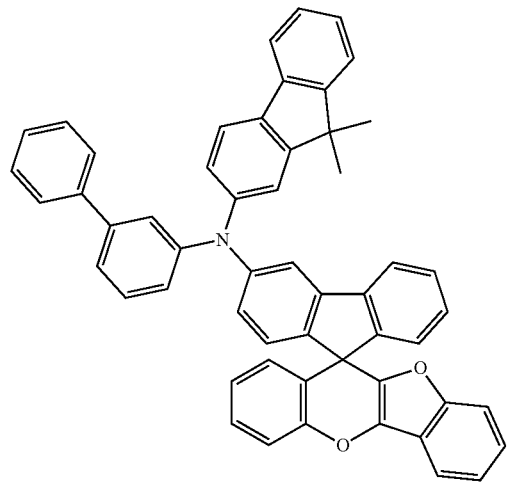
18
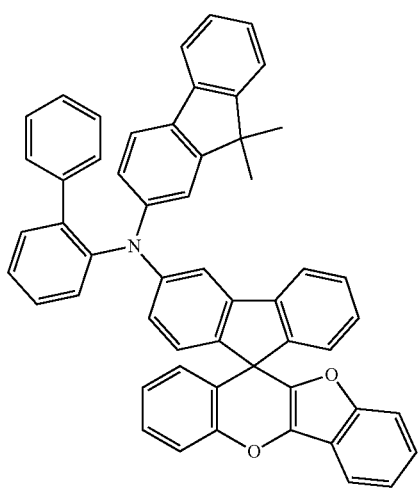
19
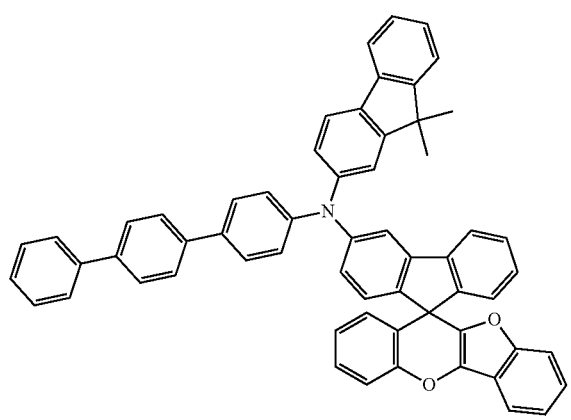
20
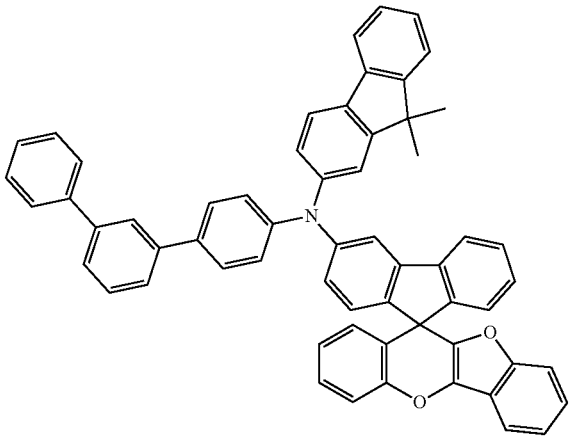
21
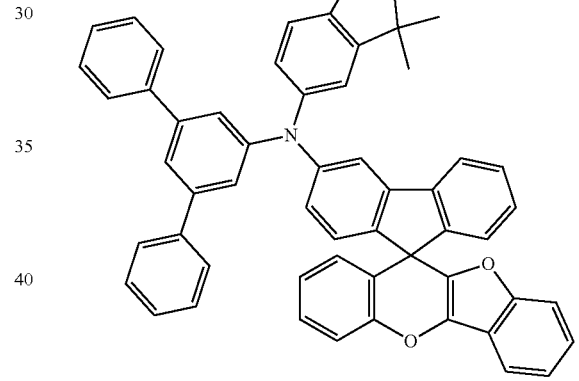
22
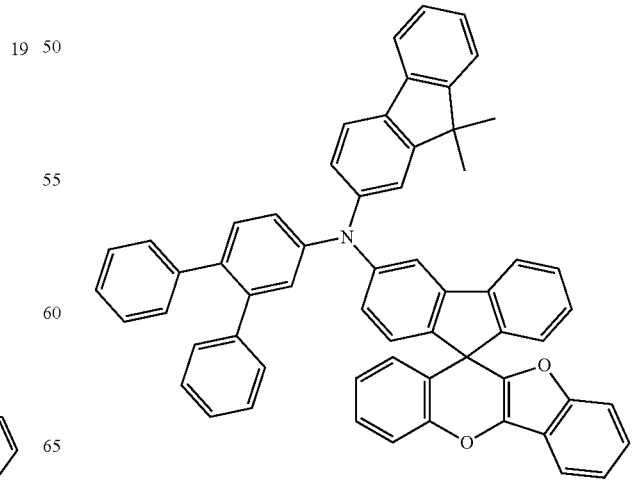

23
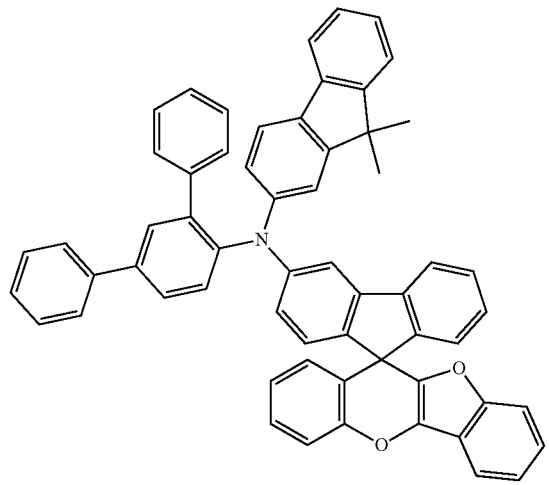
24
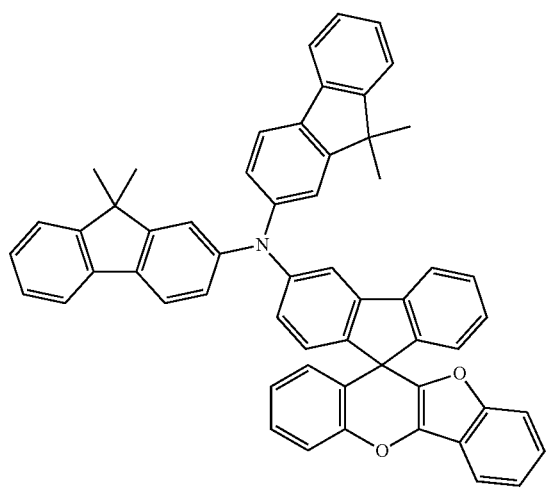
25
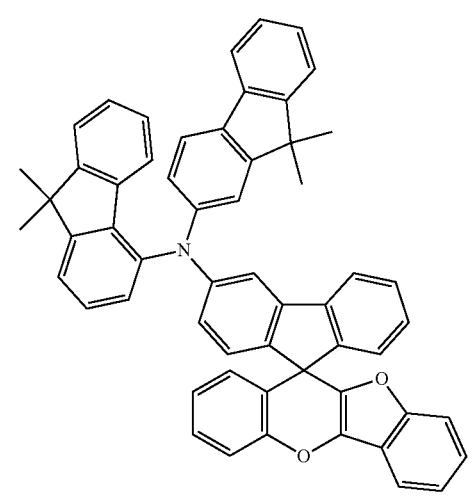
26
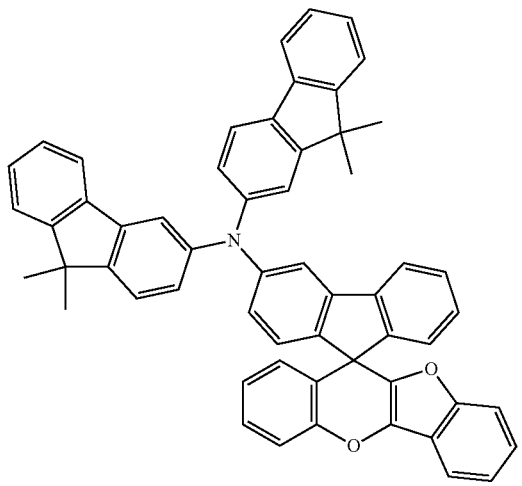
27
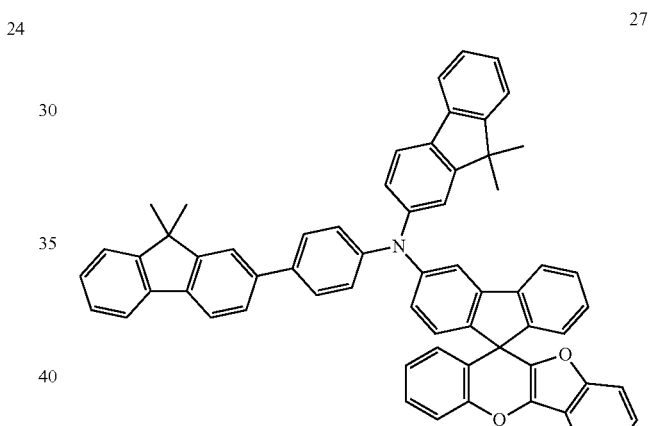
28
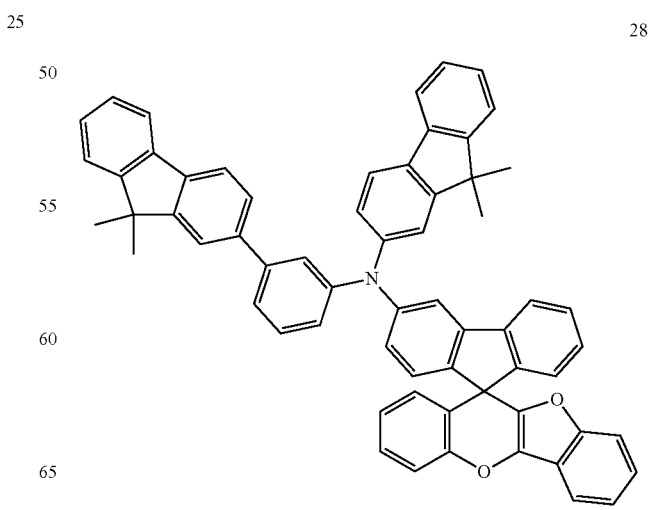

29
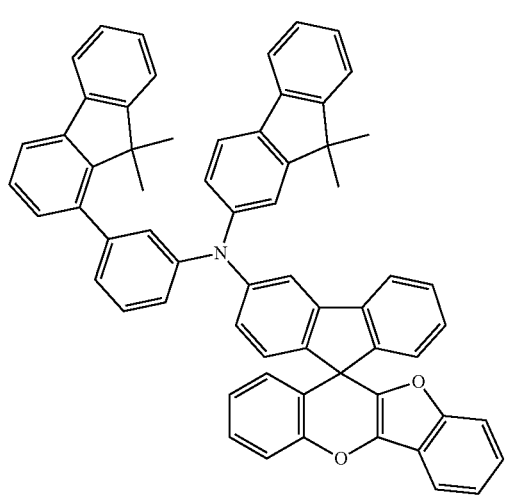
30
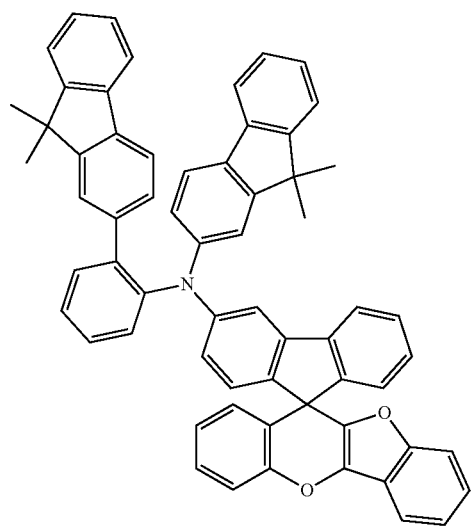
31
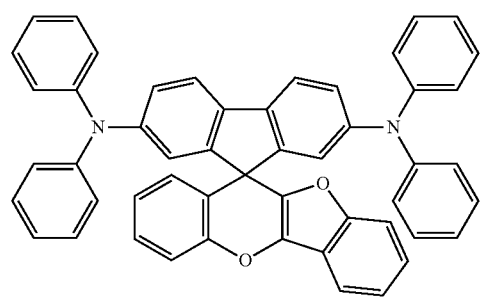
32
33
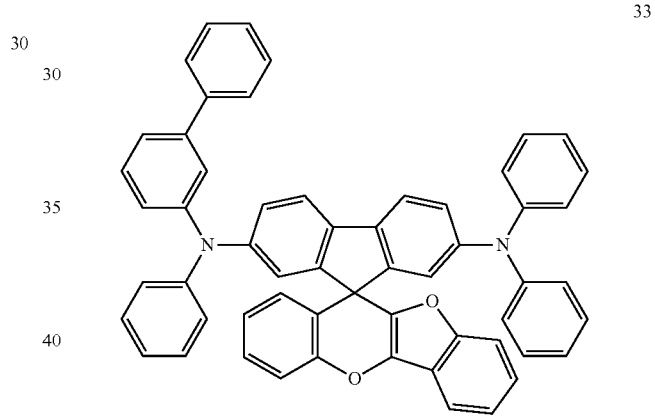
34
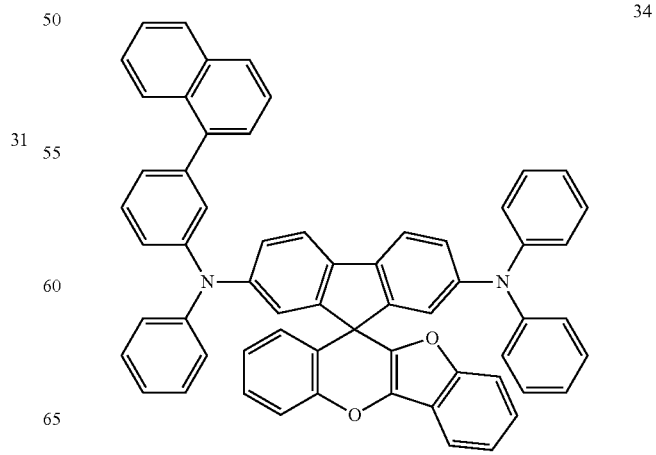

35
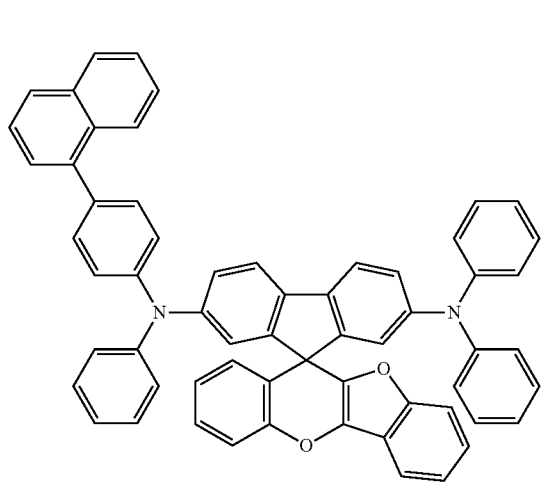
36
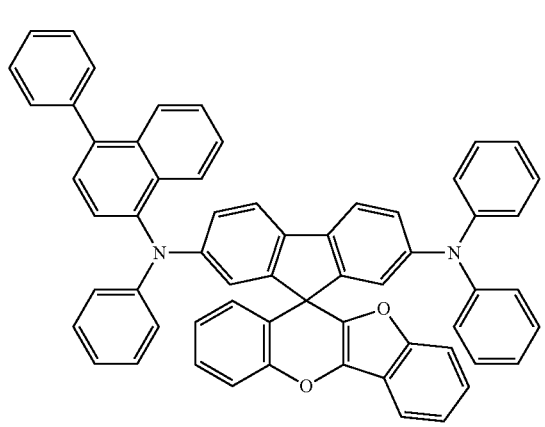
37
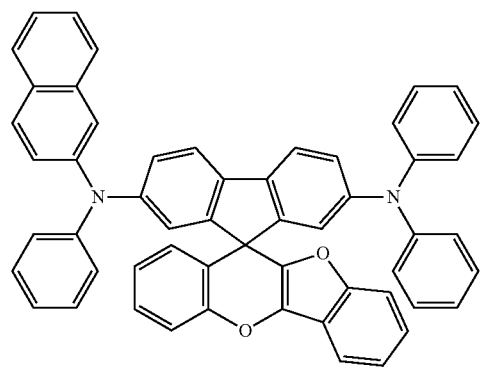
38
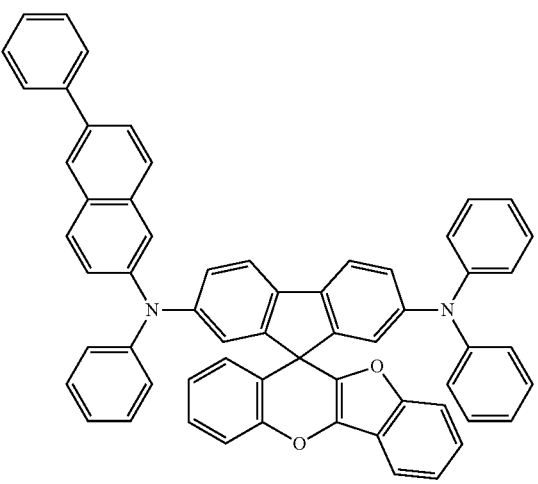
39
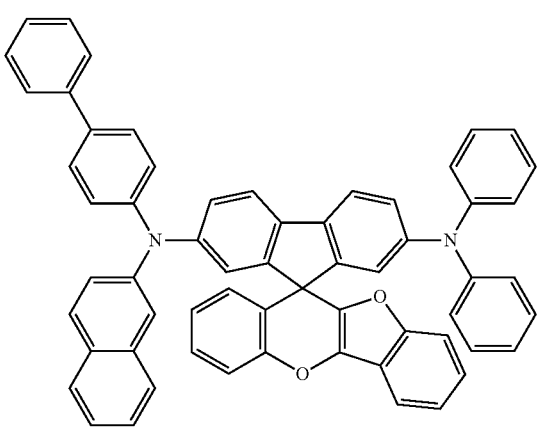
40
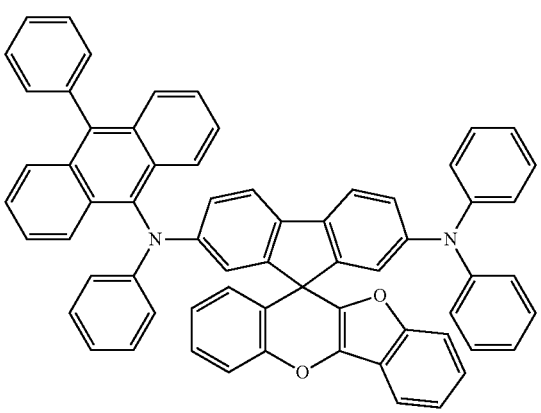

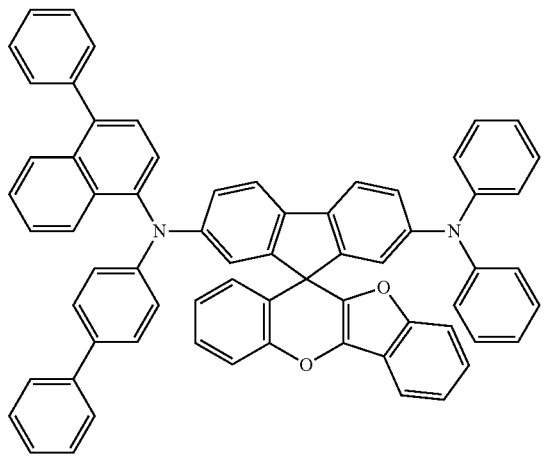
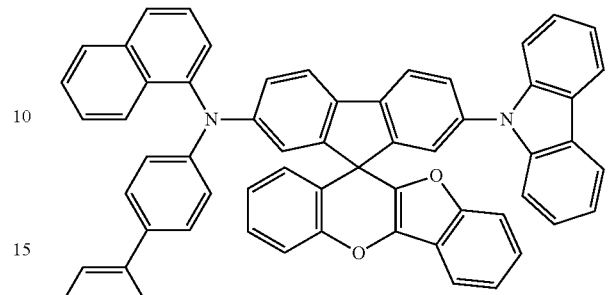
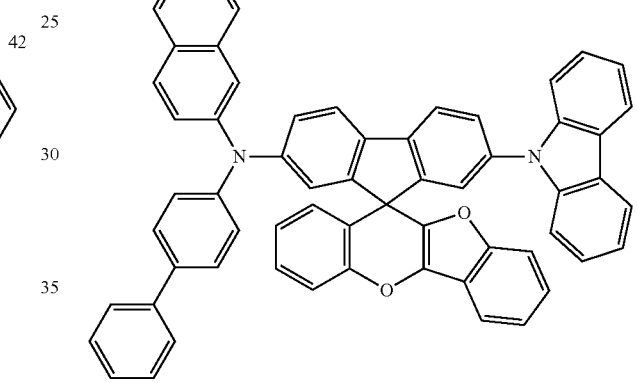
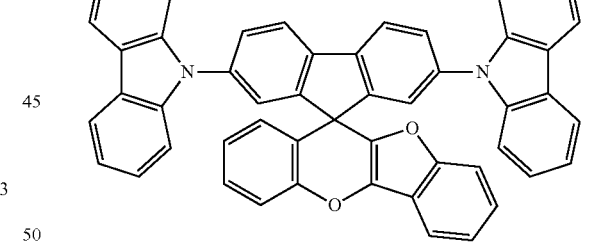
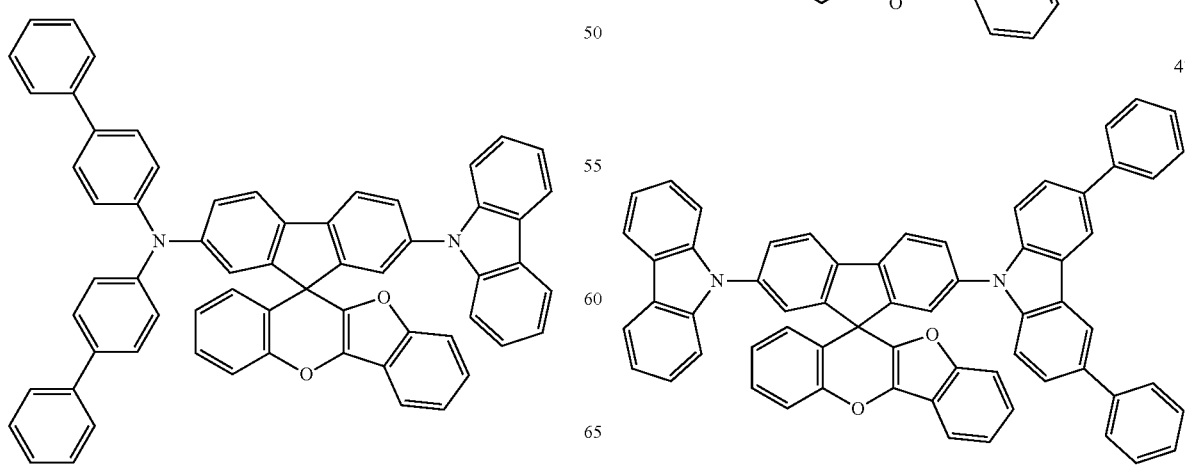

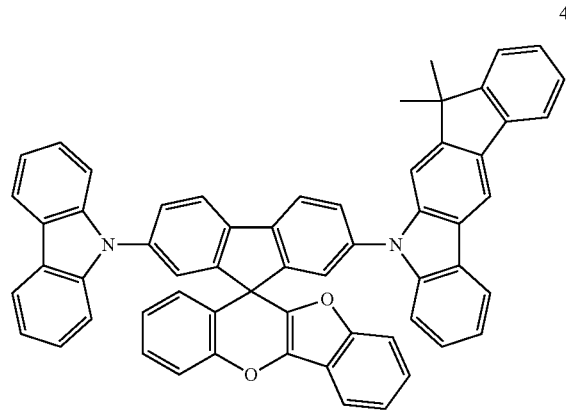
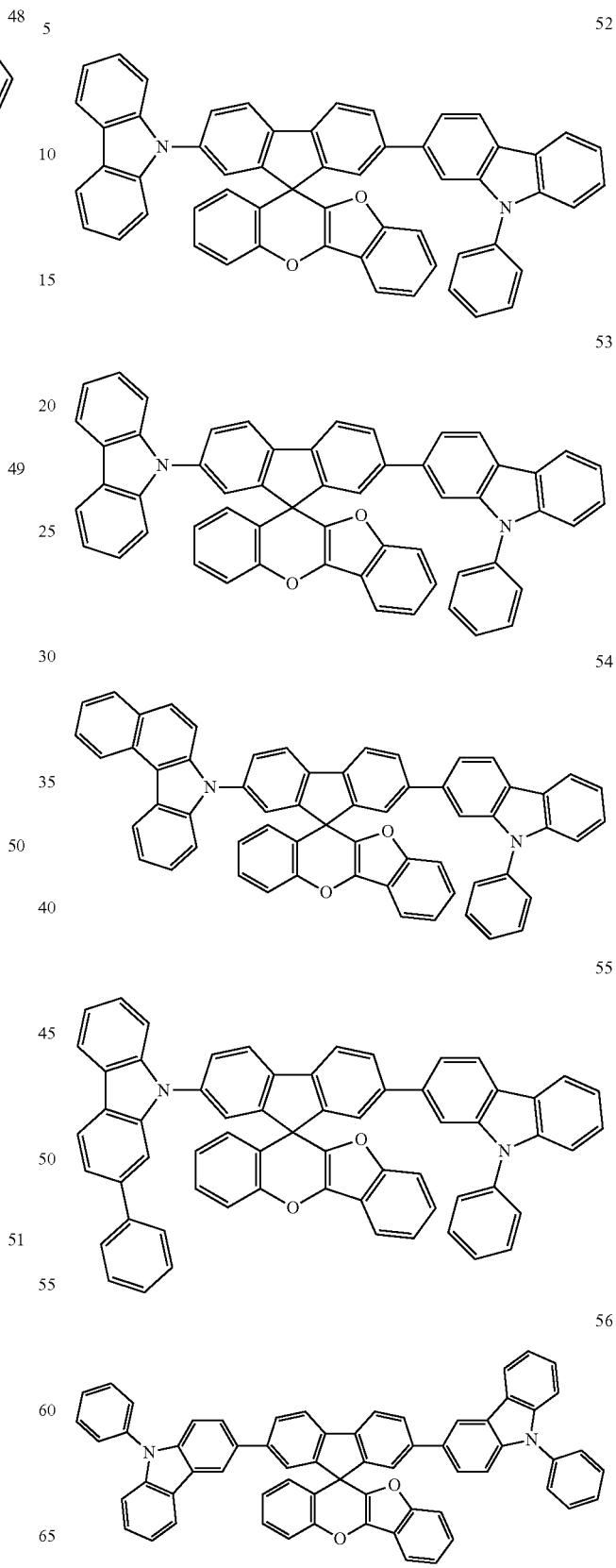

57
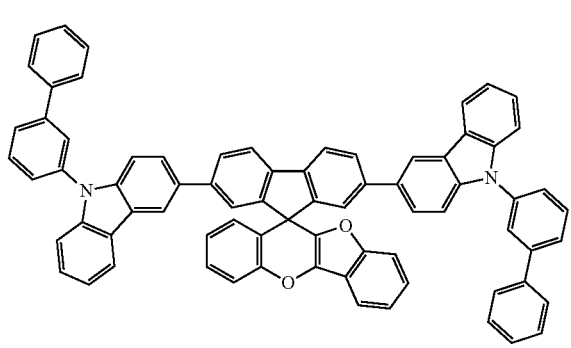
58
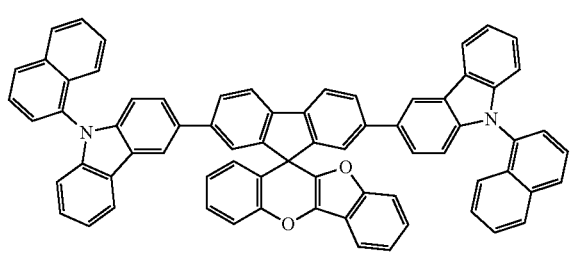
59
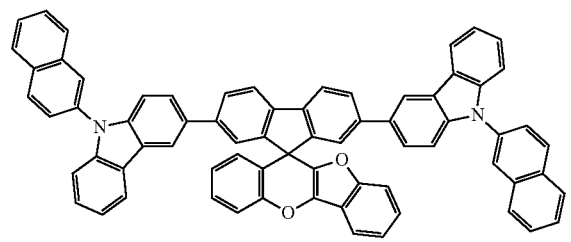
60
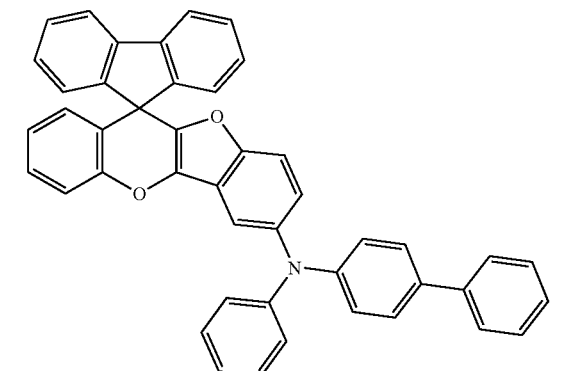
61
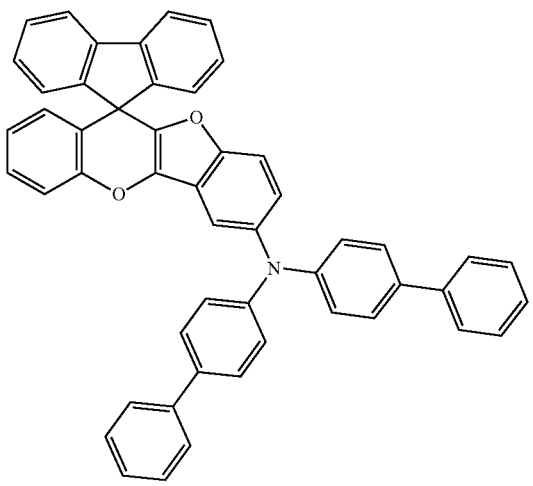
62
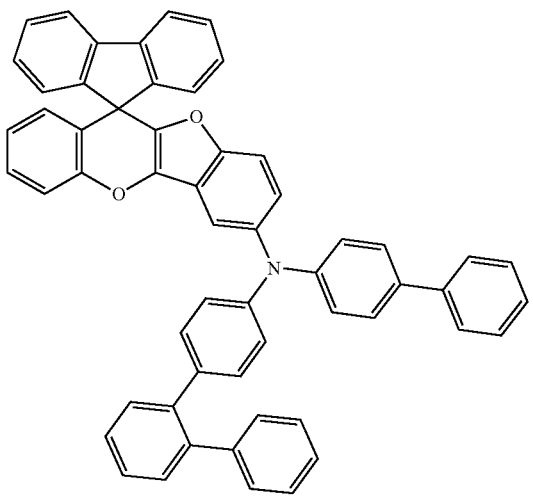
63
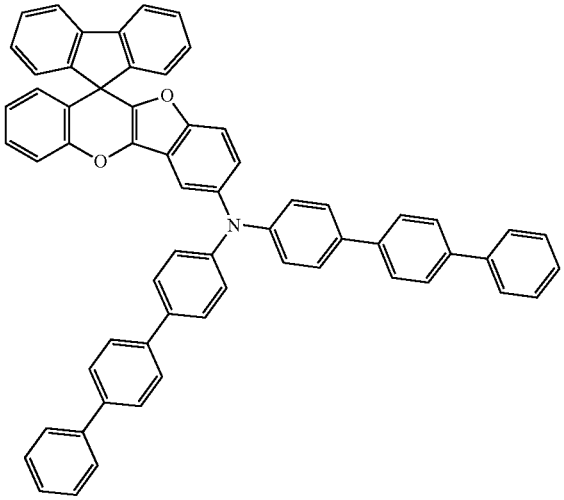

64
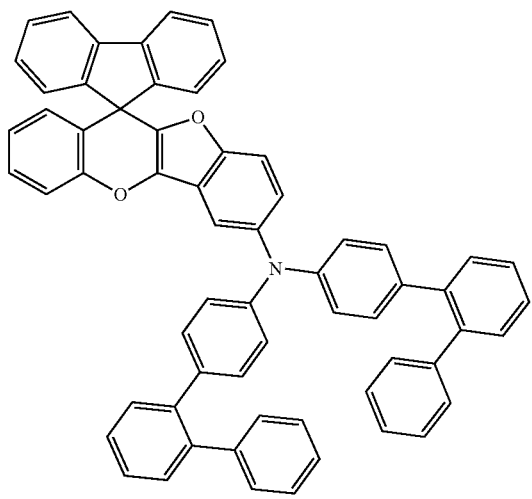
65
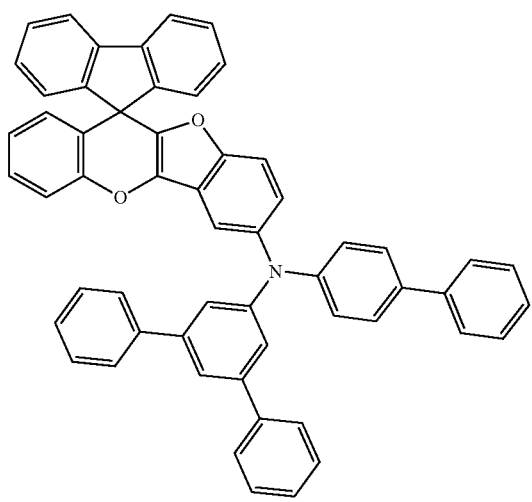
66
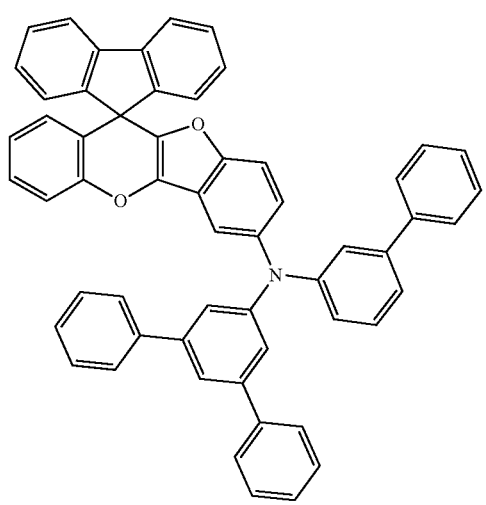
67
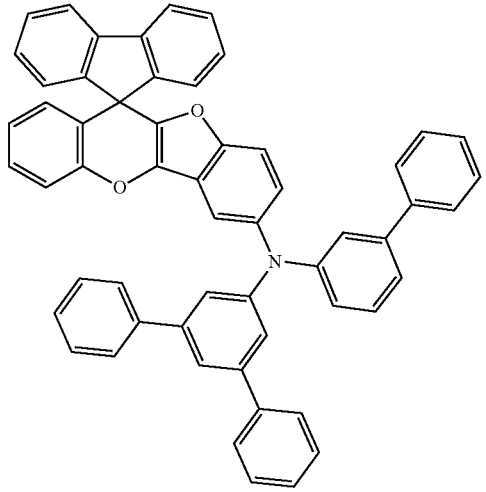
68
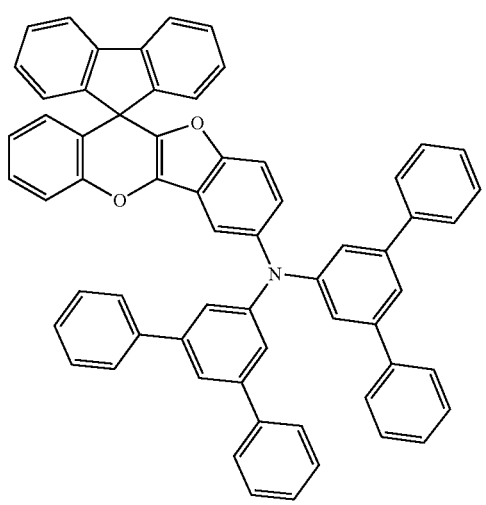
69
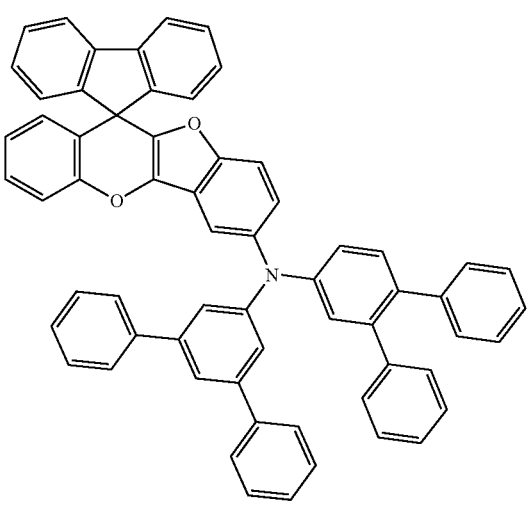

70
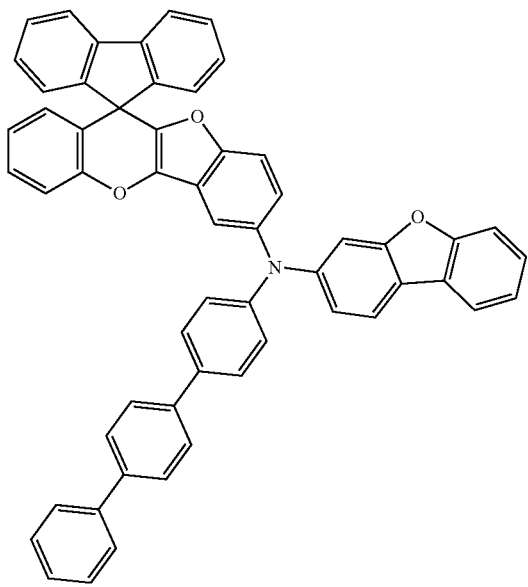
71
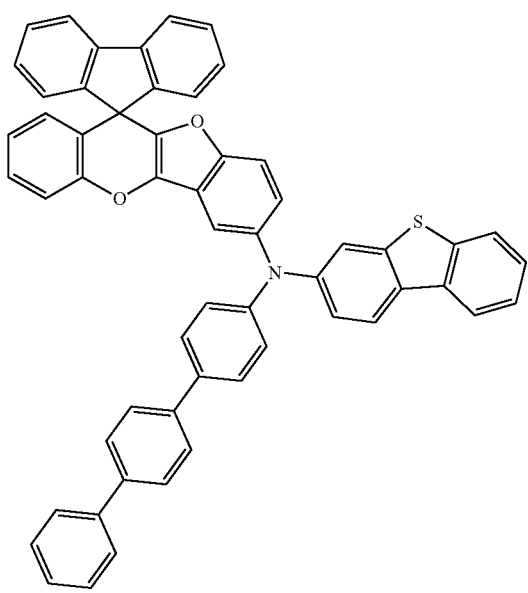
72
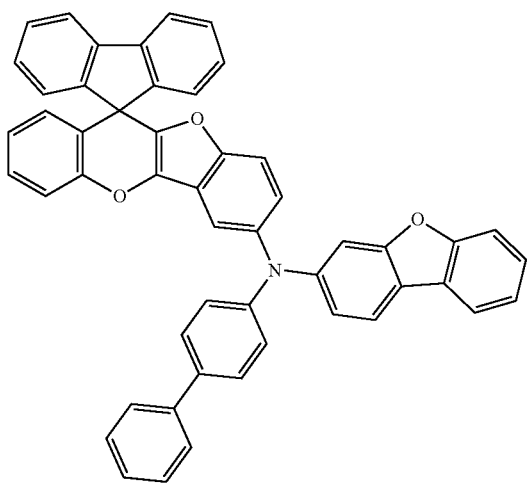
73
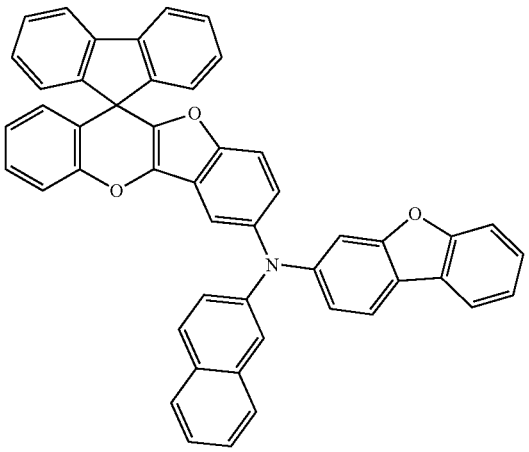
74
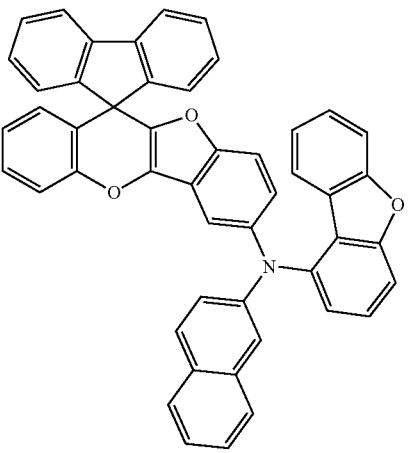
75
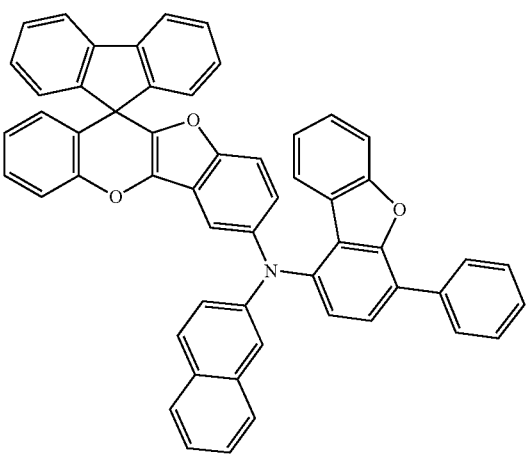

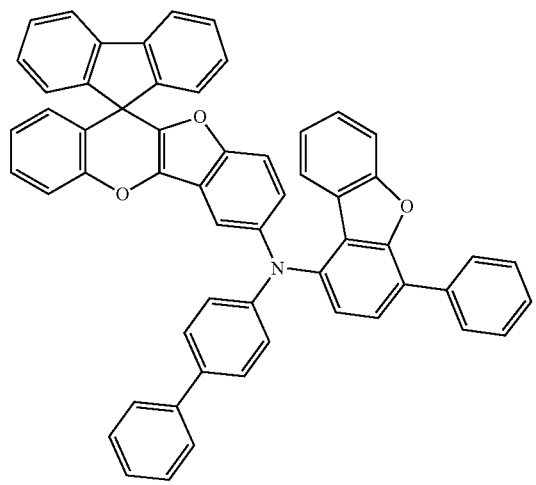
76
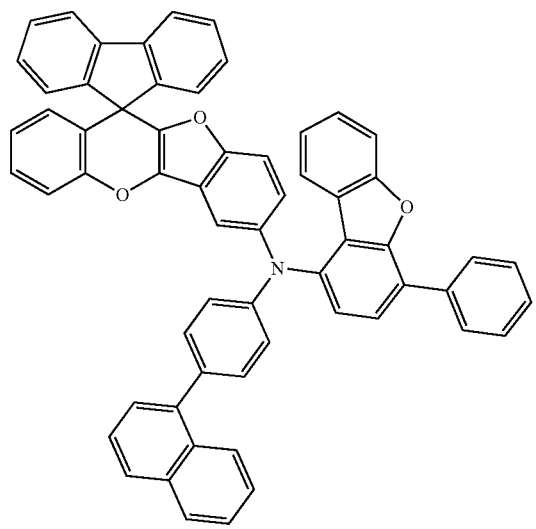
77
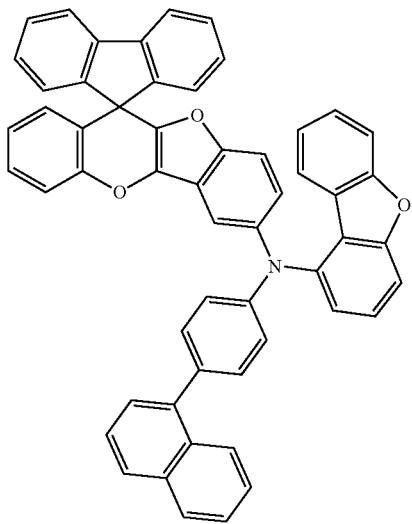
78
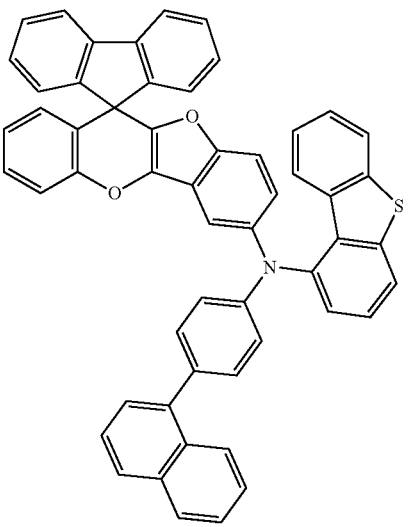
79
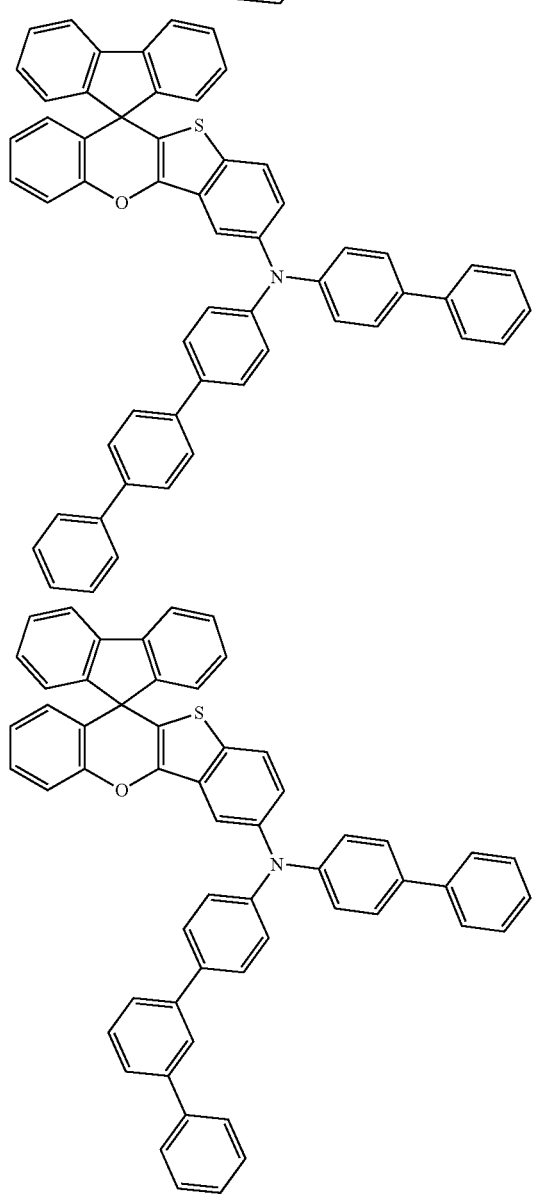

82
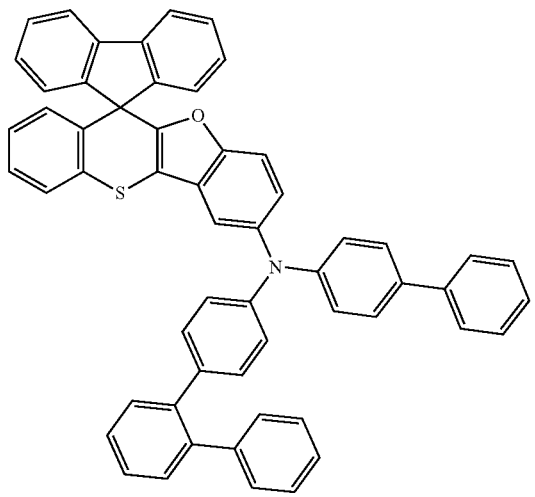
83
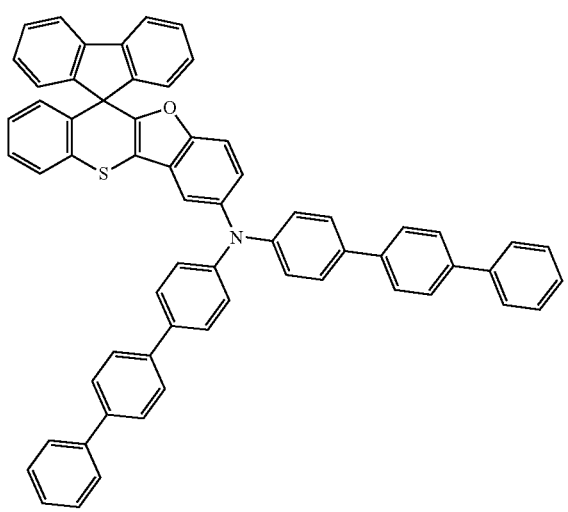
84
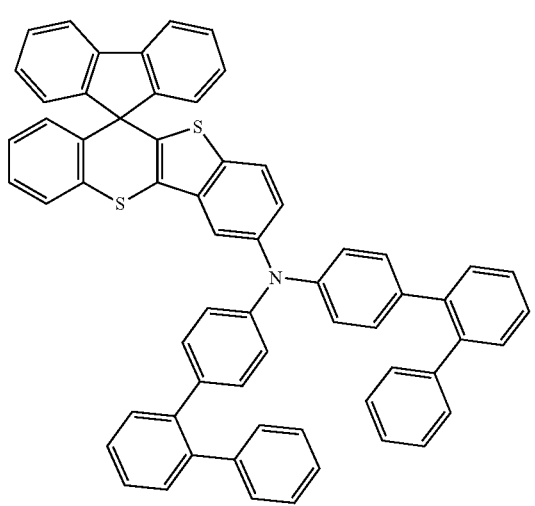
85
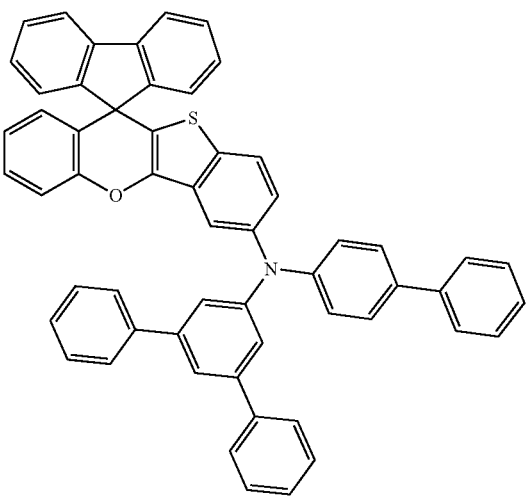
86
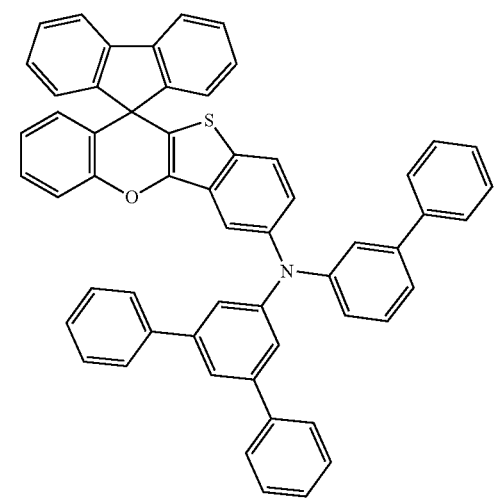
87
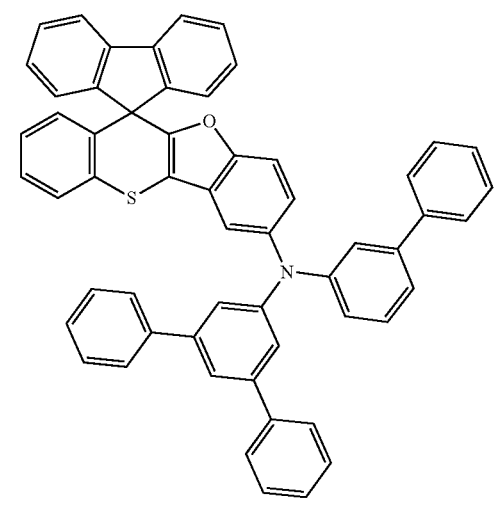

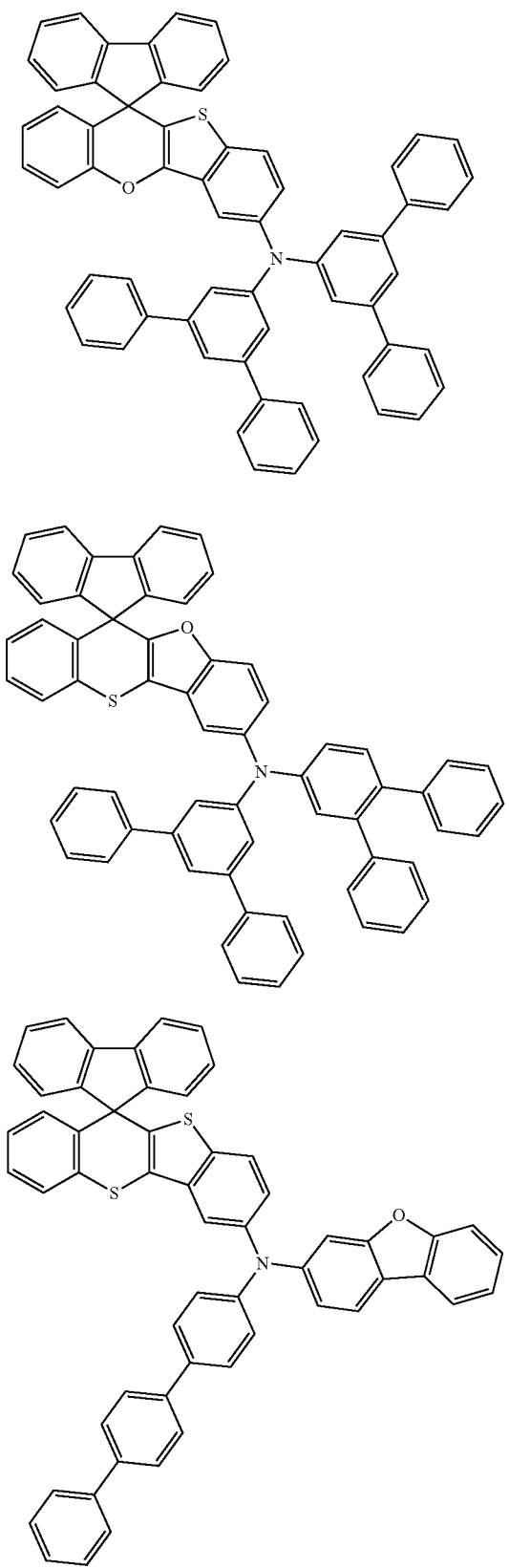
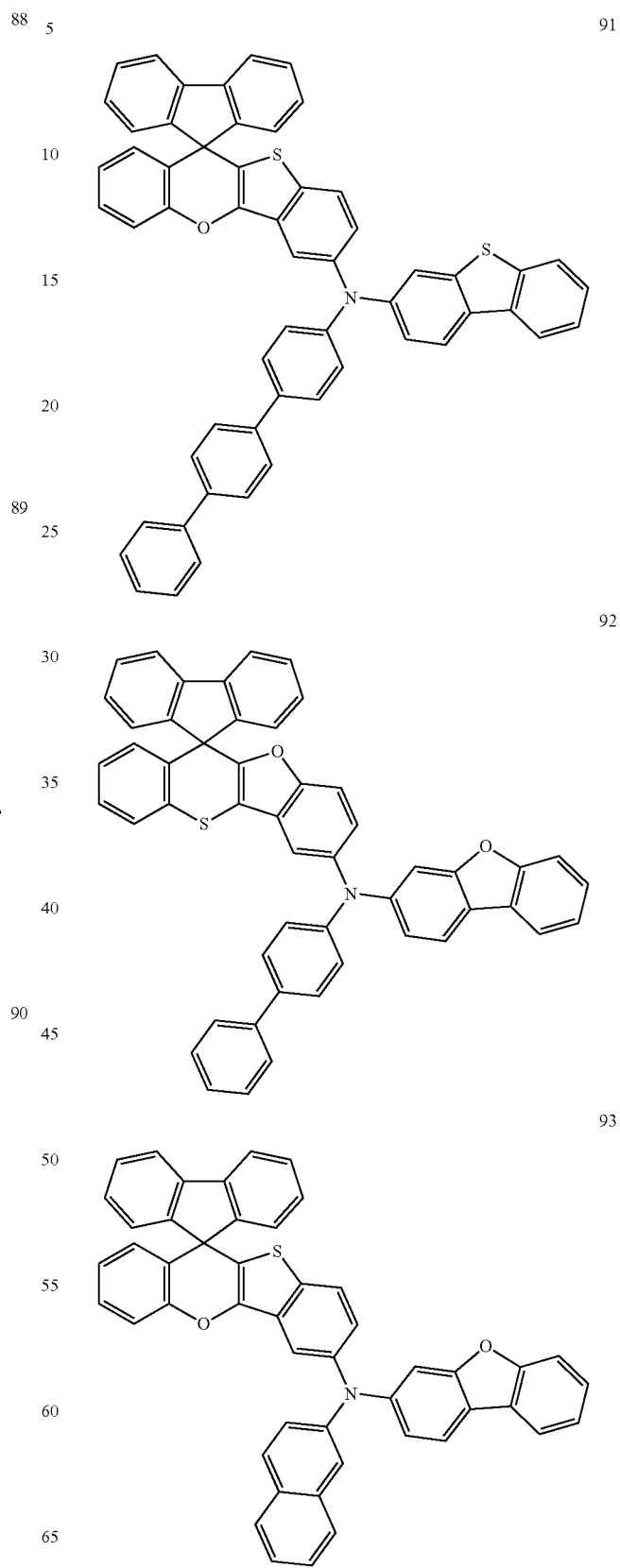

94
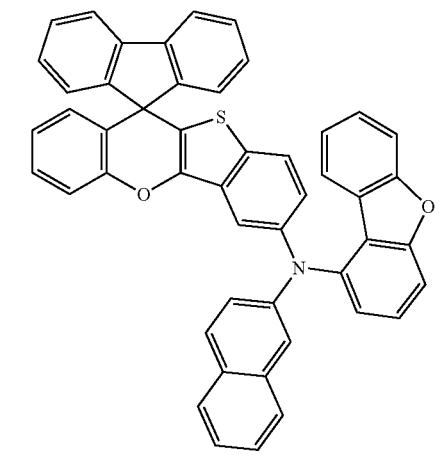
95
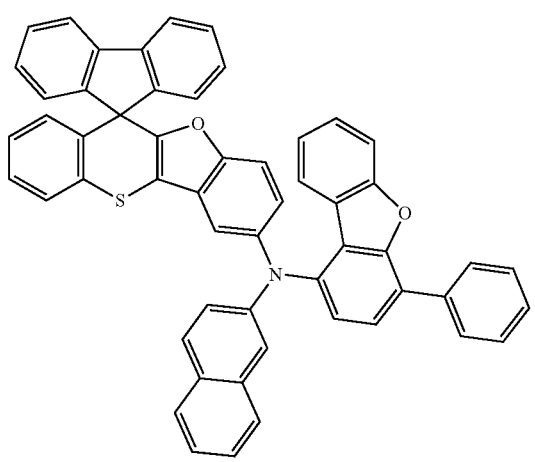
96
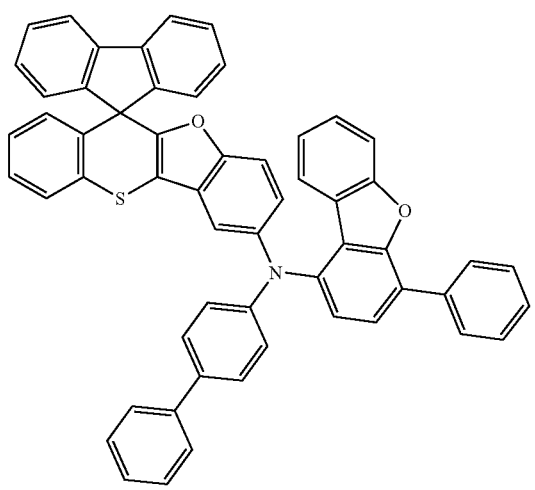
97
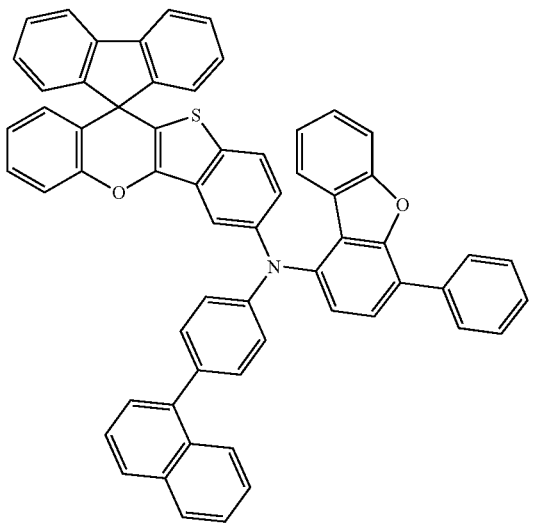
98
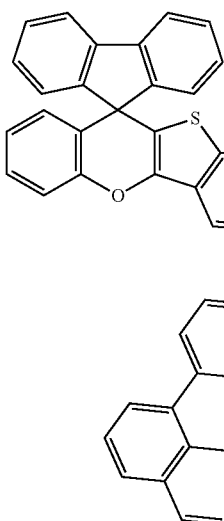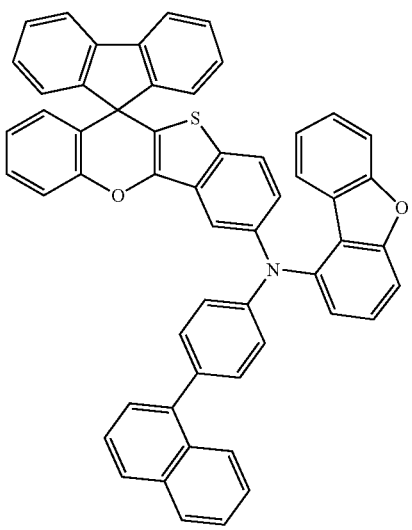
99
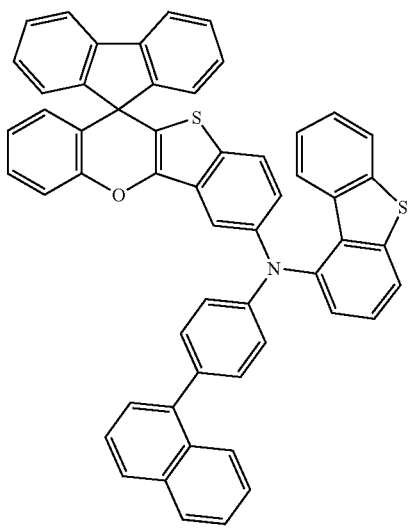

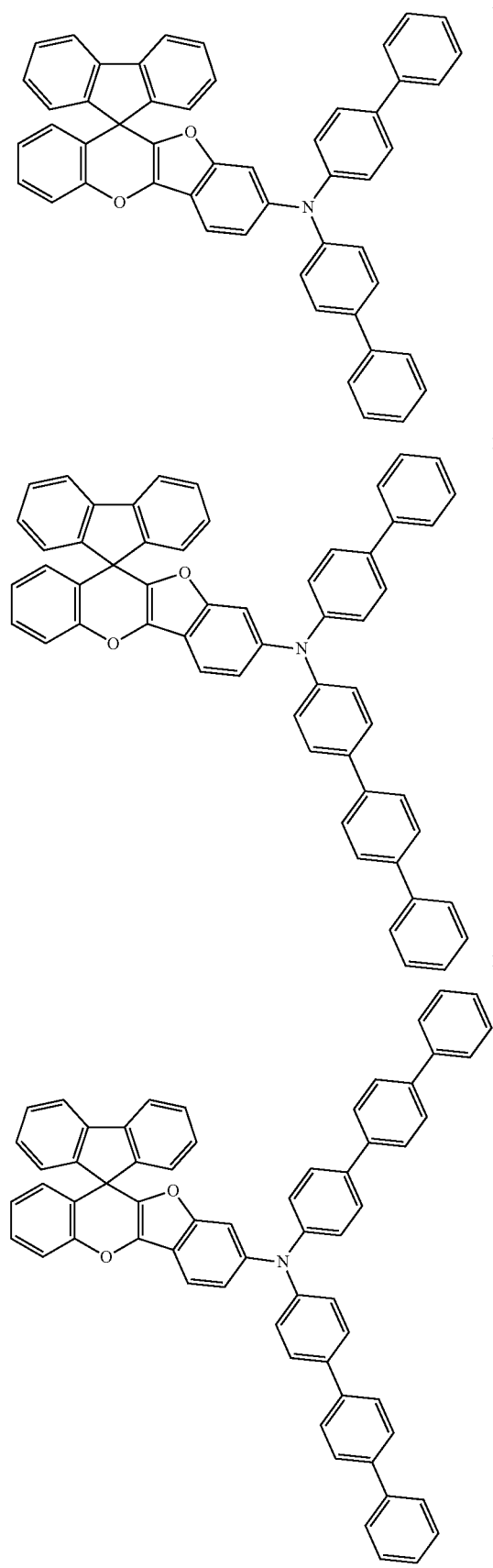
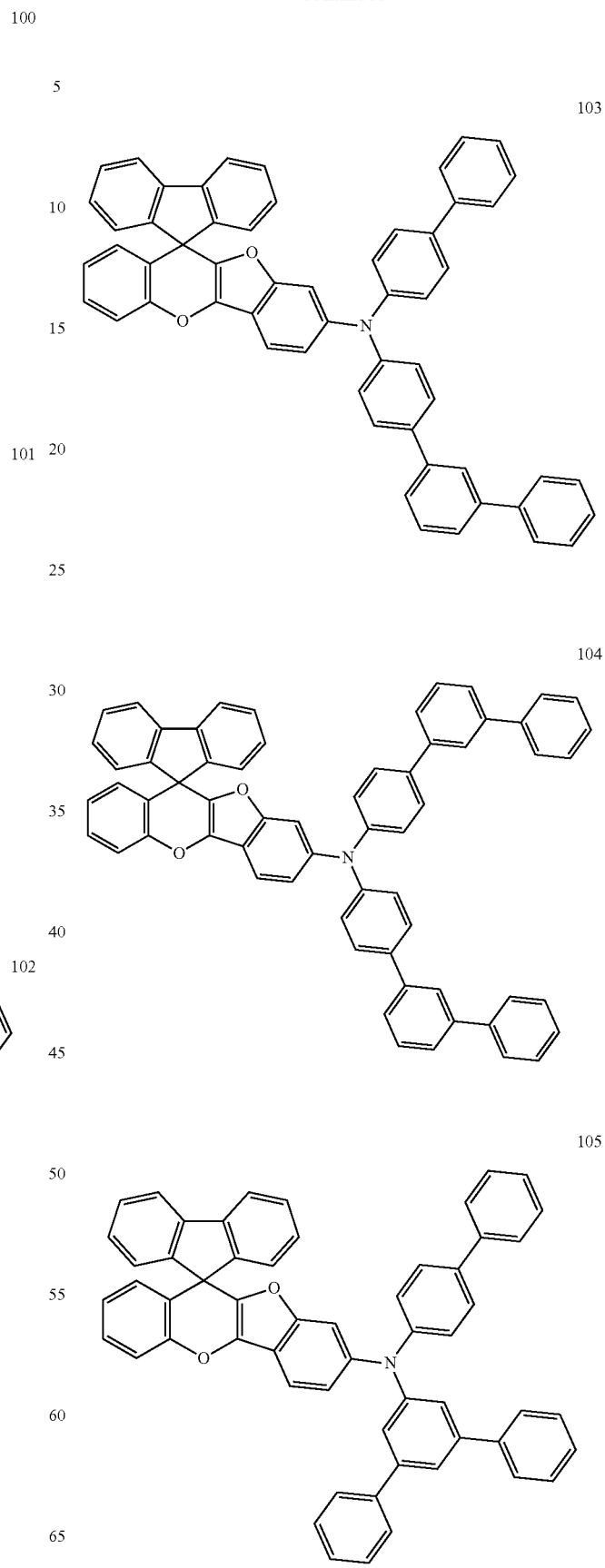

106
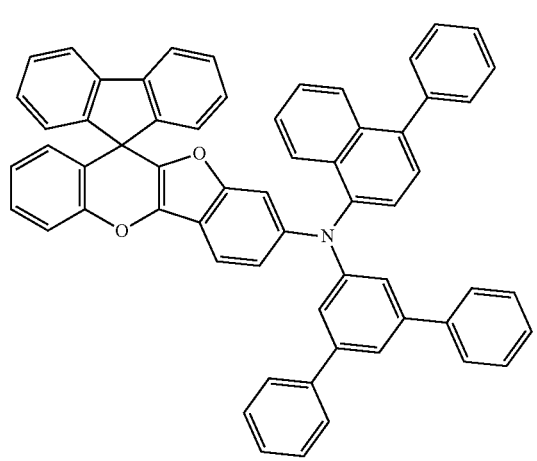
107
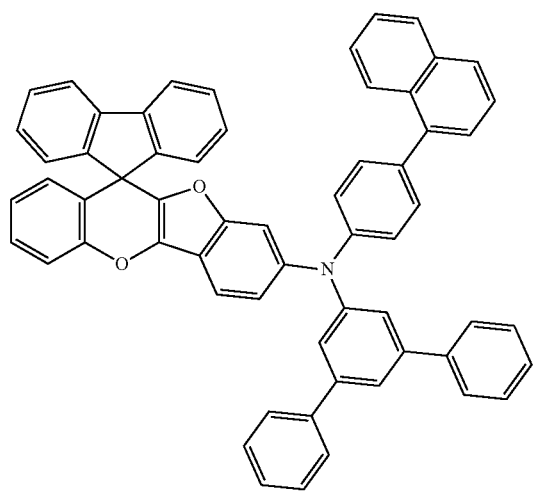
108
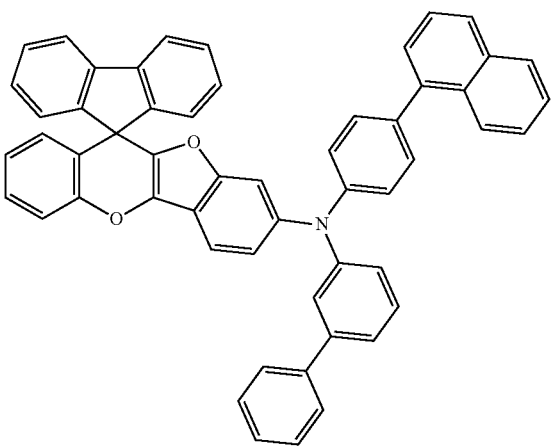
109
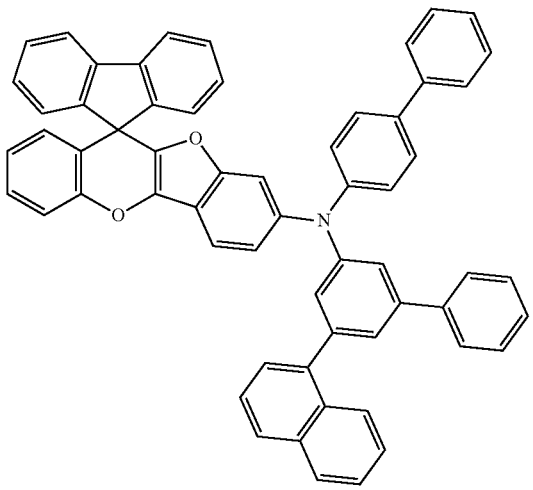
110
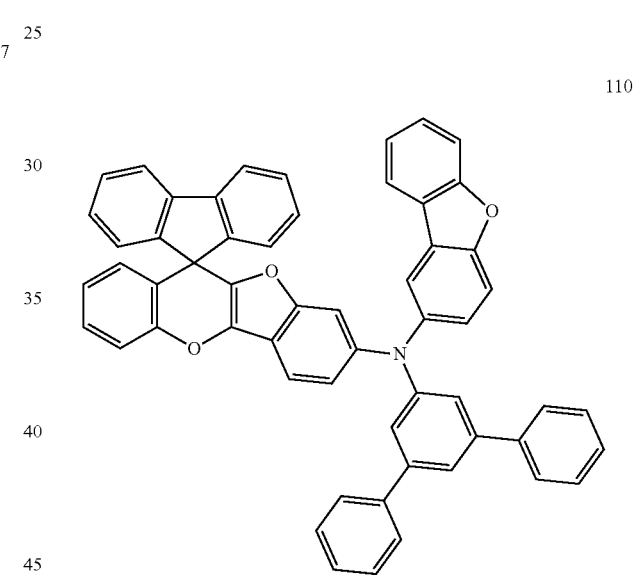
111
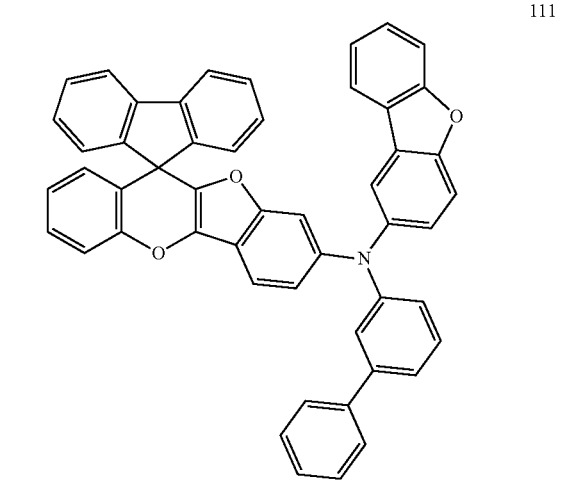

112
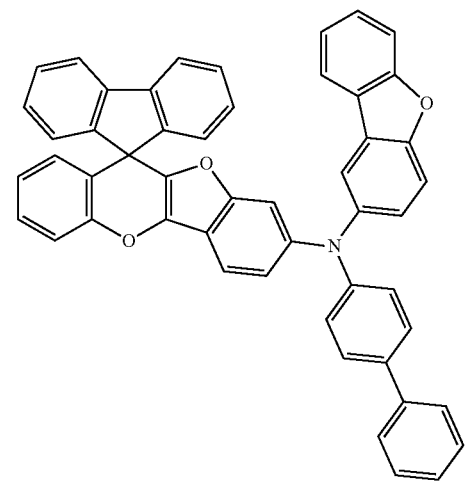
113
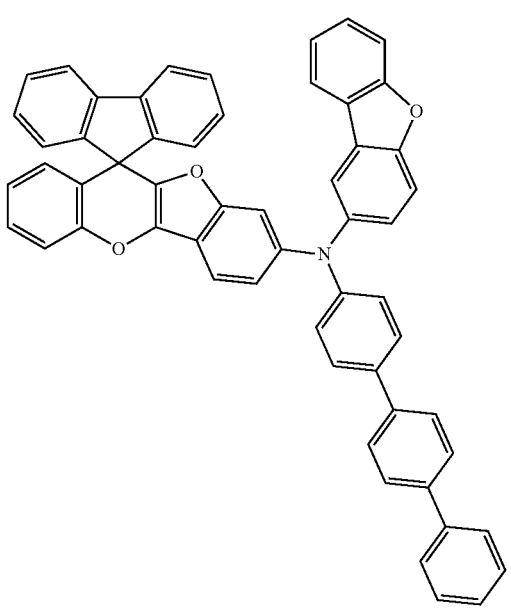
114
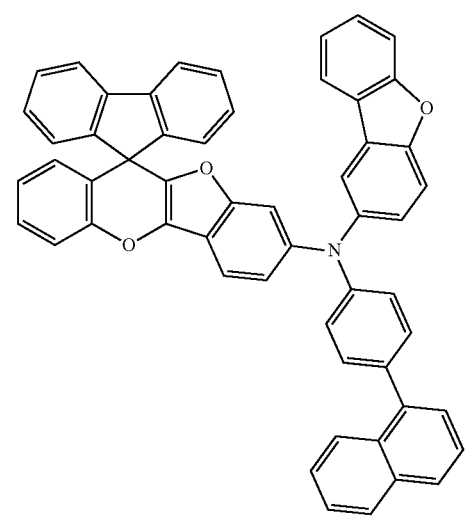
115
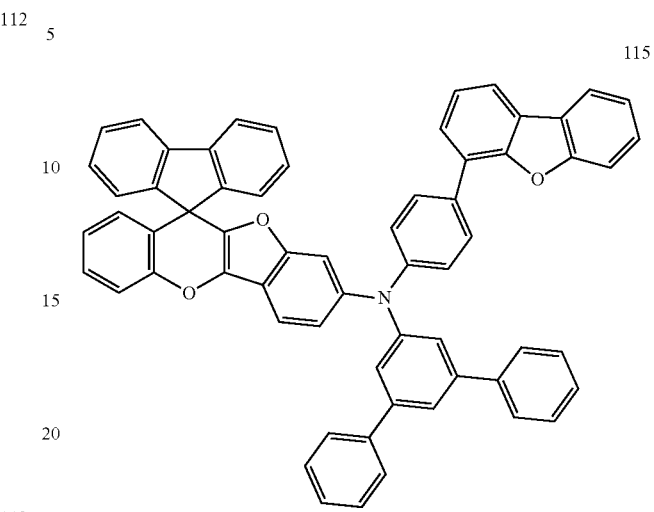
116
117

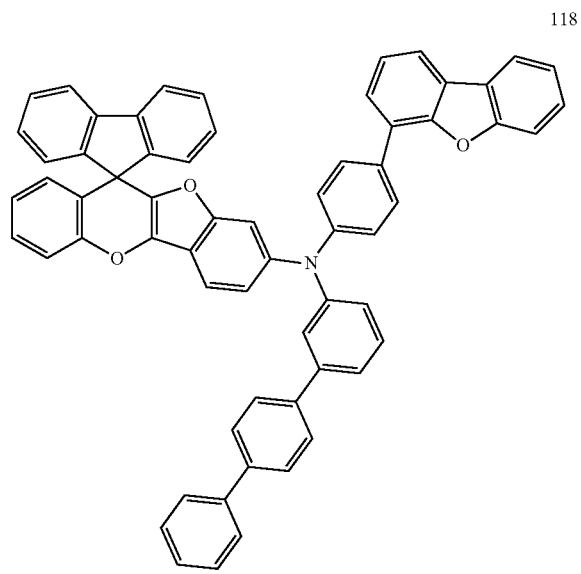
118
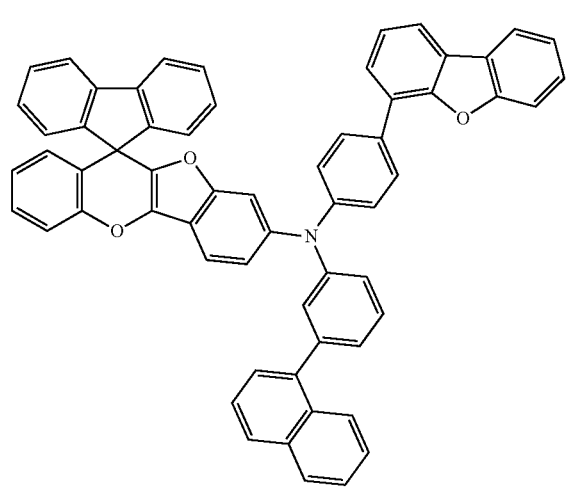
119
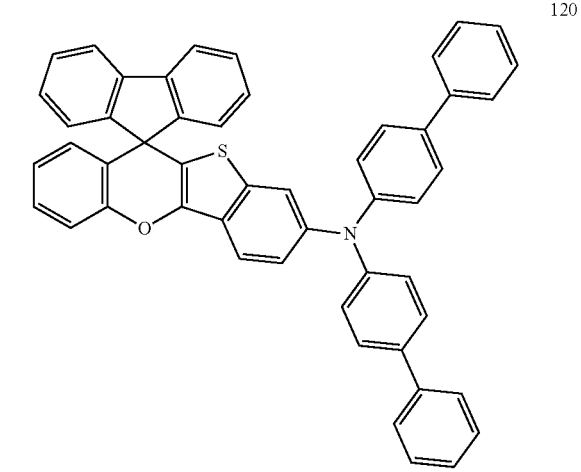
120
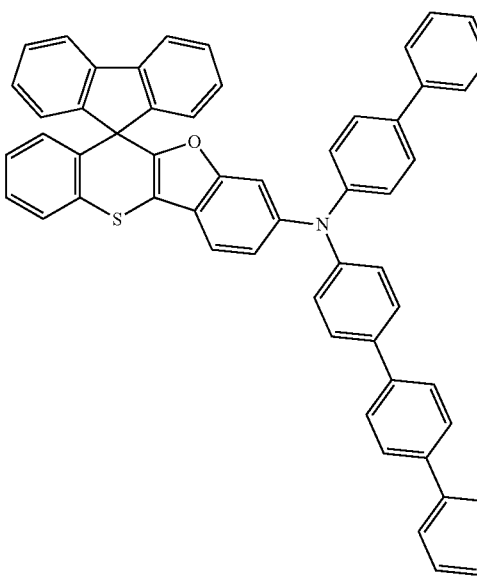
121
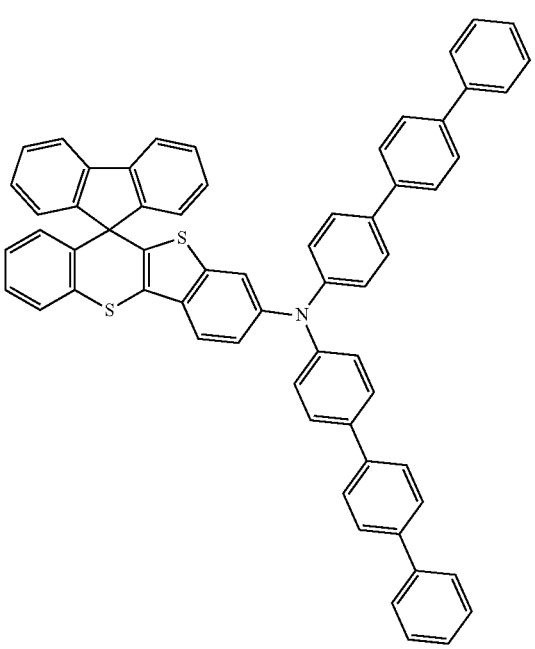
122

123
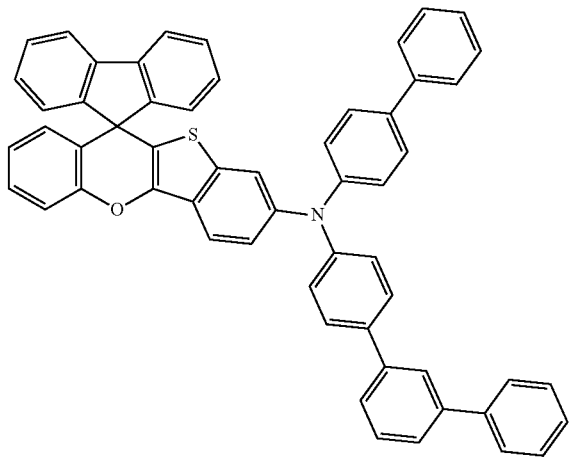
124
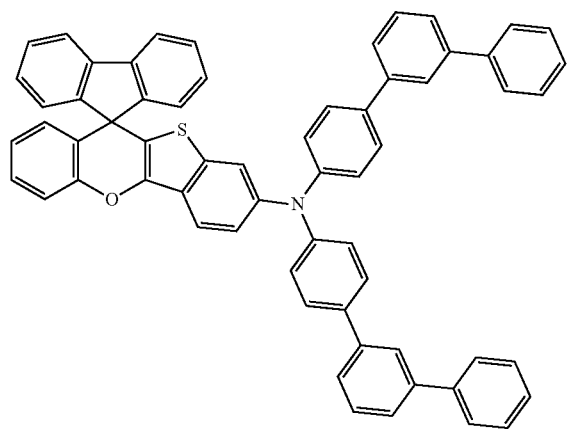
125
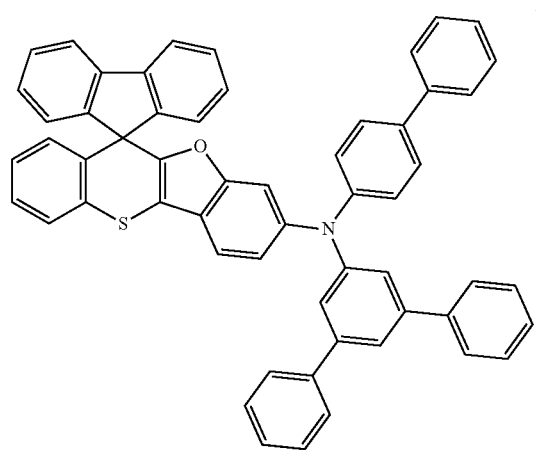
126
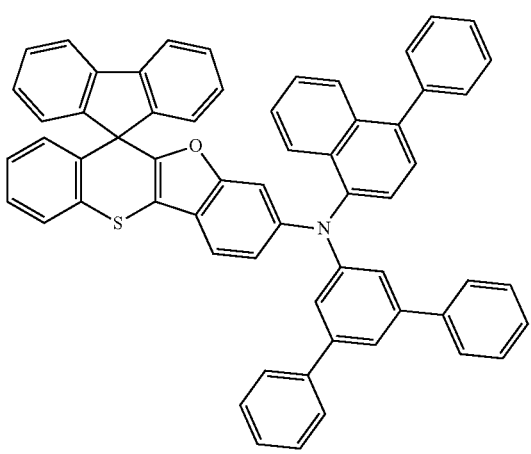
127
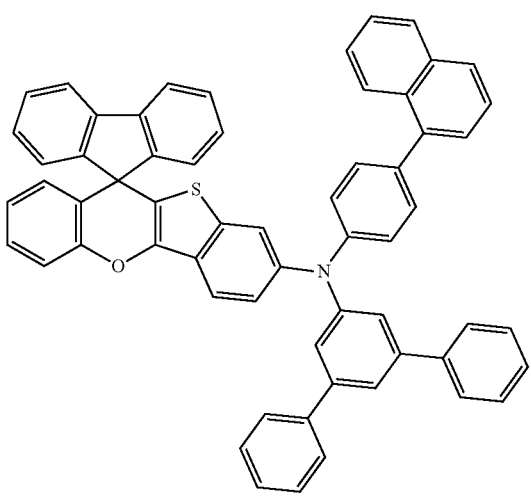
128
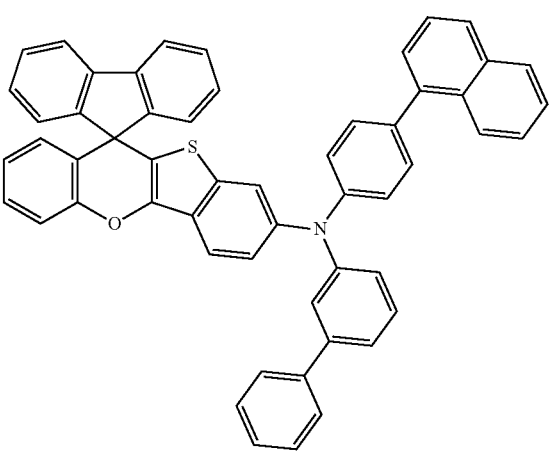

129
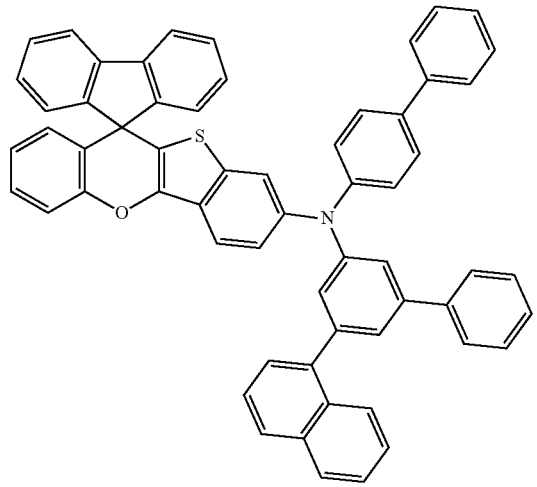
130
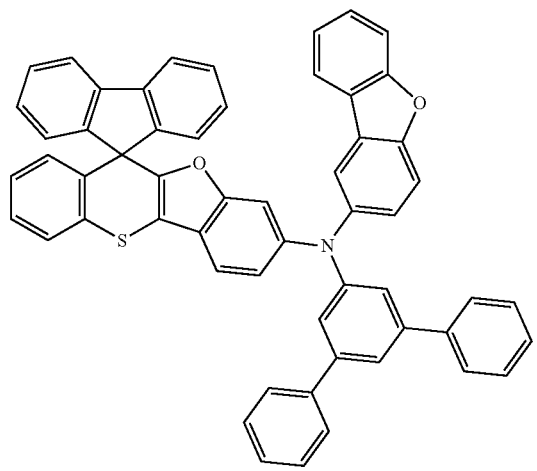
131
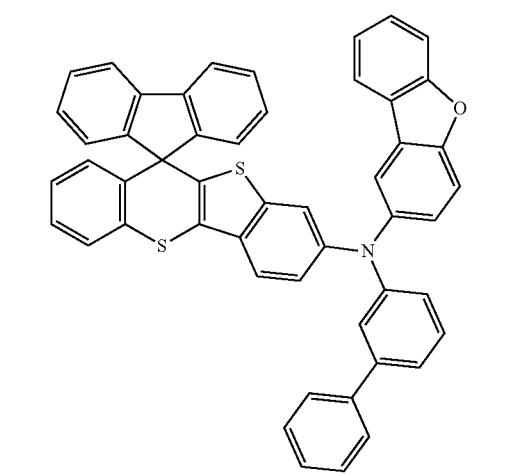
132
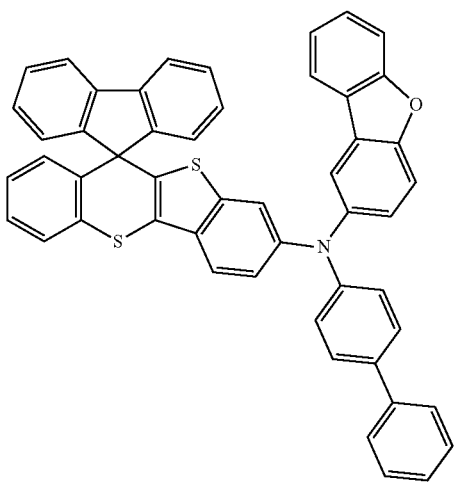
133
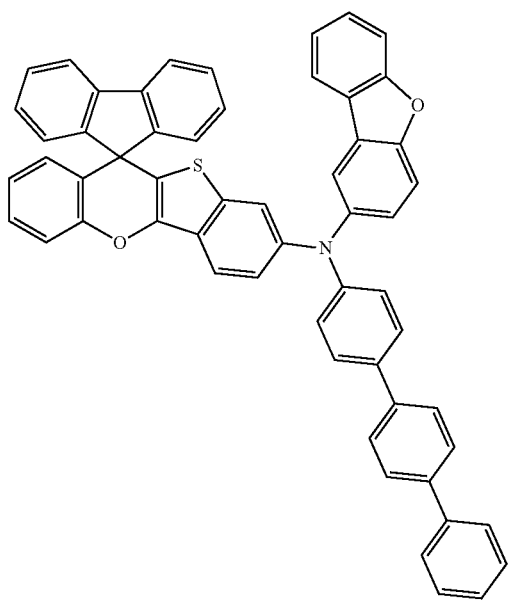
134
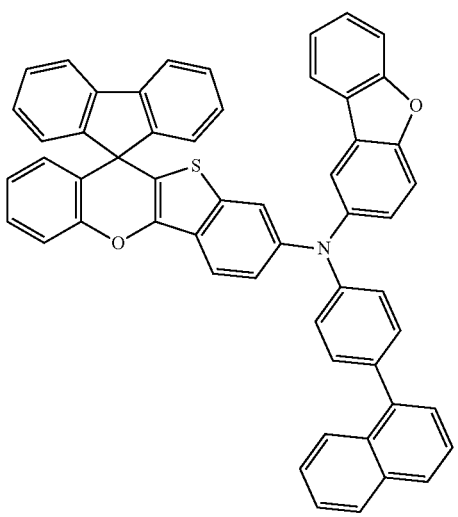

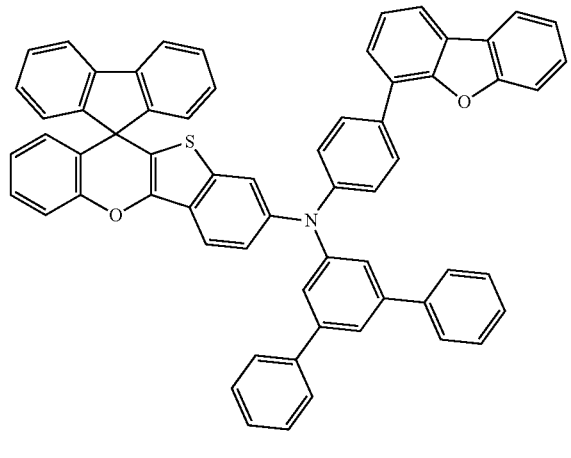
135
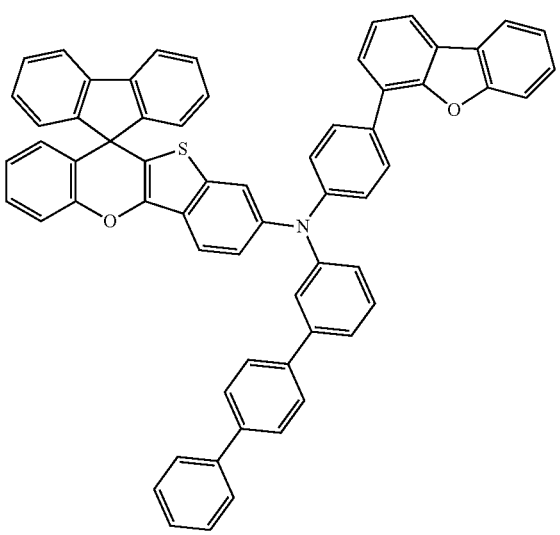
138
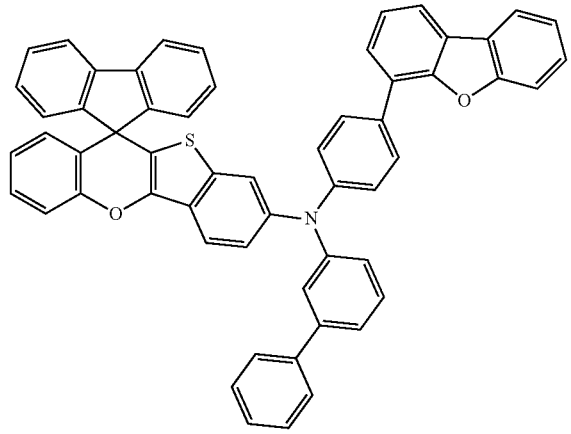
136
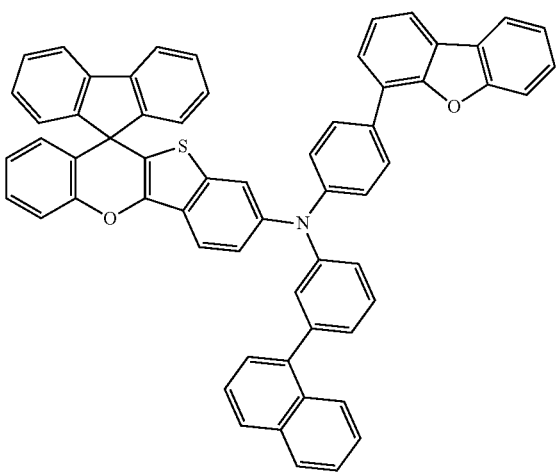
139
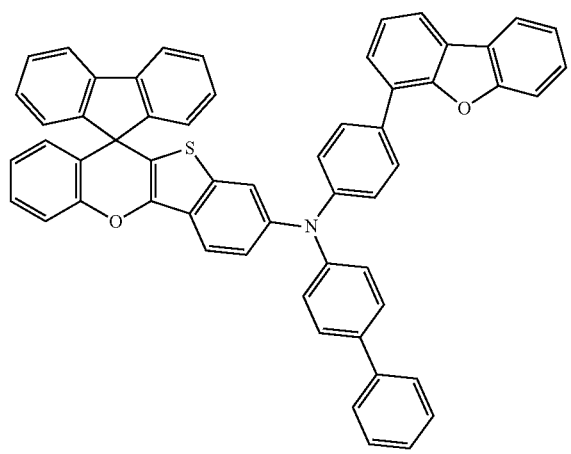
137
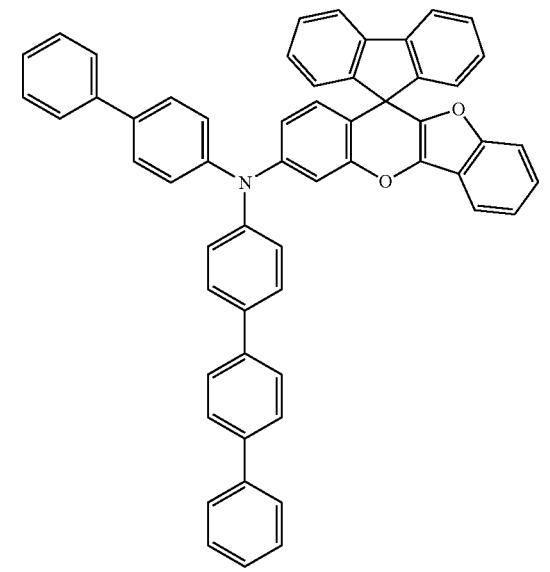
140

141
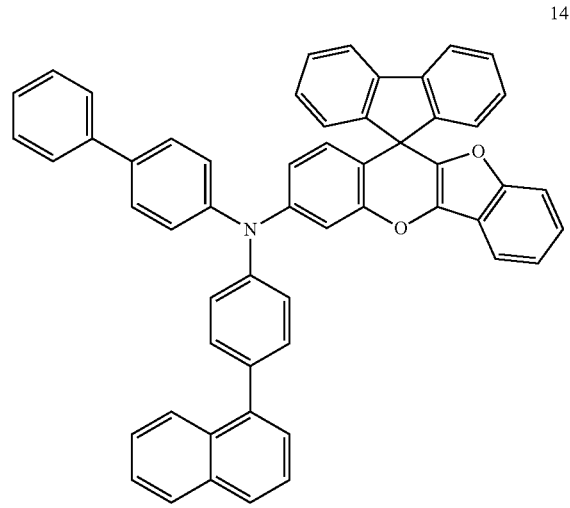
142
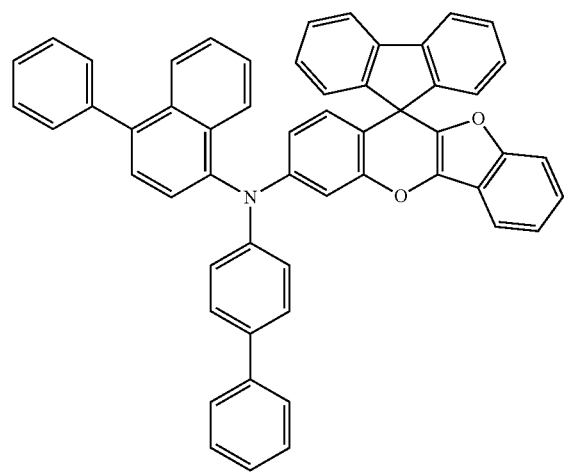
143
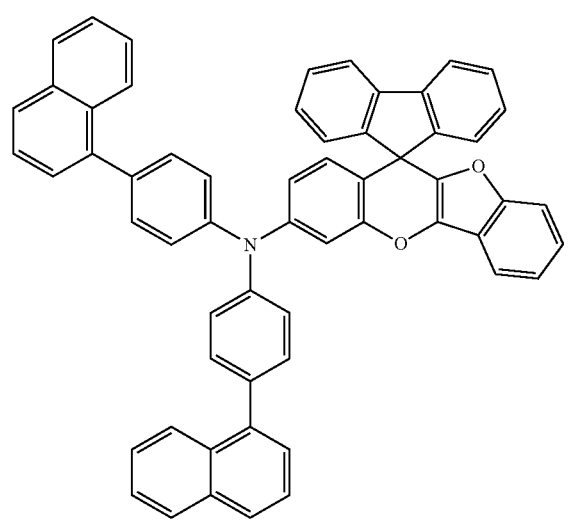
144
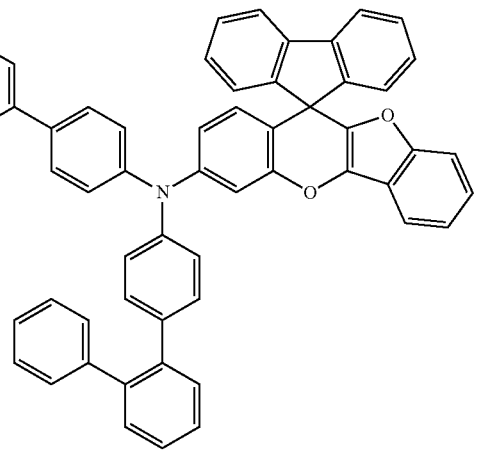
145
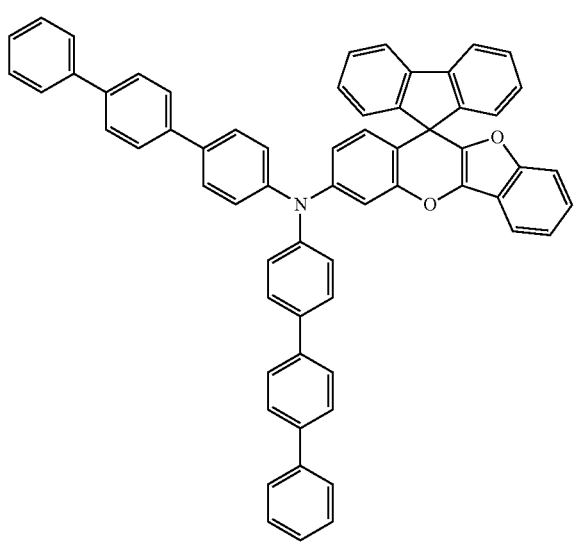
146
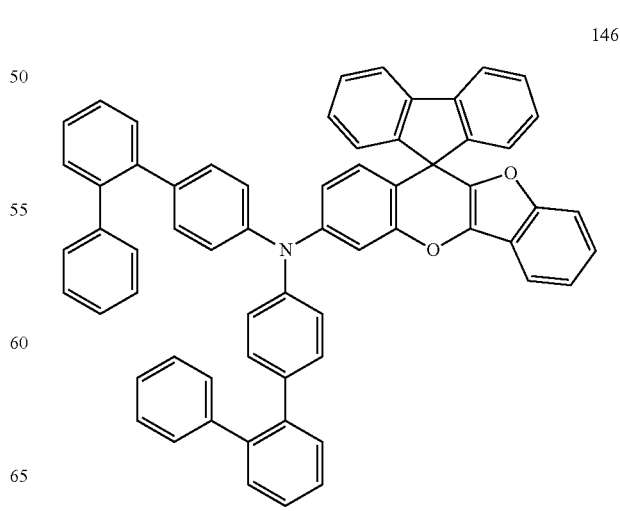

147
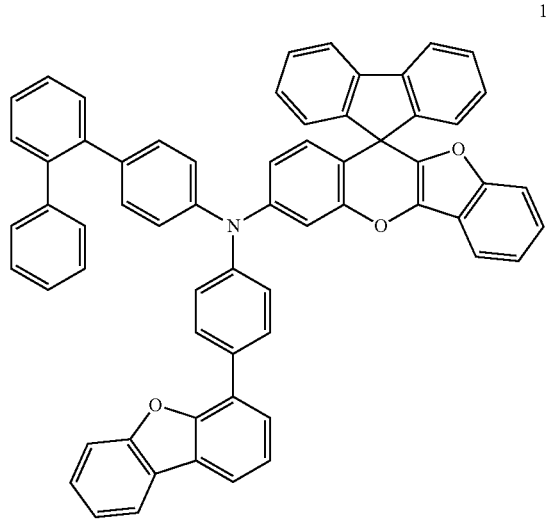
148
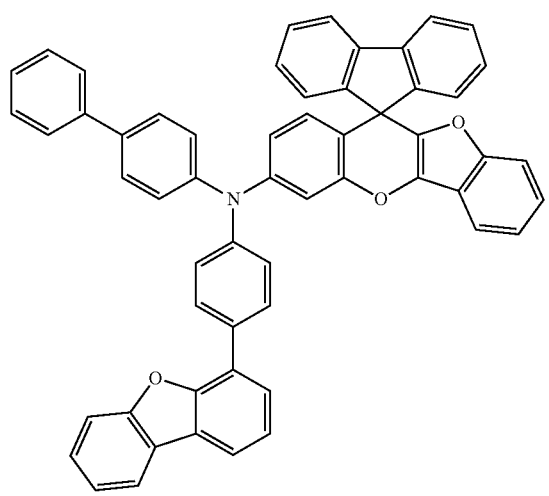
149
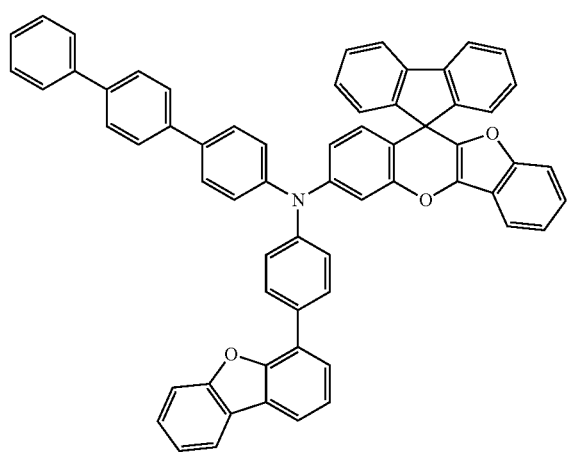
150
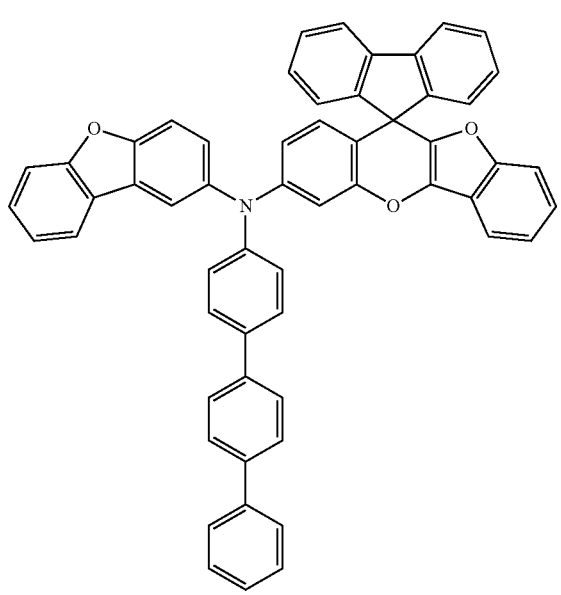
151
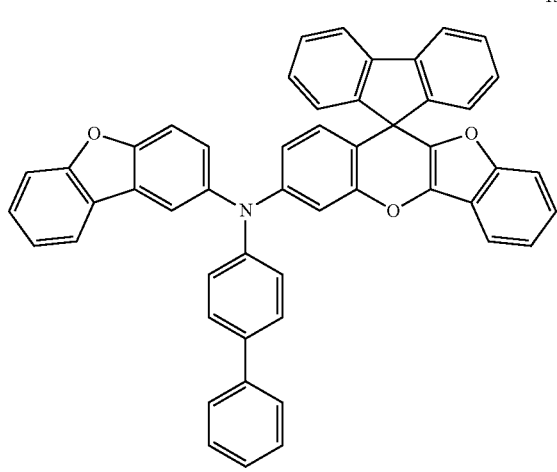
152
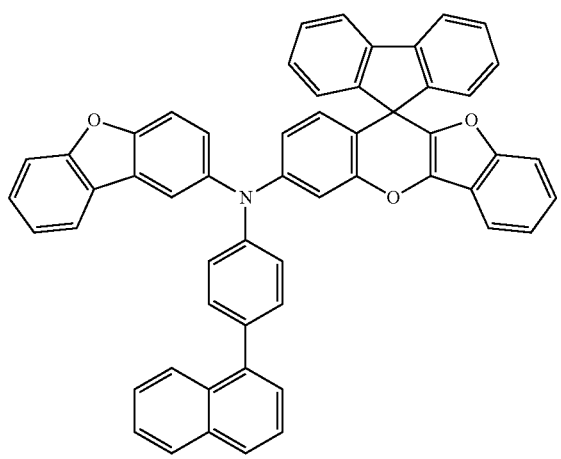

153
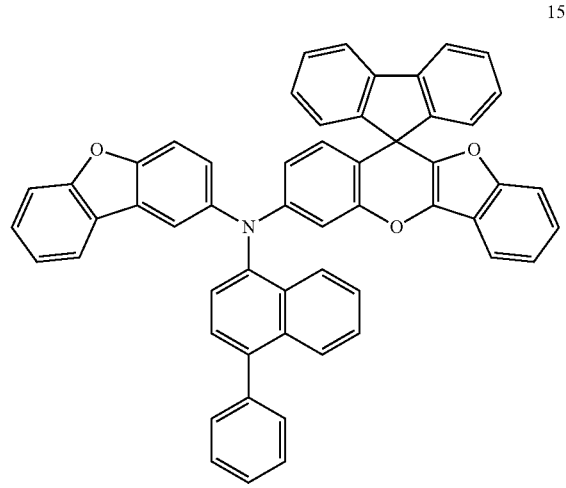
154
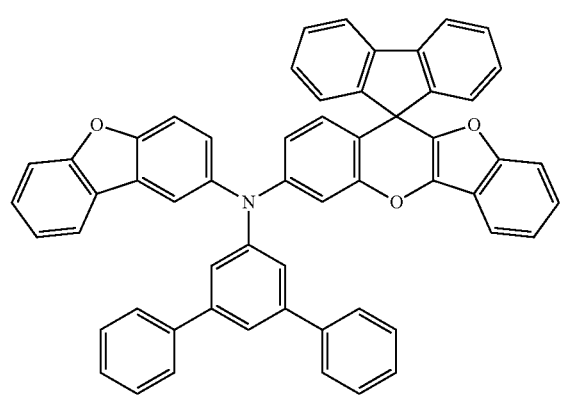
155
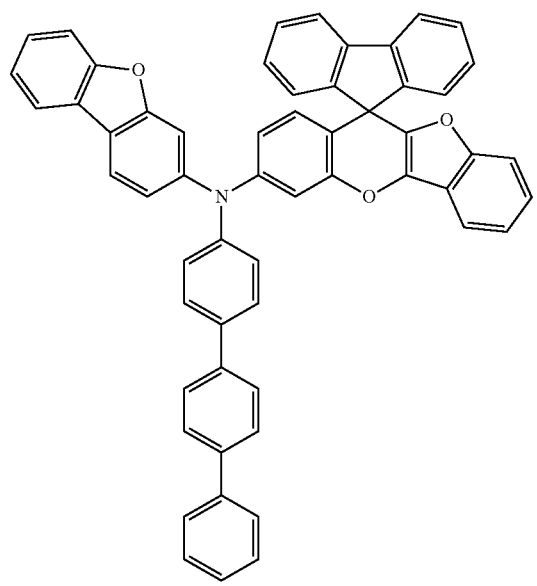
156
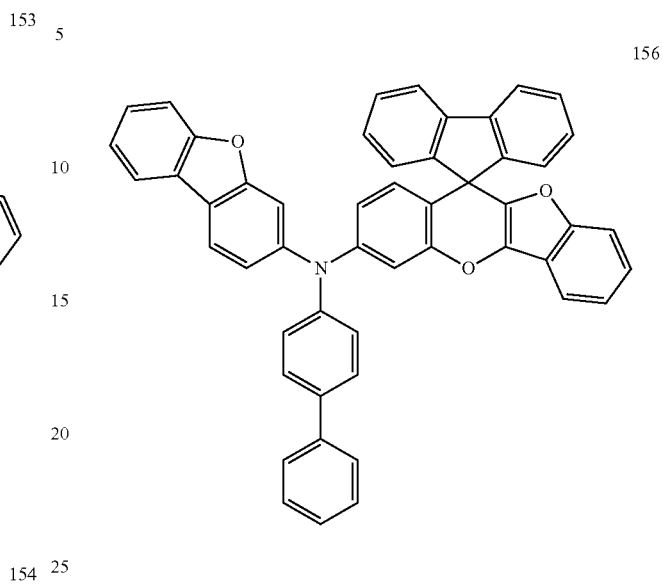
157
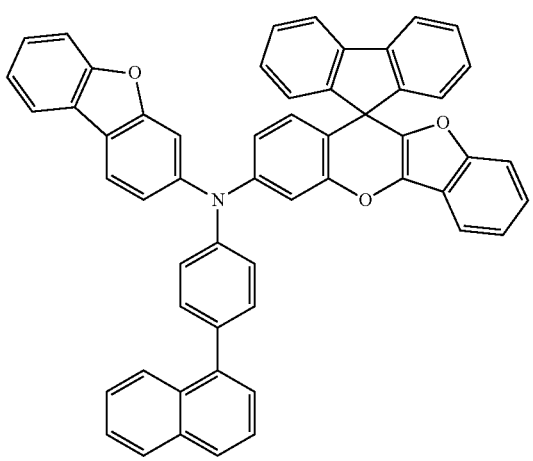
158
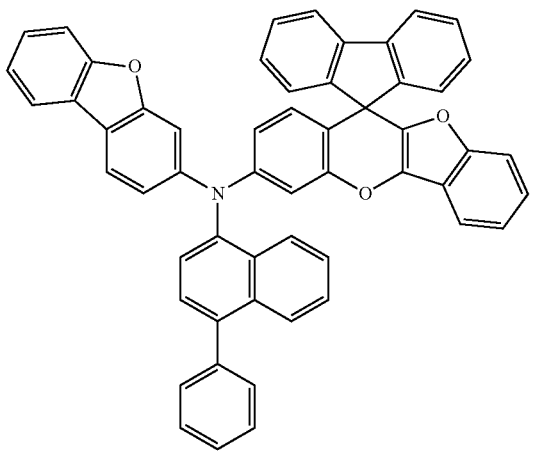

159
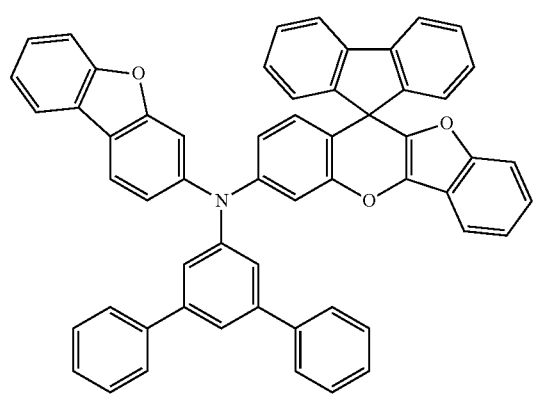
163
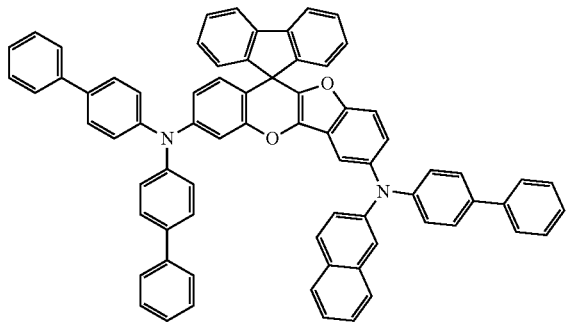
160
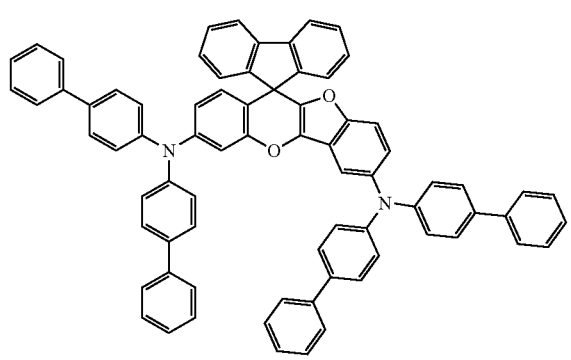
164
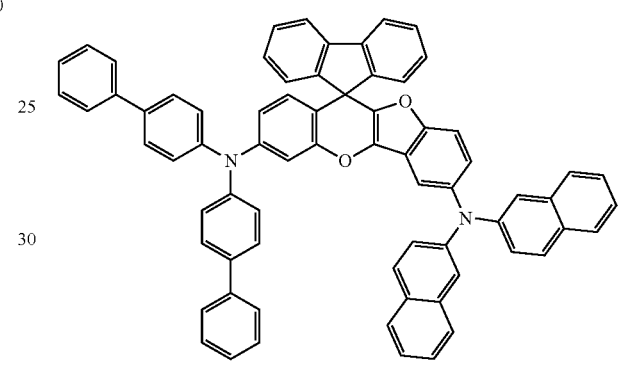
161
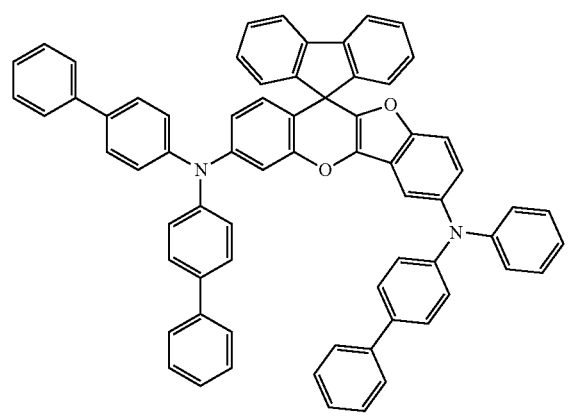
165
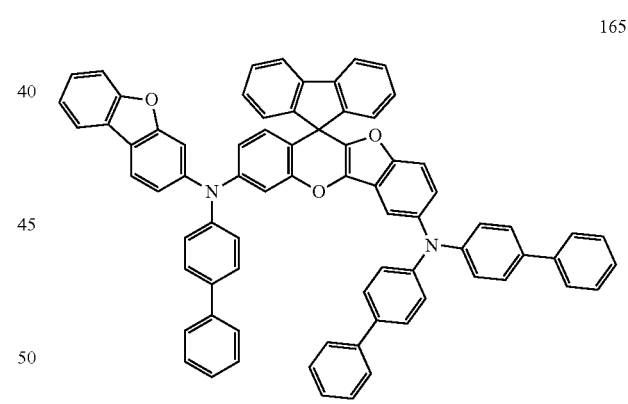
162
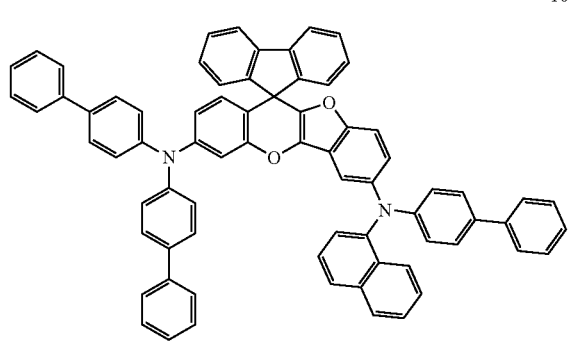
166
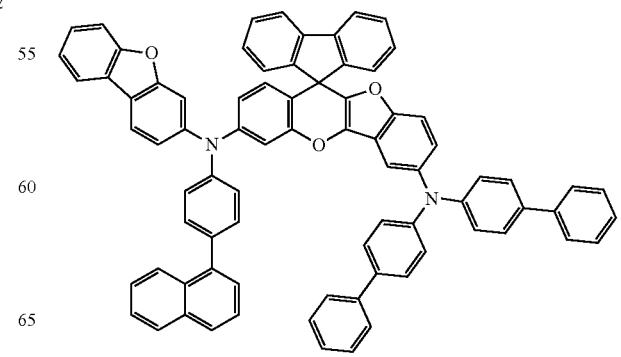

-continued
167
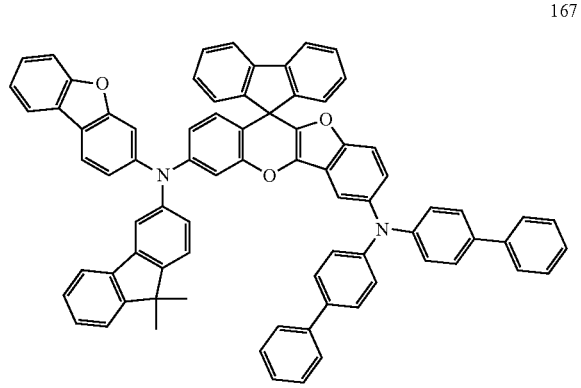
168
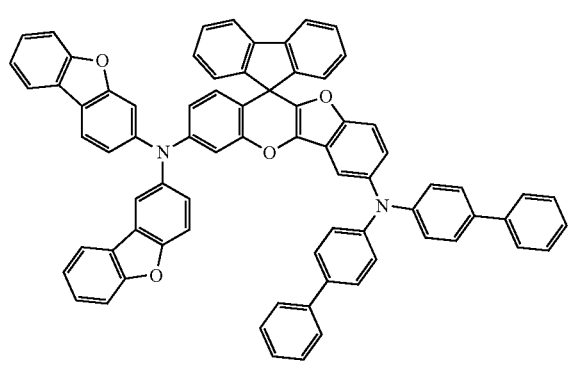
169
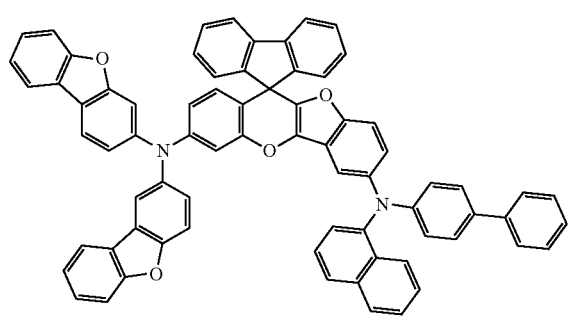
170
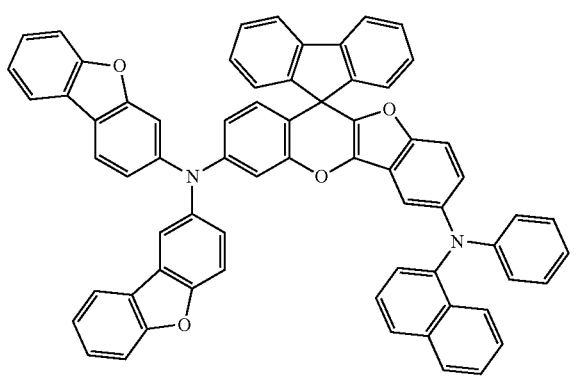
-continued
171
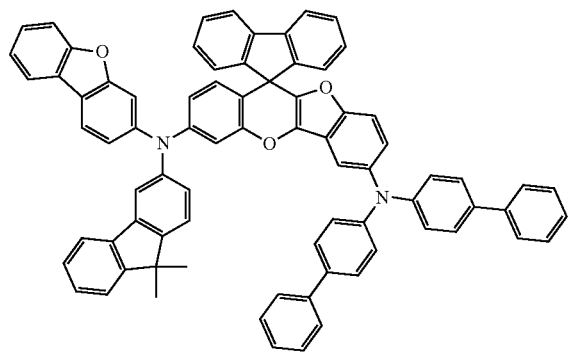
172
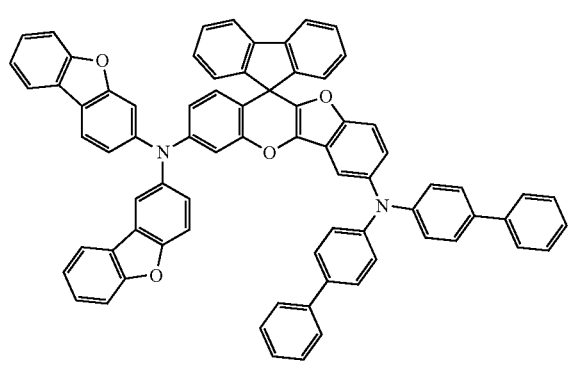
173
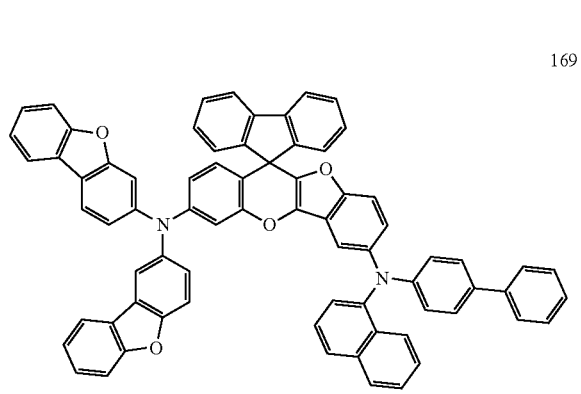
174
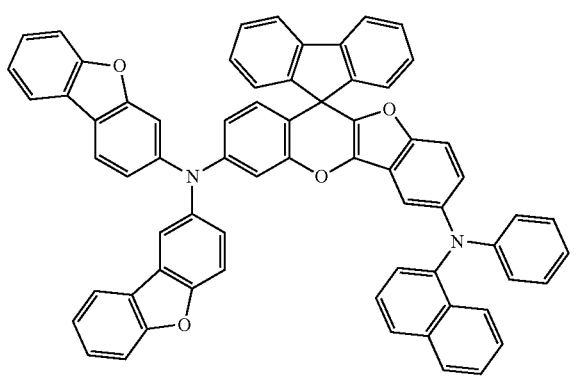

-continued

175

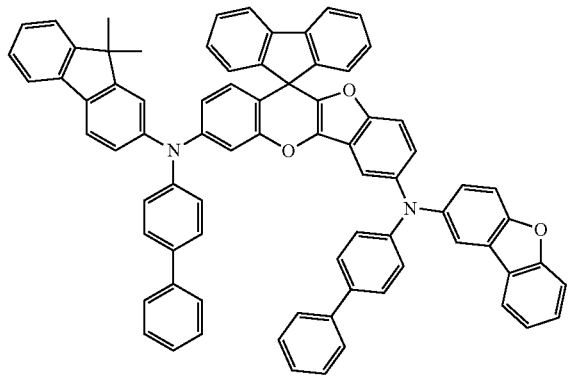

176

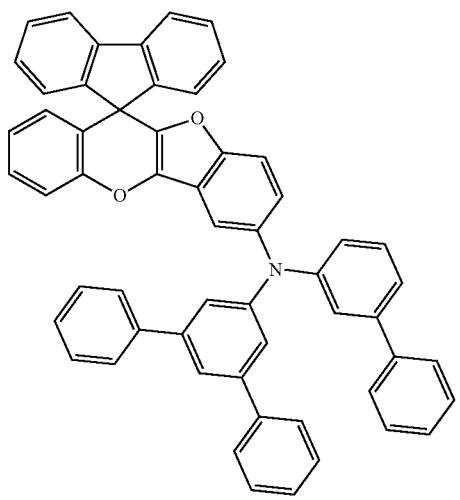

In one implementation of the present disclosure, an organic light-emission device includes at least one organic material layer positioned between an anode and a cathode, wherein the organic material layer contains the compound represented by the Chemical Formula 1.

In one implementation of the present disclosure, in the organic light-emission device, the hole transport material may include the compound represented by the Chemical Formula 1.

In one implementation of the present disclosure, the organic material layer containing the compound represented by Chemical Formula 1 as the hole transport material may include a hole transport layer, an auxiliary hole transport layer, or an electron blocking layer. In one implementation, the organic material layer may include a hole transport layer, an auxiliary hole transport layer or an electron blocking layer, wherein the hole transport layer, the auxiliary hole transport layer or the electron blocking layer may contain one of Compound 1 to Compound 176 as defined above.

In one implementation, the organic material layer includes at least one of a hole transport layer, an auxiliary hole transport layer and an electron blocking layer. The at least one of the hole transport layer, the auxiliary hole transport layer and the electron blocking layer contains the compound represented by the Chemical Formula 1. In one implementation, the organic material layer may include a hole transport layer, an auxiliary hole transport layer and an electron blocking layer, wherein each of the hole transport layer, the auxiliary hole transport layer and the electron blocking layer may contain one of Compound 1 to Compound 176 as defined above.

The organic material layer containing the compound represented by the Chemical Formula 1 as the light-emission material may include a blue light-emission layer.

In one implementation, the organic material layer include a blue light-emission layer. The blue light-emitting layer contains one of Compound 1 to Compound 176 as a blue light-emission layer material.

In one implementation, the organic material layer includes at least one of an electron transport layer and a hole blocking layer. The at least one of the electron transport layer and the hole blocking layer contains the compound represented by the Chemical Formula 1.

FIG. 1 to FIG. 4 show organic light-emission devices according to implementations of the present disclosure, respectively.

In FIG. 1, the organic light-emission device may sequentially include an anode 1, a hole injection layer (HIL) 2, a hole transport layer (HTL) 3, a light-emission layer (EML) 4, an electron transport layer (ETL) 5, and a cathode 6.

Figure 2:
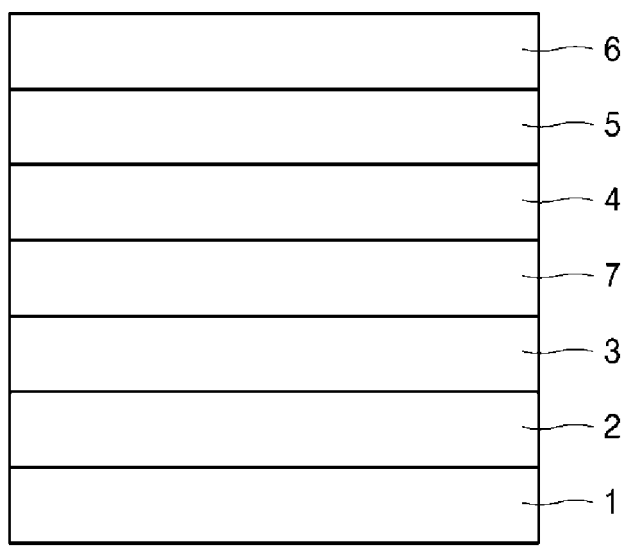

FIG. 2 shows an organic light-emission device according to one implementation of the present disclosure. In FIG. 2, the organic light-emission device may sequentially include an anode 1, a hole injection layer 2, and a hole transport layer 3, an electron blocking layer 7, a light-emission layer 4, an electron transport layer 5 and a cathode 6.

Figure 3:
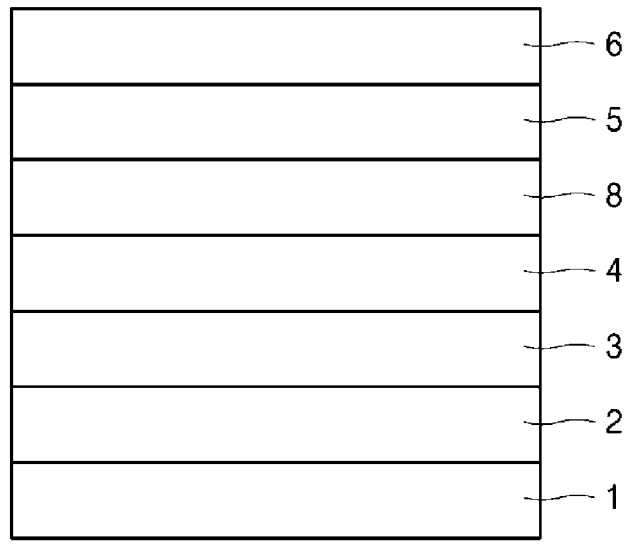

FIG. 3 shows an organic light-emission device according to one implementation of the present disclosure. In FIG. 3, the organic light-emitting device may sequentially include an anode 1, a hole injection layer 2, a hole transport layer 3, a light-emission layer 4, a hole blocking layer (HBL) 8, a an electron transport layer 5 and a cathode 6.

Figure 4:
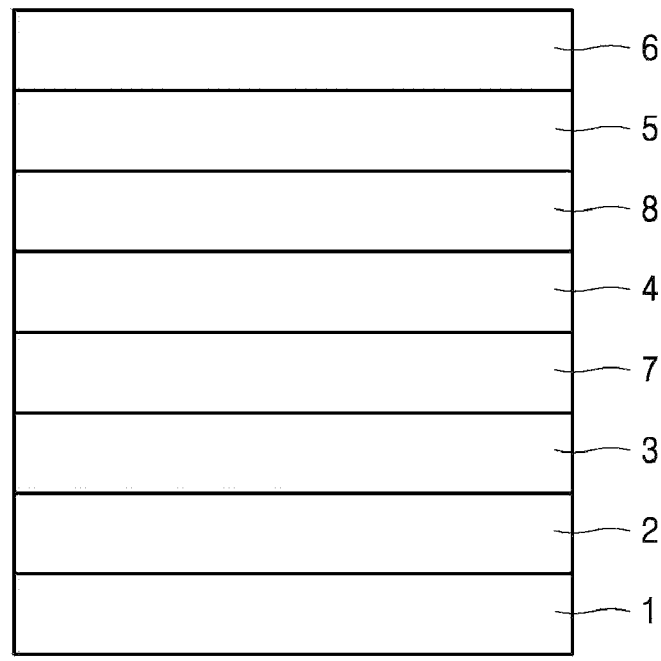

FIG. 4 shows an organic light-emission device according to one implementation of the present disclosure. In FIG. 4, the organic light-emission device sequentially includes an anode 1, a hole injection layer 2, a hole transport layer 3, an electron blocking layer 7, a light-emission layer 4, a hole blocking layer 8, an electron transport layer 5 and a cathode 6.

The anode 1 feeds a hole into the light-emitting layer. The anode may contain a conductive material with a high work function to facilitate the feeding of the hole. When the organic light-emitting device is applied to a bottom emission organic light-emitting display device, the anode may be a transparent electrode made of a transparent conductive material. When the organic light-emitting device is applied to a top emission organic light-emitting display device, the anode may be a multilayer structure with a transparent electrode layer and a reflective layer made of a transparent conductive material.

The cathode 6 feeds electrons to the light-emitting layer. The cathode may contain a conductive material having a low work function to facilitate feeding of electrons. When the organic light-emitting device is applied to a bottom emission organic light-emitting display device, the cathode may be a reflective electrode made of metal. When the organic light-emitting device is applied to a top emission organic light-emitting display device, the cathode may be embodied as a transparent electrode made of a metal and having a small thickness.

The light-emitting layer 4 may emit red R, green G and blue B light beams, and may be made of a phosphorescent material or a fluorescent material.

When the light-emitting layer 4 emits red light, and when the light-emitting layer 4 is made of a phosphorescent material, the light-emitting layer 4 may contain: a host material including CBP (carbazole biphenyl) or mCP(1,3-bis (carbazol-9-yl); and dopants doped into the host including at least one selected from a group consisting of PIQIr (acac)(bis(1-phenylisoquinoline)acetylacetonate iridium), PQIr(acac)(bis(1-phenylquinoline)acetylacetonate iridium), PQIr(tris(1-phenylquinoline)iridium), PtOEP(octaethylporphyrin platinum), and combinations thereof. Alternatively, when the light-emitting layer 4 emits red light, and when the light-emitting layer 4 is made of a fluorescent material, the light-emitting layer 4 may contain PBD:Eu (DBM)3(Phen) or perylene. However, the present disclosure is not limited thereto.

When the light-emitting layer 4 emits green light, and when the light-emitting layer 4 is made of a phosphorescent material, the light-emitting layer 4 may contain: a host material that includes CBP or mCP; and dopants doped into the host including Ir(ppy)3(fac tris(2-phenylpyridine) iridium). Alternatively, when the light-emitting layer 4 emits green light, and when the light-emitting layer 4 is made of a fluorescent material, the light-emitting layer 4 may contain Alq3(tris(8-hydroxyquinolino)aluminum). However, the present disclosure is not limited thereto.

When the light-emitting layer 4 emits blue light, and when the light-emitting layer 4 is made of a phosphorescent material, the light-emitting layer 4 may contain: a host material that includes CBP or mCP; and dopants doped into the host including (4,6-F2ppy)2Irpic. Alternatively, when the light-emitting layer 4 emits blue light, and when the light-emitting layer 4 is made of a fluorescent material, the light-emitting layer 4 may contain at least one selected from a group consisting of spiro-DPVBi, spiro-6P, distyrylbenzene (DSB), distyrylarylene (DSA), PFO-based polymer and PPV-based polymer and combinations thereof, or may contain the compound of the Chemical Formula 1 as the blue fluorescent material. However, the present disclosure is not limited thereto.

The hole injection layer 2 may facilitate the injection of holes. The hole injection layer 2 may contain the compound represented by the Chemical Formula 1. Details of the compound represented by the Chemical Formula 1 are as described above.

The hole injection layer 2 may further contain an additional hole injection material other than the compound represented by the Chemical Formula 1.

In one example, the additional hole injection material may include at least one selected from a group of consisting of, for example, CuPc(cupper phthalocyanine), PEDOT(poly(3, 4)-ethylenedioxythiophene), PANI(polyaniline), NPD(N,N-dinaphthyl-N,N'-diphenyl benzidine) and combinations thereof. However, the present disclosure is not limited thereto.

The hole transport layer 3 may contain, as a hole transport material, a material electrochemically stabilized via cationization (i.e., by losing electrons). Alternatively, the hole transport layer 3 may contain a material that produces a stable radical cation as a hole transport material.

The hole transport layer 3 may contain the compound represented by the Chemical Formula 1. Details of the compound represented by the Chemical Formula 1 are as described above.

The hole transport layer 3 may further contain an additional hole transport material other than the compound represented by the Chemical Formula 1.

The additional hole transport material may contain aromatic amine to be easily cationized. In one example, the additional hole transport material may include at least one selected from a group of consisting of NPD(N,N-dinaphthyl-N,N'-diphenylbenzidine), TPD(N,N'-bis-(3-methylphenyl)-N,N'-bis-(phenyl)-benzidine), spiro-TAD(2,2',7,7'-tetrakis(N,N-dimethylamino)-9,9-spirofluorene), MTDATA (4,4',4-Tris(N-3-methylphenyl-N-phenylamino)-triphenylamine) and combinations thereof. However, the present disclosure is not limited thereto.

The electron transport layer 5 receive electrons from the cathode. The electron transport layer 5 may transfer the supplied electrons to the light-emitting layer.

The electron transport layer 5 may serve to facilitate the transport of electrons. The electron transport layer 5 contains an electron transport material.

The electron transport material may be electrochemically stabilized by being anionic (i.e., by obtaining electrons). Alternatively, the electron transport material may produce the stable radical anion. Alternatively, the electron transport material may contain a heterocyclic ring to be easily anionized by heteroatoms.

In one example, the electron transport material may include at least one selected from a group of consisting of, for example, PBD(2-(4-biphenylyl)-5-(4-tert-butylphenyl)-1,3,4oxadiazole), TAZ(3-(4-biphenyl)4-phenyl-5-tert-butylphenyl-1,2,4-triazole), spiro-PBD, TPBi(2,2',2-(1,3,5-benzinetriyl)-tris(1-phenyl-1-H-benzimidazole), oxadiazole, triazole, phenanthroline, benzoxazole, benzthiazole, and combinations thereof. However, the present disclosure is not limited thereto.

In one example, the electron transport material may include an organic metal compound such as an organic aluminum compound, or an organic lithium compound including at least one selected from a group of consisting of, for example, Alq3(tris(8-hydroxyquinolino)aluminum), Liq (8-hydroxyquinolinolatolithium), BAlq(bis(2-methyl-8-quinolinolate)-4-(phenylphenolato)aluminium), and SAlq, etc. However, the present disclosure is not limited thereto.

Specifically, the organometallic compound may be an organic lithium compound.

More specifically, a ligand bound to the lithium of the organolithium compound may be a hydroxyquinoline based ligand.

When the hole moves through the light-emission layer 4 to the cathode 6, or when the electron travels through the light-emission layer 4 to the anode 1, this may lead to a reduction in the life-span and efficiency of the device. To prevent this situation, an organic light-emission device according to one implementation of the present disclosure may include at least one electron blocking layer (EBL) 7 adjacent to the light-emission layer 4 and a hole blocking layer (HBL) 8 adjacent to the light-emission layer 4. The electron blocking layer 7 may be located between the hole transport layer 3 and the light-emission layer 4. The electron blocking layer 7 may contain the compound represented by the Chemical Formula 1. Details of the compound represented by the Chemical Formula 1 are as described above.

The electron blocking layer 7 may further contain an additional electron blocking material other than the compound represented by the Chemical Formula 1.

In one example, the additional electron blocking material may include at least one selected from a group consisting of, for example, TCTA, tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, 1,1-bis(4-(N,N'-di(ptolyl)amino)phenyl)cyclohexane (TAPC), MTDATA, mCP, mCBP, CuPC, N,N'-bis[4-[bis 3-methylphenyl)amino]phenyl]-N,N'-diphenyl-[1,1'-biphenyl]-4,4'-diamine (DNTPD), TDAPB and combinations thereof. However, the present disclosure is not limited thereto.

The hole blocking layer 8 may be located between the electron transport layer 5 and the light-emission layer 4. The hole blocking layer 8 may contain the compound represented by the Chemical Formula 1. Details of the compound represented by the Chemical Formula 1 are as described above.

The hole blocking layer 8 may further contain an additional hole blocking material other than the compound represented by the Chemical Formula 1.

In one example, the additional hole blocking material may include at least one selected from a group of consisting of, for example, oxadiazole, triazole, phenanthroline, benzoxazole, benzothiazole, benzimidazole, triazine, and combinations thereof. However, the present disclosure is not limited thereto.

The organic material layer may further include, in addition to the electron transport layer, one selected from a group consisting of a hole injection layer, a hole transport layer, an electron blocking layer, a hole blocking layer, an electron injection layer, and a combination thereof. Each of the hole injection layer, the hole transport layer, the electron blocking layer, the hole blocking layer, the electron transport layer and the electron injection layer may be formed of a single layer or a stack of a plurality of layers.

The organic material layer may further include an electron injection layer. The electron injection layer serves to facilitate the injection of electrons and contains an electron injection material. The electron injection material may include, but is not limited to, at least one selected from a group of consisting of Alq3(tris(8-hydroxyquinolino)aluminum), PBD, TAZ, spiro-PBD, BAlq, SAlq and combinations thereof. Alternatively, the electron injection layer may be made of a metal compound. The metal compound may include, but is not limited to, at least one selected from a group of consisting of, for example, LiQ, LiF, NaF, KF, RbF, CsF, FrF, $BeF_2$, $MgF_2$, $CaF_2$, $SrF_2$, $BaF_2$ and $RaF_2$.

The organic light-emitting device according to the present disclosure may be applied to organic light emitting display devices such as a mobile phone and TV. For example, FIG. 5 is a schematic cross-sectional view of an organic light emitting display device applicable to a mobile phone according to an exemplary embodiment of the present disclosure.

Figure 5:
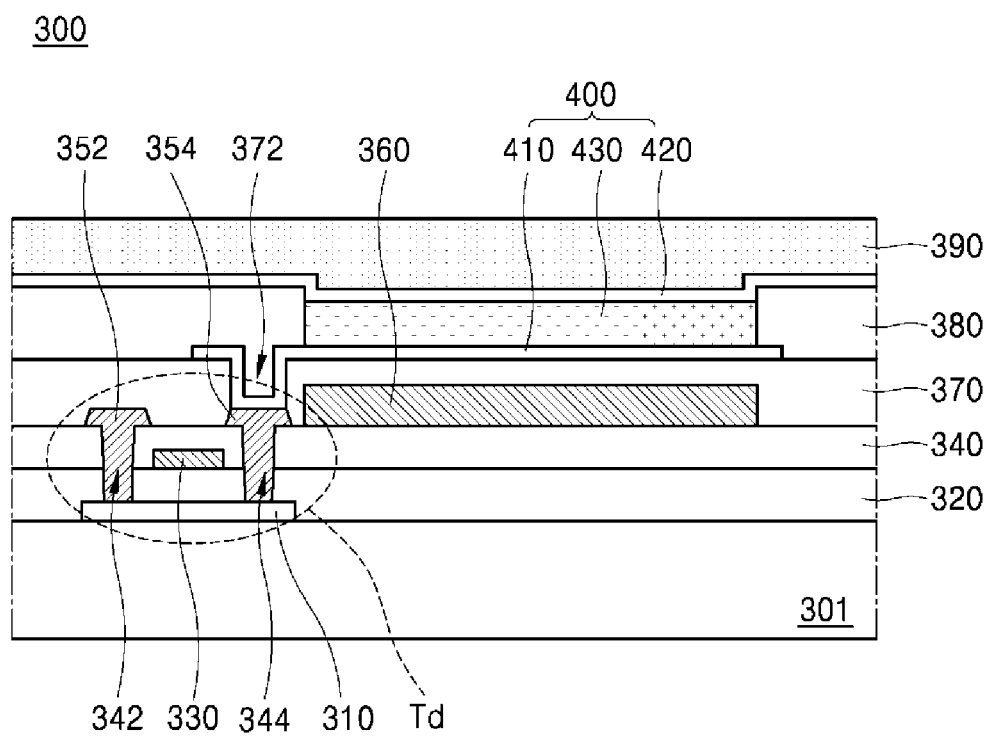
FIG. 5 is a schematic cross-sectional view of an organic electroluminescence display device with an organic light-emission device according to one embodiment of the present disclosure.

As shown in FIG. 5, the organic light-emitting display device 300 may include a substrate 301, an organic light-emitting device 400, and an encapsulating layer 390 covering the organic light-emitting device 400. On the substrate 301, a drive thin-film transistor Td, which is a drive device, and the organic light-emitting device 400, which is connected to the drive thin-film transistor Td, are positioned.

Although not shown, on the substrate 301, a gate line and a data line, which define a pixel region, a power line extending parallel to and spaced from either the gate line or the data line, a switching thin-film transistor connected to the gate line and data line, and a storage capacitor connected to a power line and one electrode of the switching thin-film transistor are formed.

The driving thin-film transistor Td is connected to the switching thin-film transistor, and includes a semiconductor 310, a gate electrode 330, a source electrode 352 and a drain electrode 354.

The semiconductor layer 310 is formed on the substrate 301 and may be made of an oxide semiconductor material, or polycrystalline silicon. When the semiconductor layer 310 is made of an oxide semiconductor material, a light-blocking pattern (not shown) may be formed below the semiconductor layer 310. The light-blocking pattern prevents light from entering the semiconductor layer 310, thereby preventing the semiconductor layer 301 from being deteriorated by light. Alternatively, when the semiconductor layer 310 may be made of polycrystalline silicon, the impurity may be doped into both edges of the semiconductor layer 310.

A gate insulating film 320 made of an insulating material is formed over an entire surface of the substrate 301 an on the semiconductor layer 310. The gate insulating film 320 may be made of an inorganic insulating material such as silicon oxide or silicon nitride.

The gate electrode 330 made of a conductive material such as metal is formed on the gate insulating film 320 and in a central region of the semiconductor layer 310. The gate electrode 330 is connected to a switching thin-film transistor.

An interlayer insulating film 340 made of an insulating material is formed over an entire surface of the substrate 301. The interlayer insulating film 340 may be made of an inorganic insulating material such as silicon oxide or silicon nitride or may be made of an organic insulating material such as benzocyclobutene or photo-acryl.

The interlayer insulating film 340 has first and second contact holes 342 and 344 defined therein for exposing both sides of the semiconductor layer 310. The first and second contact holes 342 and 344 are spaced apart from the gate electrode 330 and disposed around the gate electrode 330.

On the interlayer insulating film 340, the source electrode 352 and the drain electrode 354 made of a conductive material such as metal are formed. The source electrode 352 and the drain electrode 354 are spaced apart from each other and are disposed around the gate electrode 330. The source electrode 352 and the drain electrode 354 contact both sides of the semiconductor layer 310 via the first and second contact holes 342 and 344, respectively. The source electrode 352 is connected to a power line (not shown).

The semiconductor layer 310, the gate electrode 330, the source electrode 352, and the drain electrode 354 form the driving thin-film transistor Td. The driving thin-film transistor Td has a coplanar structure in which the gate electrode 330, the source electrode 352, and the drain electrode 354 are disposed above the semiconductor layer 310.

Alternatively, the driving thin-film transistor Td may have an inverted staggered structure in which the gate electrode is disposed under the semiconductor layer while the source electrode and the drain electrode are disposed above the semiconductor layer. In this case, the semiconductor layer may be made of amorphous silicon. In one example, the switching thin-film transistor (not shown) may have substantially the same structure as the driving thin-film transistor Td.

Alternatively, the organic light-emission display device 300 may include a color filter 360 that absorbs light generated from the organic electroluminescence device 400. In one example, the color filter 360 may absorb red (R), green (G), blue (B) and white (W) lights. In this case, red, green, and blue color filter patterns that absorb red, green, and blue light respectively may be formed separately in each pixel region. Each of these color filter patterns may be disposed so as to overlap with a corresponding organic light-emission layer 430 in the organic light-emission device 400 that emits light of a wavelength band to be absorbed by each color filter pattern. Adopting the color filter 360 may allow the organic electroluminescence display device 300 to render full-color.

In one example, when the organic electroluminescence display device 300 is of a bottom light-emission type, the color filter 360 may be located on top of the inter-layer insulating film 340 and in a region corresponding to the organic light-emission device 400. In an alternative embodiment, when the organic electroluminescence display device 300 is of a top light-emission type, the color filter 360 may be located on top of the second electrode 420 and in a region corresponding to the organic light-emission device 400. In an example, the color filter 360 may be formed with a thickness of 2 to 5 μm.

In one example, a protective layer 370 having a drain contact hole 372 defined therein exposing the drain electrode 354 of the driving thin-film transistor Td is formed to cover the driving thin-film transistor Td.

On the protection layer 370, a first electrode 410 connected to the drain electrode 354 of the driving thin-film transistor Td via the drain contact hole 372 is individually formed in each pixel region.

The first electrode 410 may act as an anode, and may be made of a conductive material having a relatively large work function value. For example, the first electrode 410 may be made of transparent conductive material such as ITO. IZO or ZnO.

In one example, when the organic electroluminescence display device 300 is of a top-emission type, a reflective electrode or reflective layer may be further formed below the first electrode 410. For example, the reflective electrode or reflective layer may be made of any one of aluminum (Al), silver (Ag), nickel (Ni), aluminum-palladium-copper (APC alloy).

On the protection layer 370, a bank layer 380 covering an edge of the first electrode 410 is formed. The bank layer 380 may be constructed to allow a bank hole corresponding to each pixel region to be defined to partially expose the first electrode 410.

An organic light-emitting layer 430 is formed on the first electrode 410. In an example, the organic light-emitting layer 430 may include two or more light-emitting layers as shown in FIG. 1 and FIG. 2.

A second electrode 420 is formed on the organic light-emitting layer 430. The second electrode 420 is positioned on an entirety of the display region and may be made of a conductive material having a relatively small work function value and thus may act as a cathode. For example, the second electrode 400 may be made of any one of aluminum Al, magnesium Mg, and aluminum-magnesium alloy AlMg.

The first electrode 410, the organic light-emitting layer 430 and the second electrode 420 constitute the organic light-emission device 400.

On the second electrode 420, an encapsulation film 390 is formed to prevent external moisture from penetrating into the organic light-emitting device 400. Although not shown, the encapsulation film 390 may have, but is not limited to, a triple layer structure (not shown) sequentially composed of a first inorganic layer, and an organic layer, and a second inorganic layer.

The following Examples of the present disclosure are provided to more fully describe the present disclosure to those skilled in the art. The following Examples may be modified into various other forms. Thus, the scope of the present disclosure is not limited to the following Examples. Rather, the following Examples are provided so that the present disclosure will be more faithful and complete, and are provided to fully convey ideas of the present disclosure to those skilled in the art.

Hereinafter, Examples and Comparative examples will be set forth. The Examples may be only an example of the present disclosure. Thus, the present disclosure is not limited to the Examples.

EXAMPLE

Synthesis Example 1

Compounds 61 and 72

Production of Compound 61-1

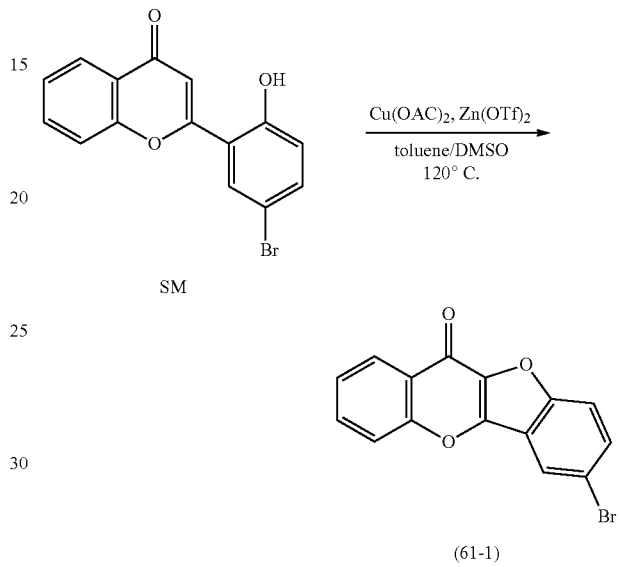

[Reaction Formula 1]

SM (starting material) (15.9 g, 50 mmol), Cu(OAc)$_2$ (10.9 g, 60 mmol), and Zn(OTf)$_2$ (3.63 g, 10 mmol) were completely dissolved into 200 ml of toluene and 50 ml of dimethylsulfoxide (DMSO) in a 500 ml round bottom flask under a nitrogen atmosphere to form a mixture. Then, the mixture was heated and stirred at 120° C. while being refluxed for 24 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 61-1 (12.9 g, yield: 82%).

Production of Compound 61-2

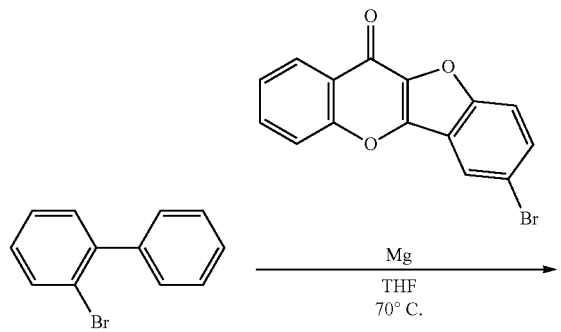

[Reaction Formula 2]

-continued

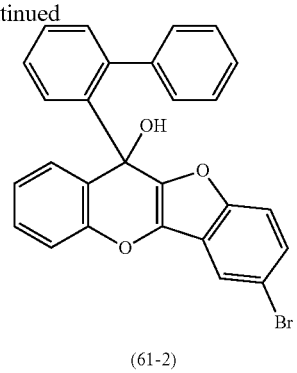

(61-2)

2-bromobiphenyl (9.32 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above compound 61-1 (12.6 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 61-2 (16 g, yield: 85%).

Production of Compound 61-3

[Reaction Formula 3]

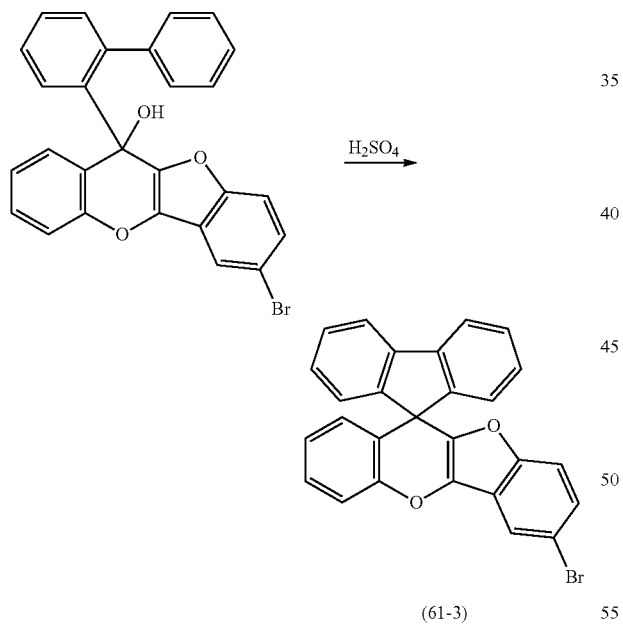

(61-3)

The Compound 61-2 (9.4 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 61-3 (7.13 g, yield: 79%).

Production of Compound 61

[Reaction Formula 4]

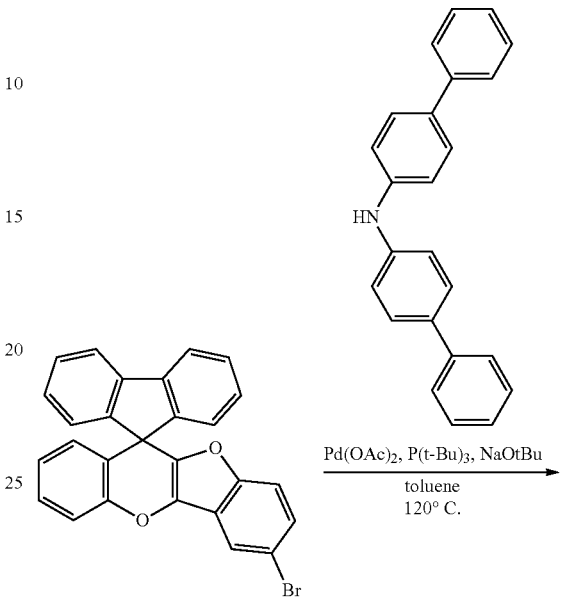

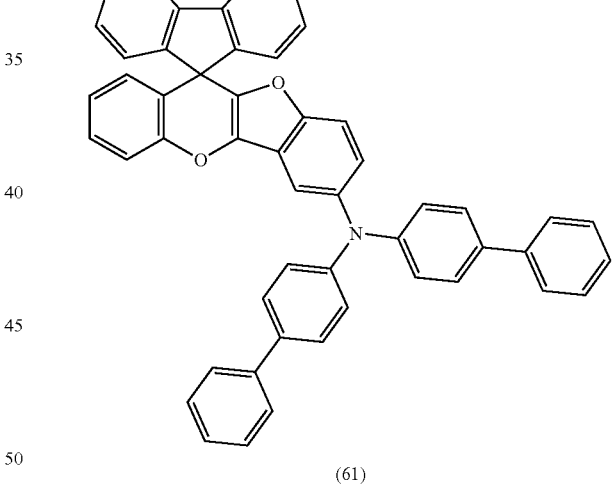

(61)

The Compound 61-3 (9.0 g, 20 mmol), di([1,1'-biphenyl]-4-yl)amine (6.4 g, 20 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 61 (12.5 g, yield: 90%).

Production of Compound 72-1

Production of Compound 72

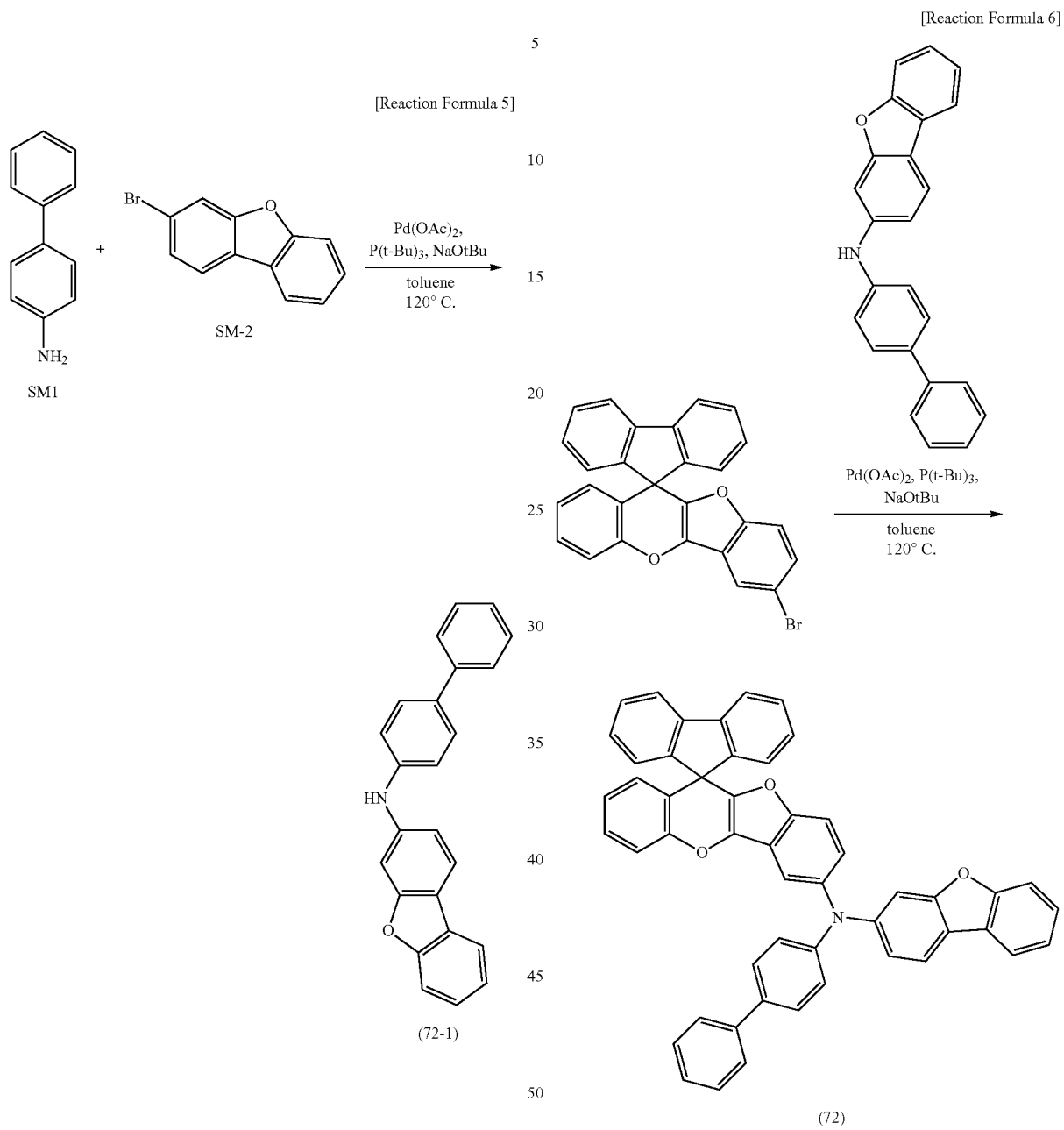

[Reaction Formula 5]

[Reaction Formula 6]

SM1 (3.0 g, 20 mmol), SM2 (5.0 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 72-1 (6.4 g, yield:95%).

The Compound 61-3 (9.0 g, 20 mmol), the compound 72-1 (6.7 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 72 (13.1 g, yield:93%).

Synthesis Example 2

Compounds 3, 15, and 16

Production of Compound 3-1

[Reaction Formula 7]

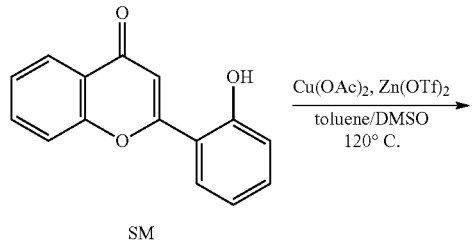

SM (starting material) (11.9 g, 50 mmol), Cu(OAc)$_2$ (10.9 g, 60 mmol), and Zn(OTf)$_2$ (3.63 g, 10 mmol) were completely dissolved into 200 ml of toluene and 50 ml of dimethylsulfoxide (DMSO) in a 500 ml round bottom flask under a nitrogen atmosphere to form a mixture. Then, the mixture was heated and stirred at 120° C. while being refluxed for 24 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 3-1 (11.2 g, yield:95%).

Production of Compound 3-2

[Reaction Formula 8]

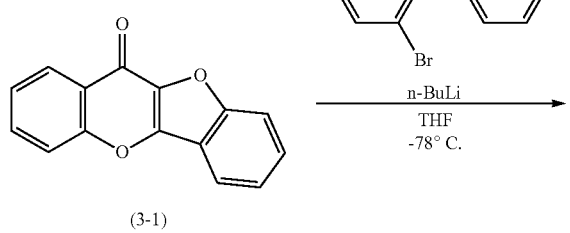

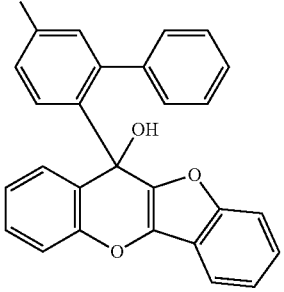

SM (starting material) (10.7 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 3-1 (9.5 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 3-2 (13.6 g, yield: 80%).

Production of Compound 3-3

[Reaction Formula 9]

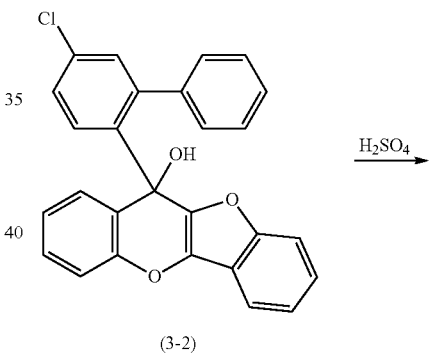

The Compound 3-2 (8.5 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 3-3 (5.9 g, yield:73%).

Production of Compound 3

Production of Compound 15

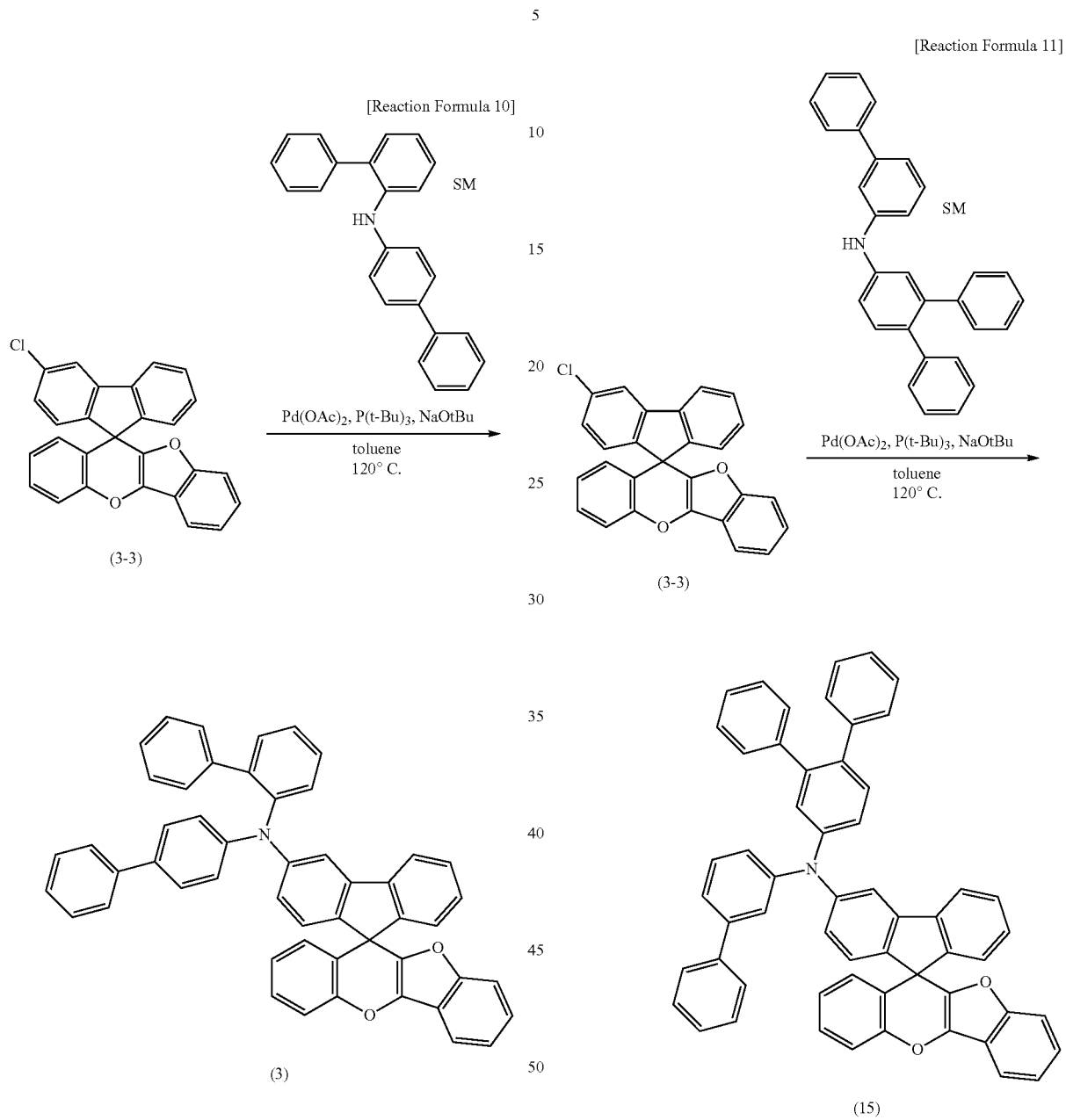

The Compound 3-3 (8.1 g, 20 mmol), SM (starting material) (6.4 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 3 (12.2 g, yield:88%).

The Compound 3-3 (8.1 g, 20 mmol), SM (starting material) (8.0 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 15 (13.2 g, yield:86%).

Production of Compound 26

Synthesis Example 3

Compounds 100, 102, and 111

Production of Compound 100-1

[Reaction Formula 12]

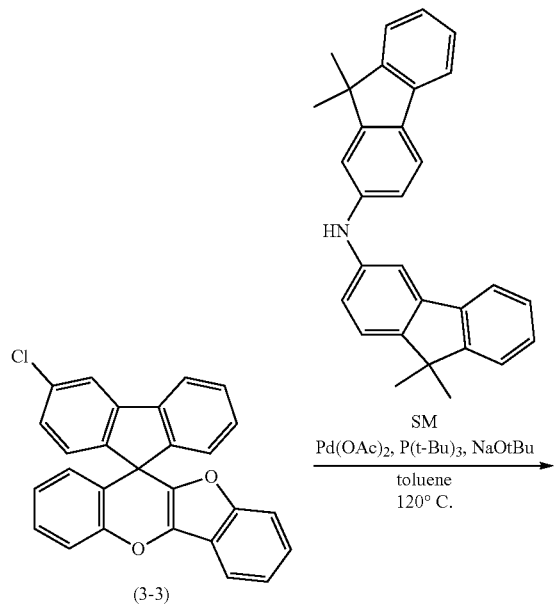

(3-3)

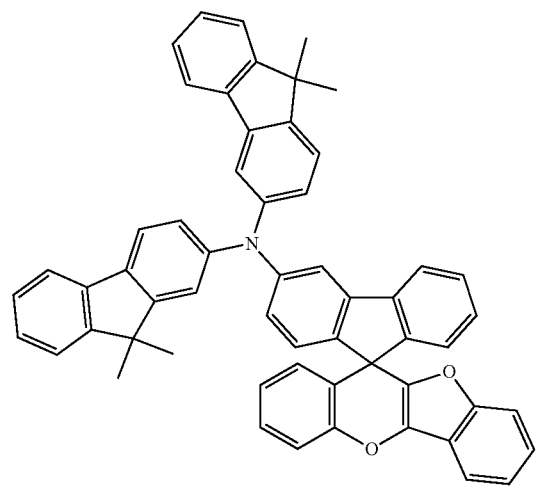

(26)

The Compound 3-3 (8.0 g, 20 mmol), SM (starting material) (8.0 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 26 (13.7 g, yield:89%).

SM (starting material) (12.9 g, 50 mmol), Cu(OAc)$_2$ (10.9 g, 60 mmol), and Zn(OTf)$_2$ (3.63 g, 10 mmol) were completely dissolved into 200 ml of toluene and 50 ml of dimethylsulfoxide (DMSO) in a 500 ml round bottom flask under a nitrogen atmosphere to form a mixture. Then, the mixture was heated and stirred at 120° C. while being refluxed for 24 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 100-1 (14.2 g, yield:90%).

Production of Compound 100-2

[Reaction Formula 14]

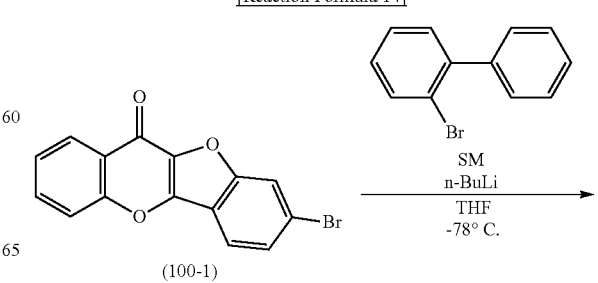

(100-1)

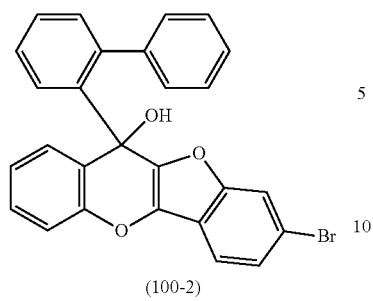

(100-2)

SM (starting material) (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 100-1 (12.6 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 100-2 (16.3 g, yield: 87%).

Production of Compound 100-3

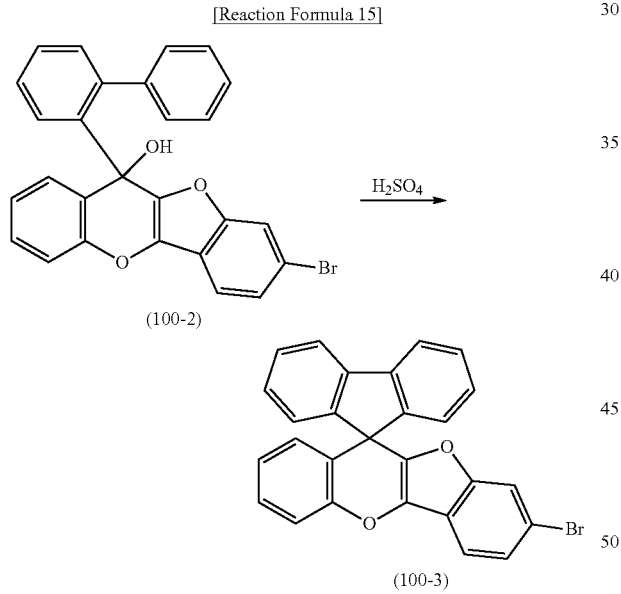

The Compound 100-2 (9.4 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 100-3 (7.2 g, yield:80%).

Production of Compound 100

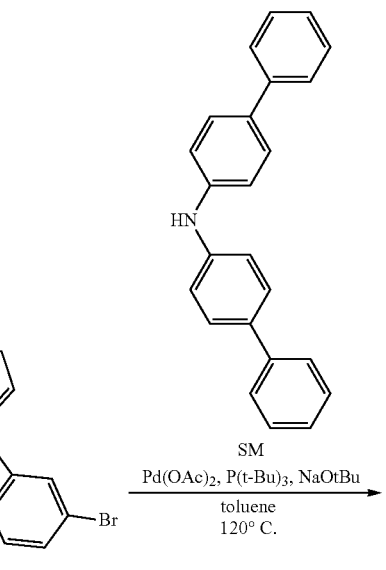

The Compound 100-3 (9.1 g, 20 mmol), SM (starting material) (6.4 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 100 (12.7 g, yield:92%).

Production of Compound 102

Production of Compound 111

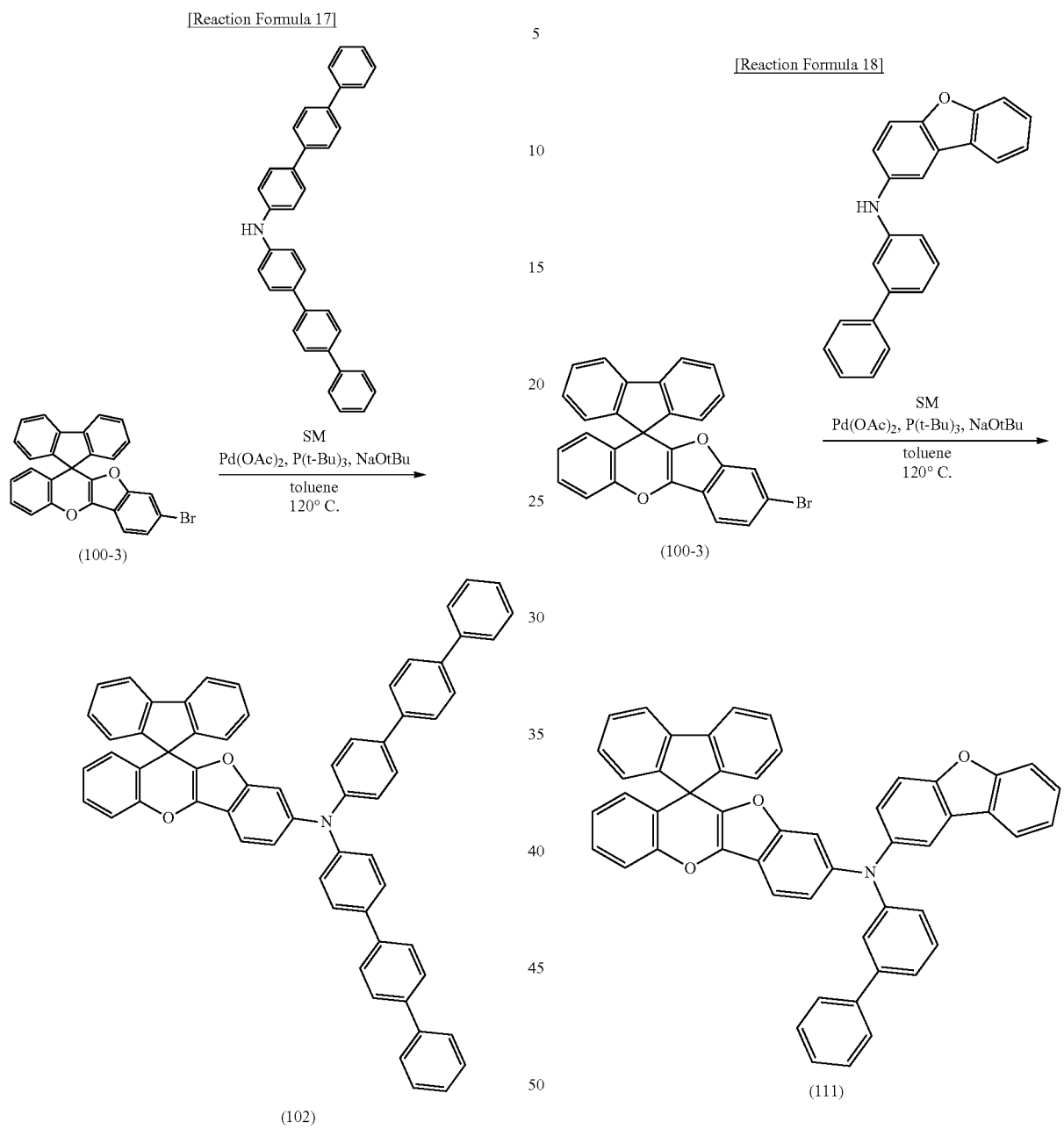

[Reaction Formula 17]

[Reaction Formula 18]

The Compound 100-3 (9.1 g, 20 mmol), SM (starting material) (9.5 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 102 (15.2 g, yield: 90%).

The Compound 100-3 (9.1 g, 20 mmol), SM (starting material) (6.7 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 111 (12.4 g, yield:88%).

Synthesis Example 4

Compounds 122 and 131

Production of Compound 122-1

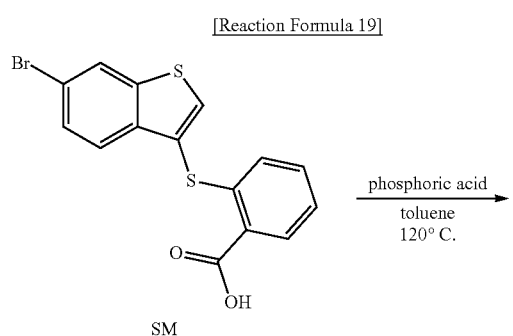

A SM (starting material) (7.3 g, 20 mmol), and phosphoric acid (1.0 g, 10 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 122-1 (5.4 g, yield:78%).

Production of Compound 122-2

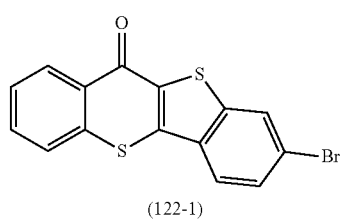

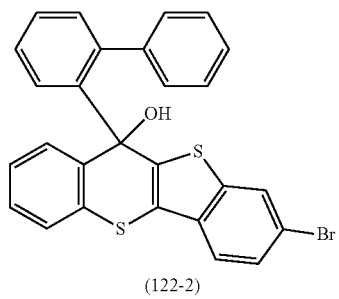

A SM (starting material) (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 122-1 (13.9 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 122-2 (8.3 g, yield:83%).

Production of Compound 122-3

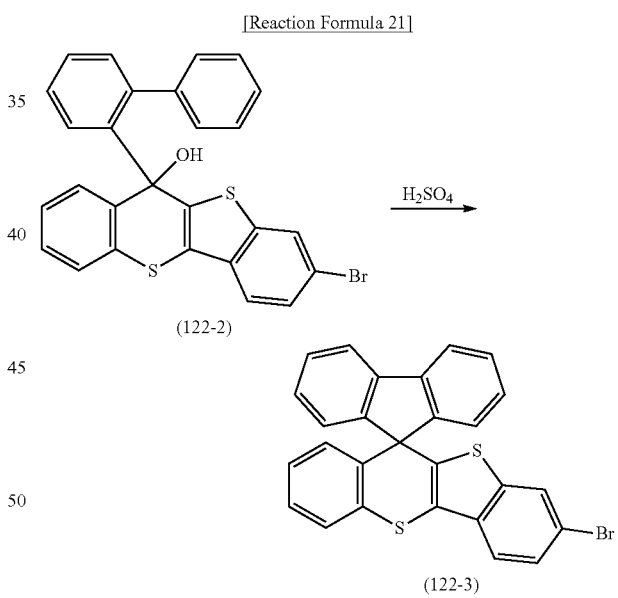

The Compound 122-2 (10.0 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 122-3 (8.0 g, yield:84%).

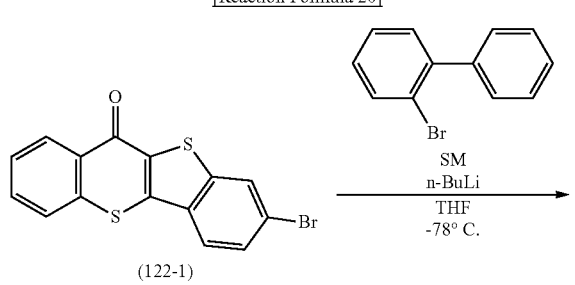

Production of Compound 122

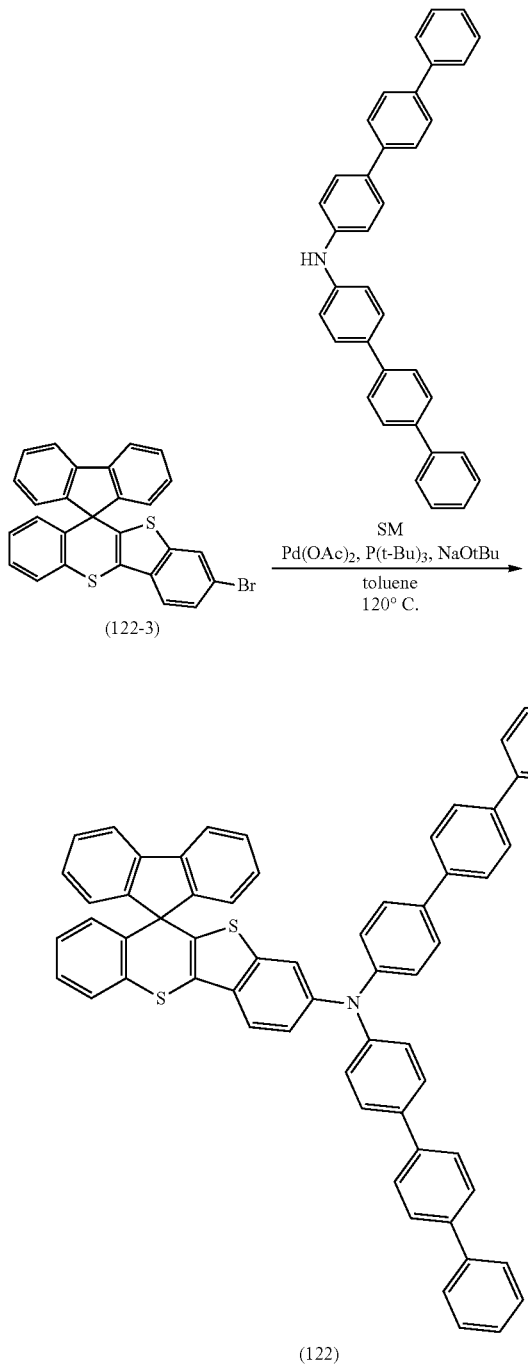

The composition 122-3 (9.7 g, 20 mmol), SM (starting material) (9.5 g, 20 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 122 (14.5 g, yield:83%).

Production of Compound 131

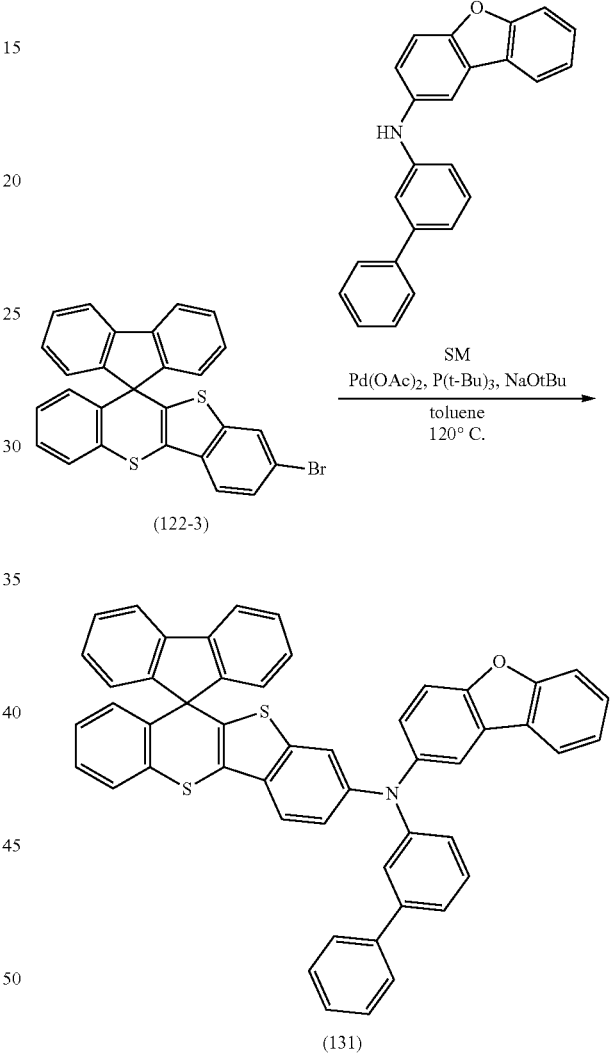

The composition 122-3 (9.7 g, 20 mmol), SM (starting material) (6.7 g, 20 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 131 (13.0 g, yield:88%).

Synthesis Example 5

Compounds 42, 46, 53 and 56

Production of Compound 42-1

[Reaction Formula 24]

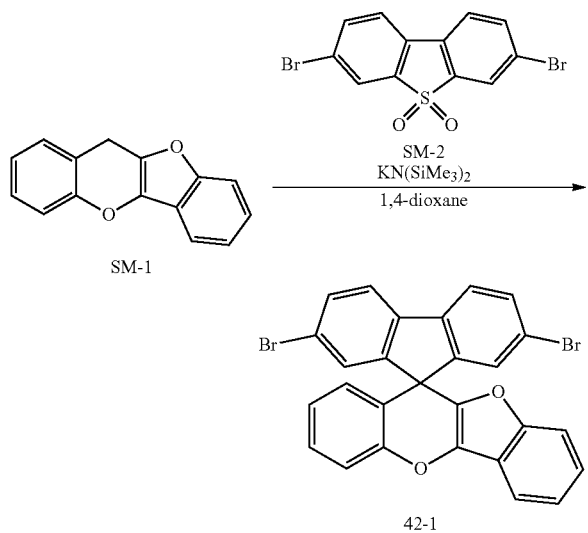

SM-1 (6.67 g, 30 mmol), SM-2 (11.2 g, 30 mmol), and KN(SiMe₃)₂ (15 g, 75 mmol) were completely dissolved into 1,4-dioxane 200 ml to form a mixture. Then, the mixture was heated and stirred while being refluxed for 16 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 42-1 (11.6 g, yield:73%).

Production of Compound 42

[Reaction Formula 25]

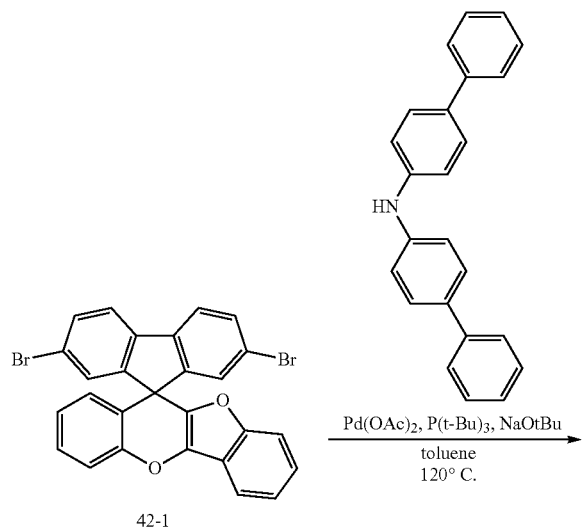

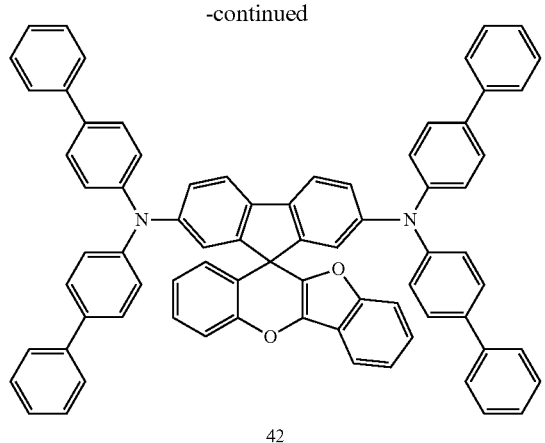

The composition 42-1 (5.3 g, 10 mmol), di([1,1'-biphenyl]-4-yl)amine (6.4 g, 20 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 42 (8.4 g, yield: 83%).

Production of Compound 46

[Reaction Formula 26]

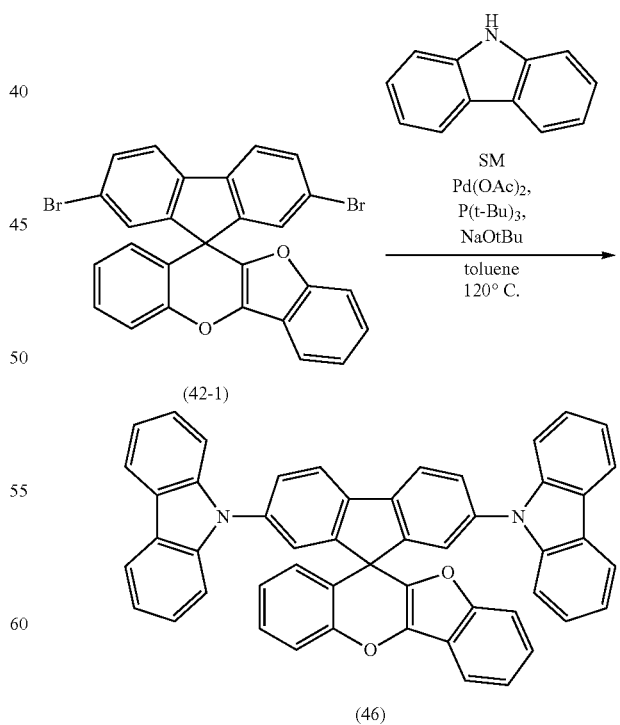

The composition 42-1 (5.3 g, 10 mmol), SM (3.3 g, 20 mmol), Pd(OAc)2 (0.45 g, 2 mmol), P(t-Bu)3 (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 46 (6.3 g, yield:89%).

Production of Compound 53-1

[Reaction Formula 27]

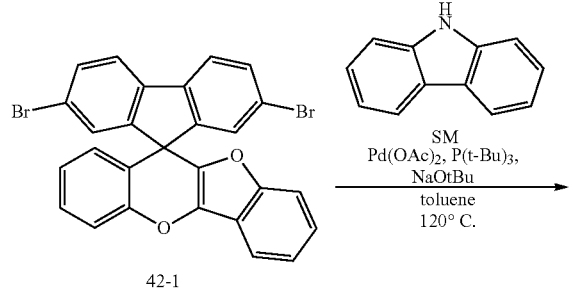

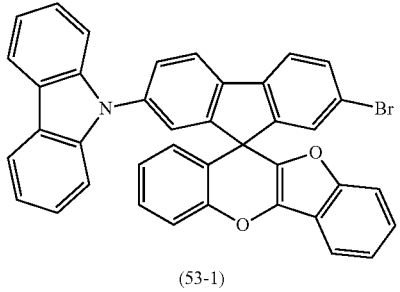

(53-1)

The Compound 42-1 (5.3 g, 10 mmol), SM (starting material) (1.7 g, 10 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 53-1 (4.6 g, yield:75%).

Production of Compound 53

[Reaction Formula 28]

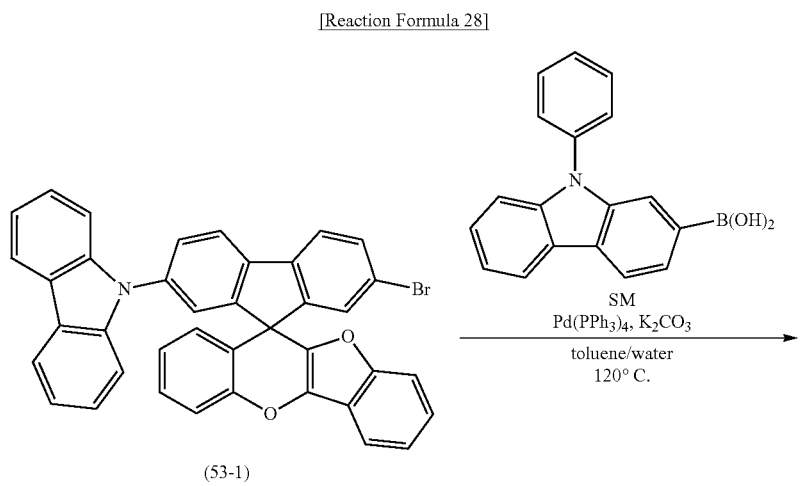

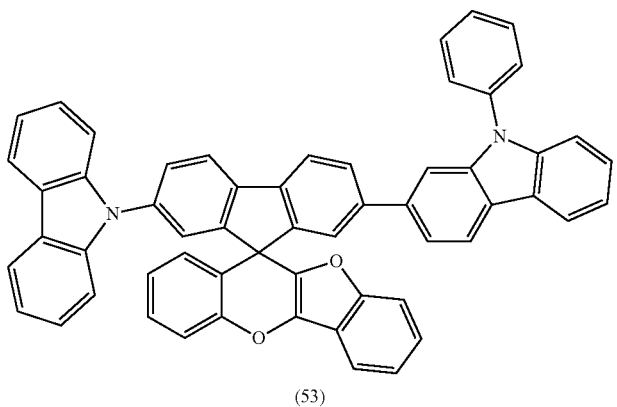

(53)

The Compound 53-1 (6.2 g, 10 mmol), SM (starting material) (2.9 g, 10 mmol), Pd(PPh$_3$)$_4$ (0.6 g, 0.5 mmol), and K$_2$CO$_3$ (4.1 g, 30 mmol) were dissolved into a mixed solution of toluene 200 ml and water 40 ml to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 53 (7.0 g, yield:90%).

Production of Compound 56

[Reaction Formula 29]

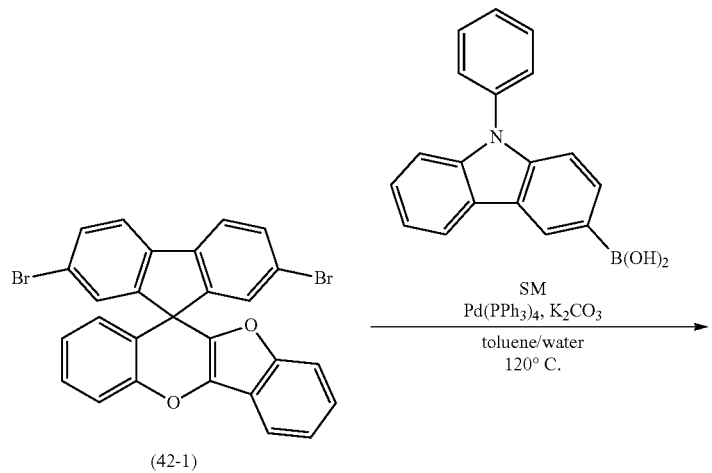

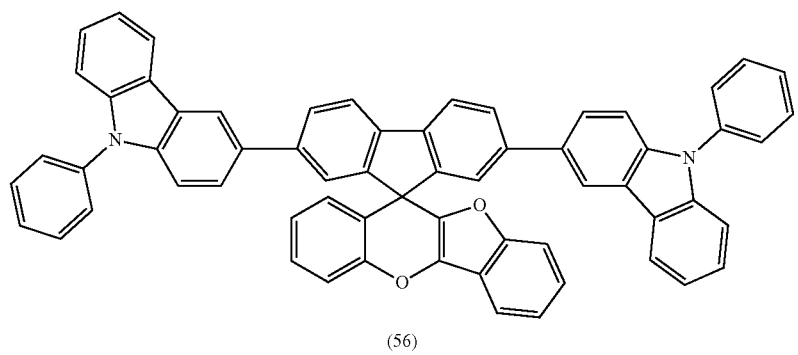

The Compound 42-1 (5.3 g, 10 mmol), SM (starting material) (5.7 g, 20 mmol), Pd(PPh$_3$)$_4$ (0.6 g, 0.5 mmol), and K$_2$CO$_3$ (4.1 g, 30 mmol) were dissolved into a mixed solution of toluene 200 ml and water 40 ml to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 56 (7.5 g, yield:88%).

Synthesis Example 6

Compounds 160 and 174

Production of Compound 160-1

[Reaction Formula 30]

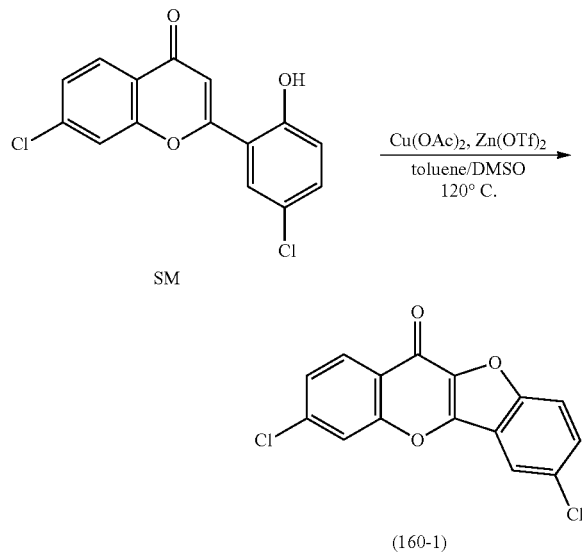

SM (starting material) (15.3 g, 50 mmol), Cu(OAc)$_2$ (10.9 g, 60 mmol), and Zn(OTf)$_2$ (3.63 g, 10 mmol) were completely dissolved into 200 ml of toluene and 50 ml of dimethylsulfoxide (DMSO) in a 500 ml round bottom flask under a nitrogen atmosphere to form a mixture. Then, the mixture was heated and stirred at 120° C. while being refluxed for 24 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 160-1 (12.2 g, yield: 80%).

Production of Compound 160-2

[Reaction Formula 31]

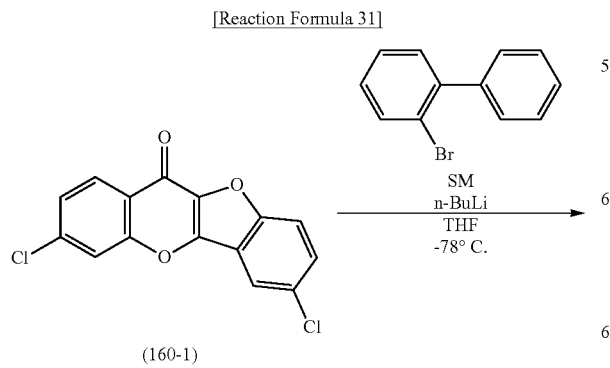

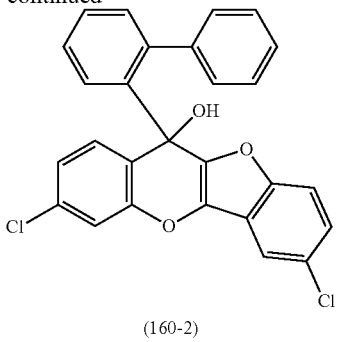

SM (starting material) (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above compound 160-1 (12.2 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 160-2 (15.6 g, yield: 85%).

Production of Compound 160-3

[Reaction Formula 32]

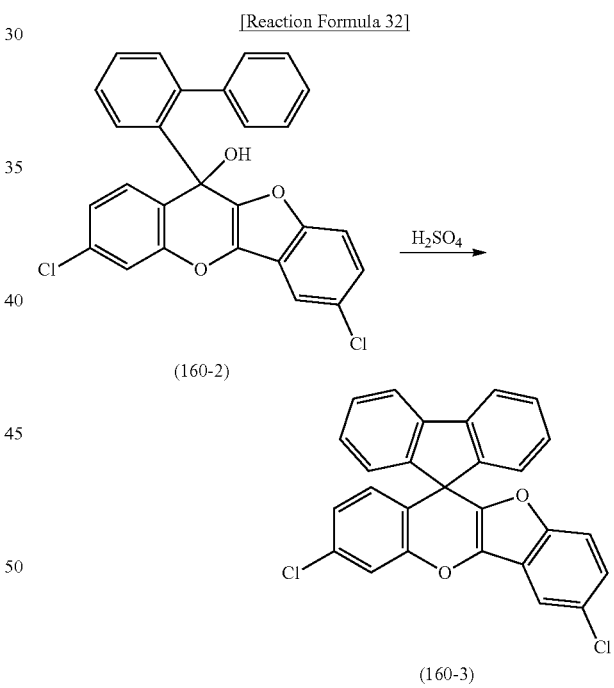

The Compound 160-2 (9.2 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 160-3 (7.2 g, yield:81%).

Production of Compound 160

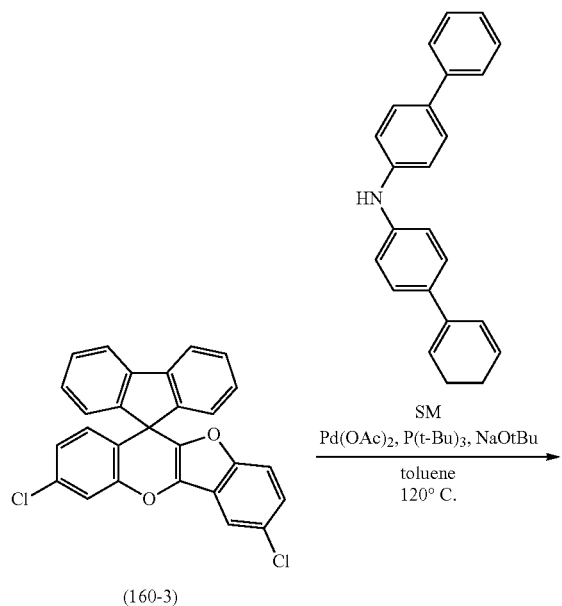

(160-3)

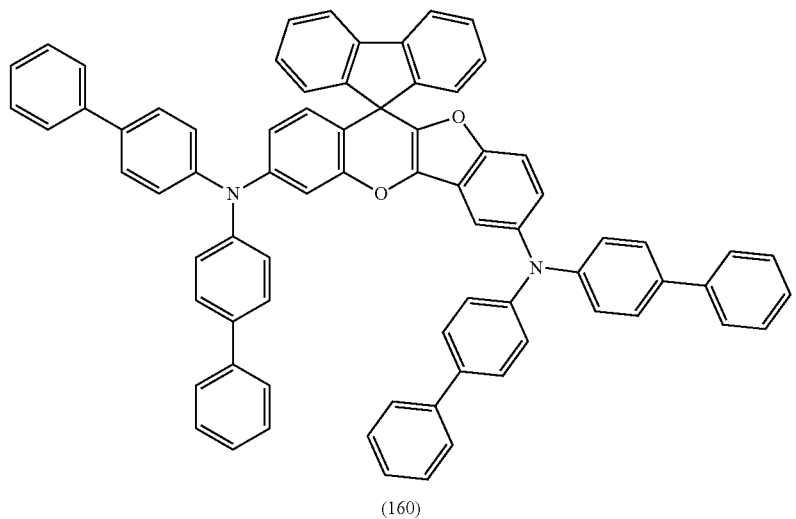

(160)

The Compound 160-3 (8.8 g, 20 mmol), SM (starting material) (12.8 g, 40 mmol), Pd(OAc)₂ (0.45 g, 2 mmol), P(t-Bu)₃ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 160 (17.6 g, yield:87%).

Production of Compound 174-1

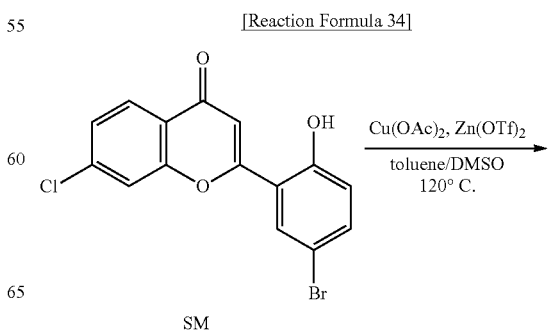

99

-continued

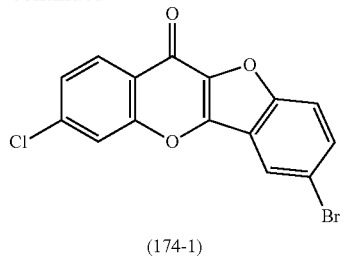

(174-1)

SM (starting material) (17.6 g, 50 mmol), Cu(OAc)₂ (10.9 g, 60 mmol), and Zn(OTf)₂ (3.63 g, 10 mmol) were completely dissolved into 200 ml of toluene and 50 ml of dimethylsulfoxide (DMSO) in a 500 ml round bottom flask under a nitrogen atmosphere to form a mixture. Then, the mixture was heated and stirred at 120° C. while being refluxed for 24 hours. After completion of the reaction of the mixture, the reacted mixture was cooled to room temperature, and was subjected to filtration. Then, precipitate was removed and was concentrated under a reduced pressure and then was subjected to column chromatography using tetrahydrofuran:hexane=1:5, to prepare Compound 174-1 (13.5 g, yield:77%).

Production of Compound 174-2

[Reaction Formula 35]

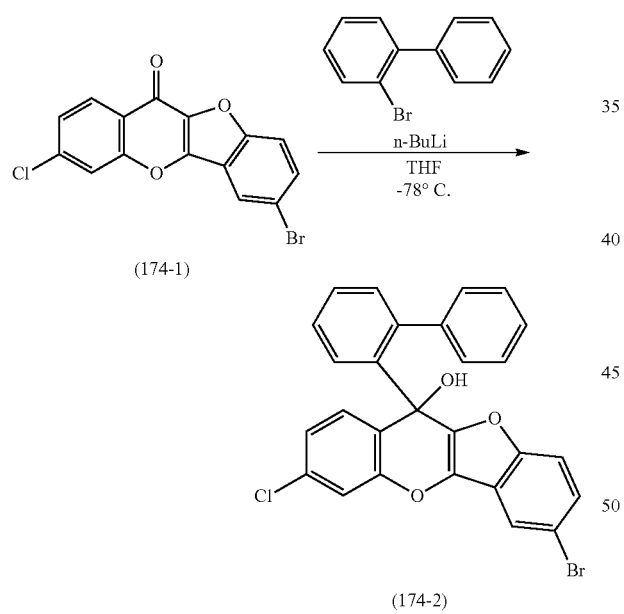

2-bromobiphenyl (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 174-1 (14.0 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 174-2 (16.1 g, yield: 80%).

100

Production of Compound 174-3

[Reaction Formula 36]

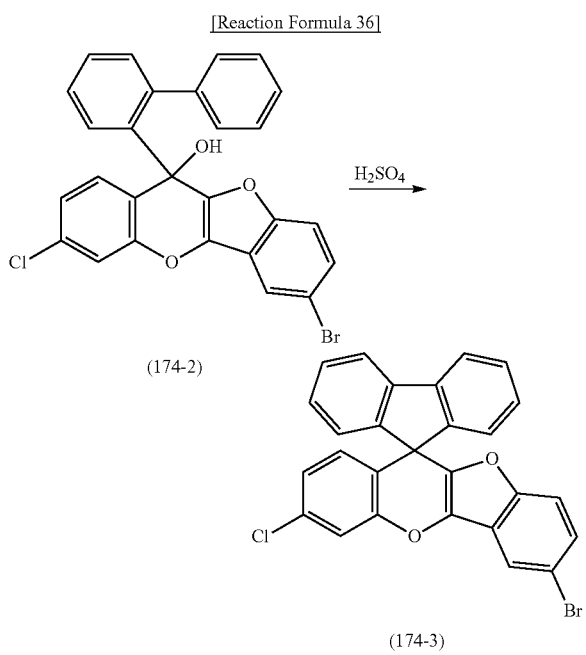

The Compound 174-2 (10.0 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 174-3 (8.6 g, yield: 88%).

Production of Compound 174-4

[Reaction Formula 37]

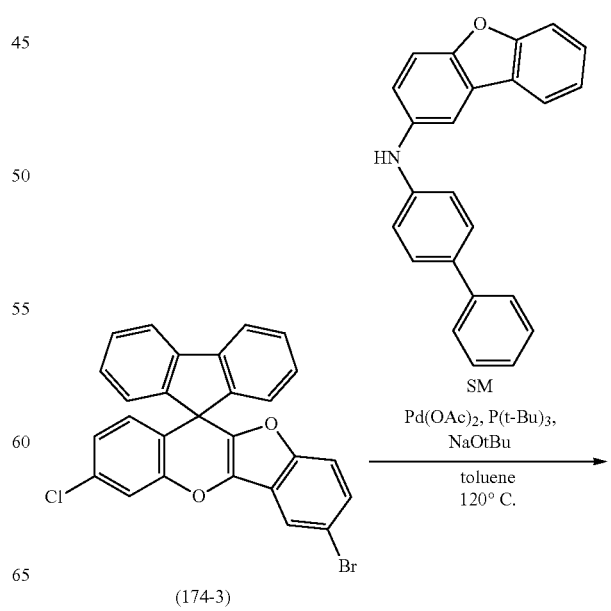

-continued

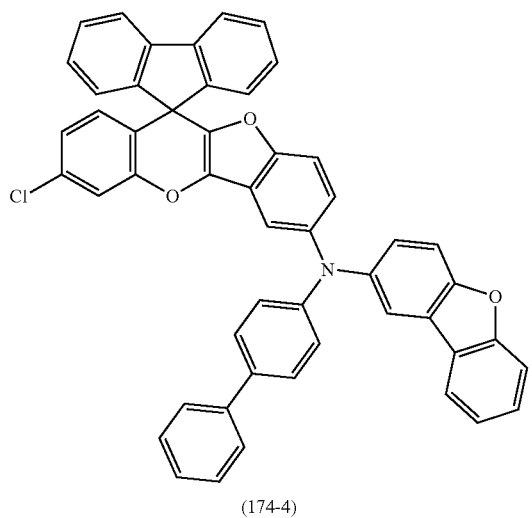

(174-4)

The Compound 174-3 (9.7 g, 20 mmol), SM (starting material) (6.7 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 174-4 (11.7 g, yield:79%).

Production of Compound 174

[Reaction Formula 38]

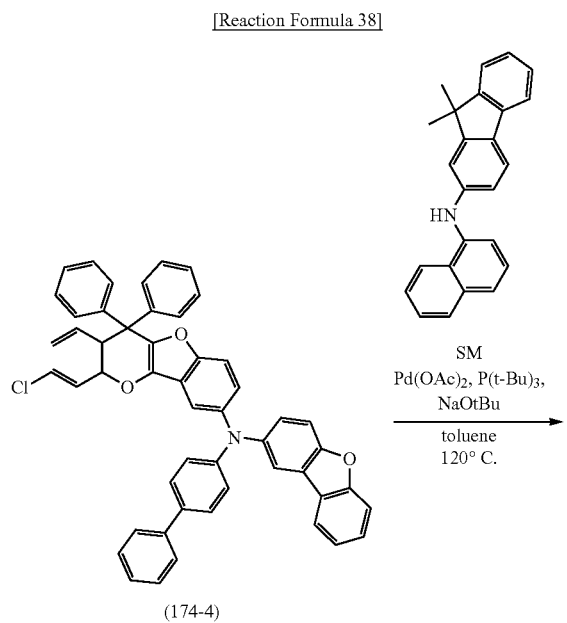

(174-4)

-continued

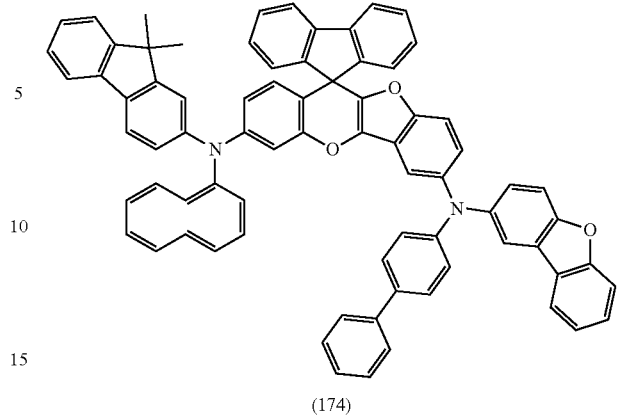

(174)

The Compound 174-4 (14.8 g, 20 mmol), SM (starting material) (6.7 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 24 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 174 (15.2 g, yield:73%).

Synthesis Example 7

Compound 80

Production of Compound 80-1

[Reaction Formula 39]

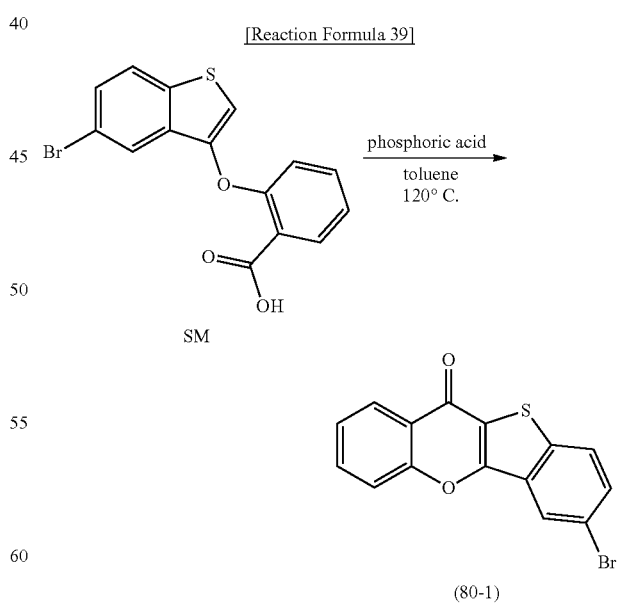

(80-1)

SM (starting material) (7.0 g, 20 mmol), and phosphoric acid (1.0 g, 10 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 80-1 (5.4 g, yield:82%).

Production of Compound 80-2

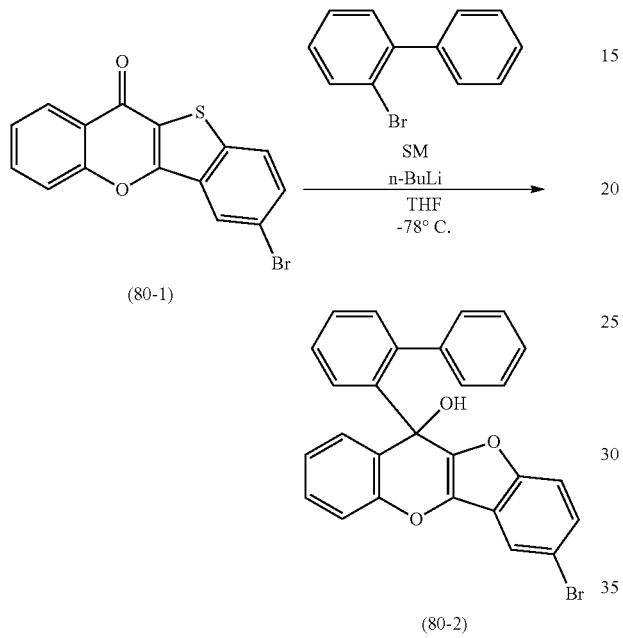

2-bromobiphenyl (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 122-1 (13.9 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 80-2 (14.6 g, yield: 78%).

Production of Compound 80-3

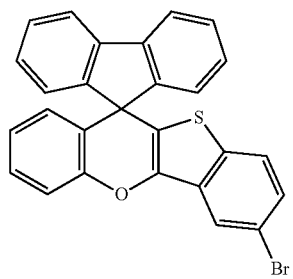

The Compound 80-2 (9.7 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 80-3 (8.4 g, yield:90%).

Production of Compound 80

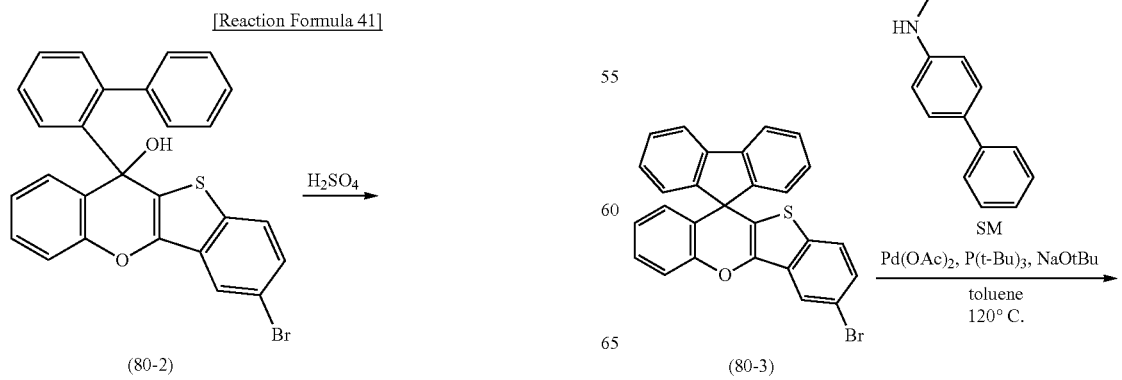

-continued

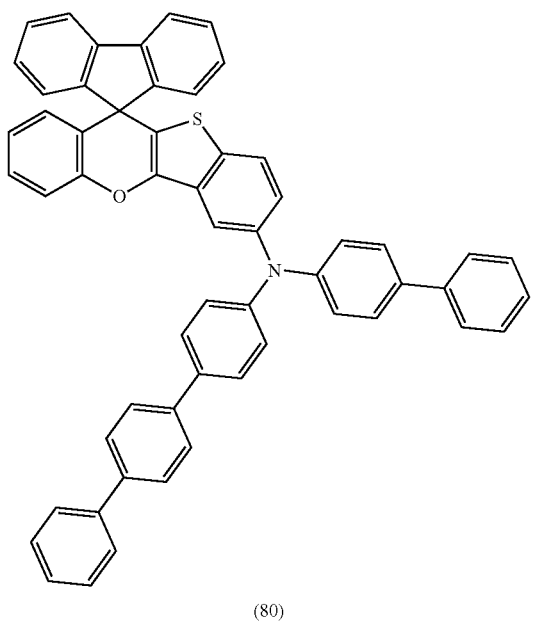

(80)

The Compound 80-3 (9.3 g, 20 mmol), SM (starting material) (8.0 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 24 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 80 (12.5 g, yield:80%).

Synthesis Example 8

Compound 92

Production of Compound 92-1

[Reaction Formula 43]

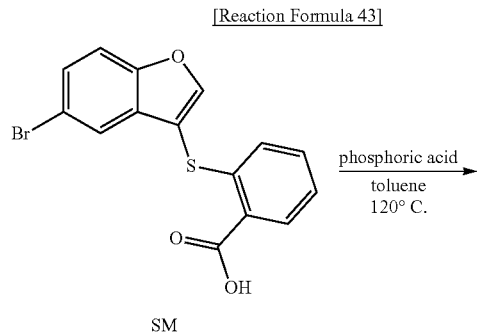

SM

-continued

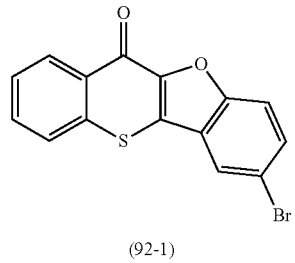

(92-1)

SM (starting material) (7.0 g, 20 mmol) and phosphoric acid (1.0 g, 10 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 92-1 (5.3 g, yield:80%).

Production of Compound 92-2

[Reaction Formula 44]

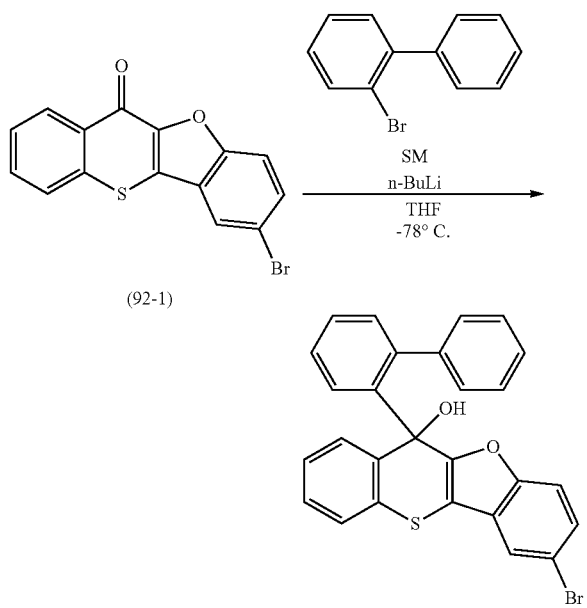

2-bromobiphenyl (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 92-1 (13.2 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 92-2 (14.7 g, yield: 76%).

Production of Compound 92-3

[Reaction Formula 45]

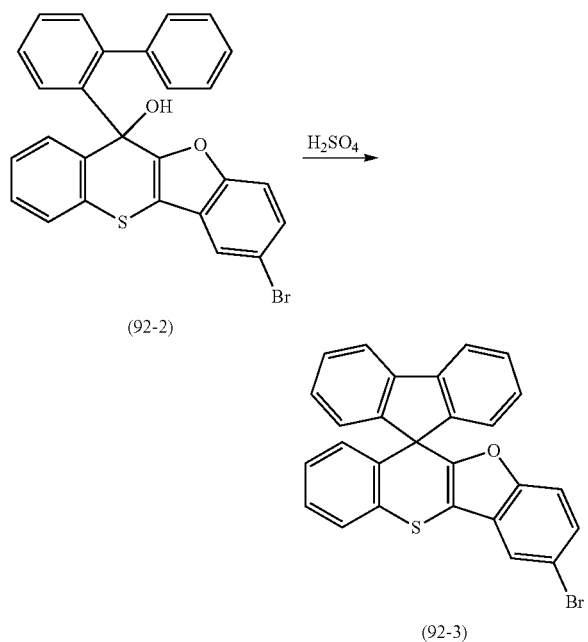

The Compound 92-2 (9.7 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 92-3 (8.7 g, yield:93%).

Production of Compound 92

[Reaction Formula 46]

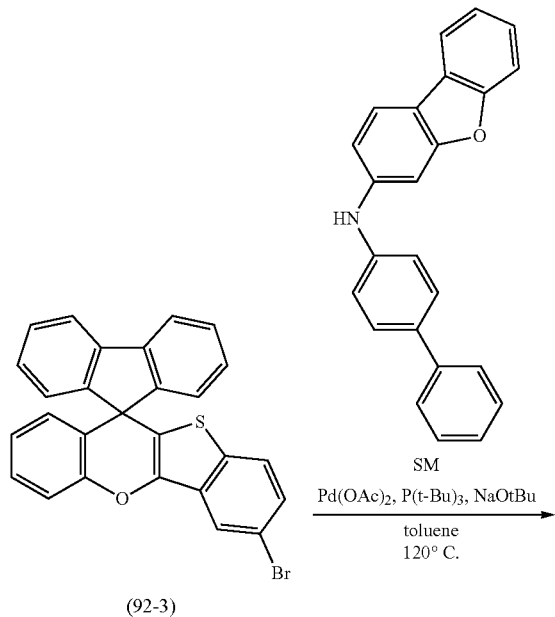

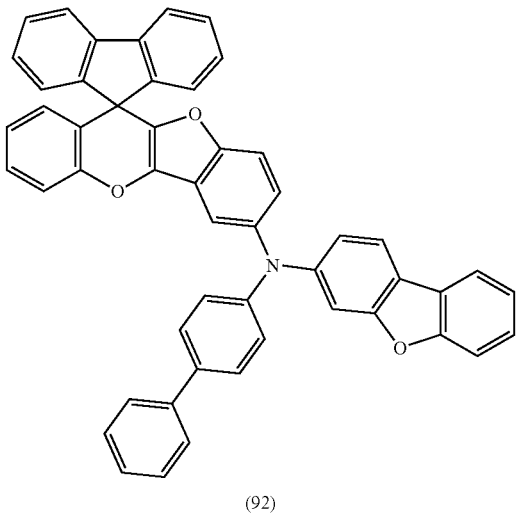

The Compound 92-3 (9.3 g, 20 mmol), SM (starting material) (6.7 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 24 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 92 (12.0 g, yield:85%).

Synthesis Example 9

Compound 120

Production of Compound 120-1

[Reaction Formula 47]

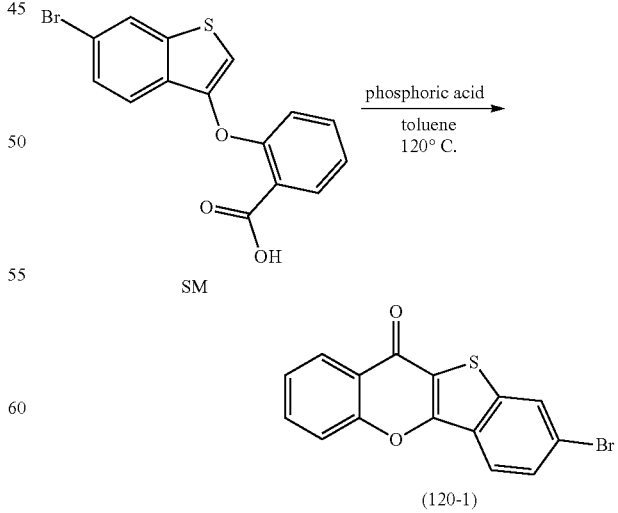

The above SM (starting material) (7.0 g, 20 mmol), and phosphoric acid (1.0 g, 10 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 120-1 (5.5 g, yield:80%).

Production of Compound 120-2

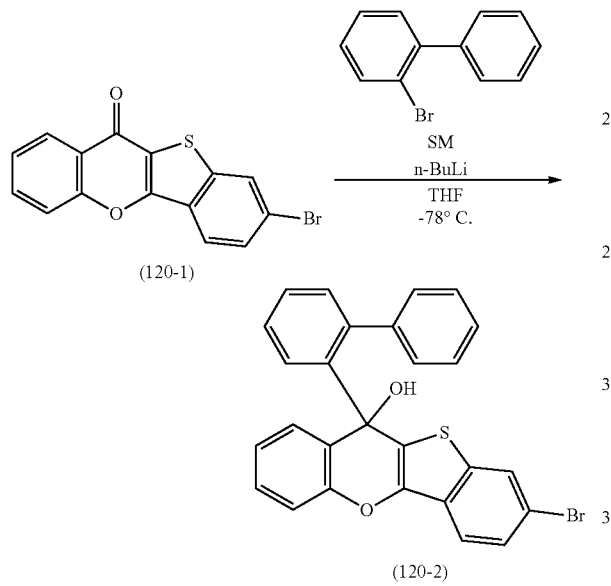

2-bromobiphenyl (9.3 g, 40 mmol) was dissolved in tetrahydrofuran (100 ml) in a nitrogen atmosphere and then cooled to −78° C. Then, n-BuLi (2.5 M, 16 ml, 40 mmol) was slowly added dropwise thereto, followed by stirring for 1 hour. The above Compound 120-1 (13.2 g, 40 mmol) was slowly added dropwise thereto, stirred for 3 hours, then raised to room temperature. Water (100 ml) was added thereto. Extraction was performed with tetrahydrofuran. A resulting organic layer was concentrated and recrystallized using methanol to obtain Compound 120-2 (15.0 g, yield: 77%).

Production of Compound 120-3

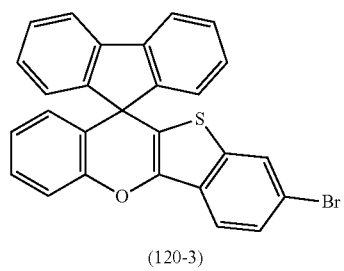

The Compound 120-2 (9.7 g, 20 mmol) was dissolved in 100 ml of acetic acid in a nitrogen atmosphere. Then, 20 ml of anhydrous sulfuric acid was added thereto. Then, the mixture was heated and stirred while refluxed for 3 hours. After completion of the reaction, the reacted mixture was cooled to room temperature, was subjected to extraction using chloroform, and washed with water. Then, water was removed from the washed extracted product using anhydrous magnesium sulfate which in turn was filtered. Then, an organic solvent was distilled under a reduced pressure and was removed from the extracted product, to obtain Compound 120-3 (8.6 g, yield:92%).

Production of Compound 120

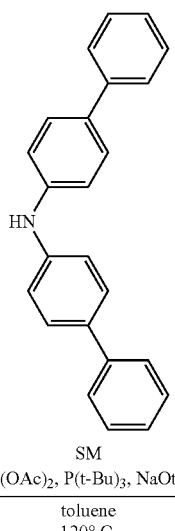

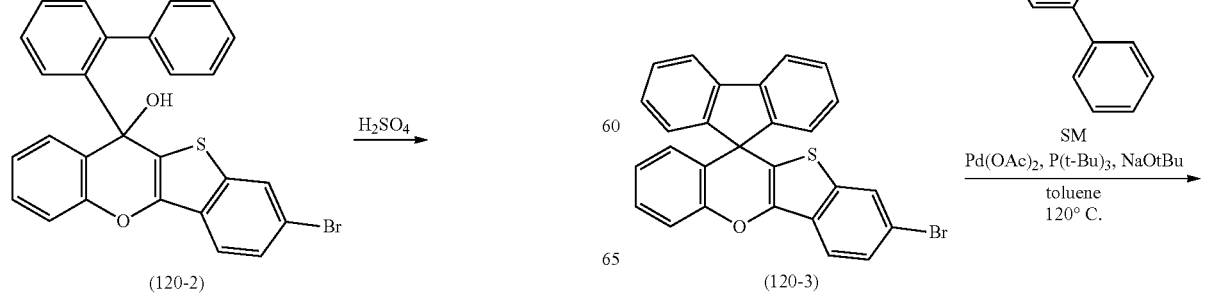

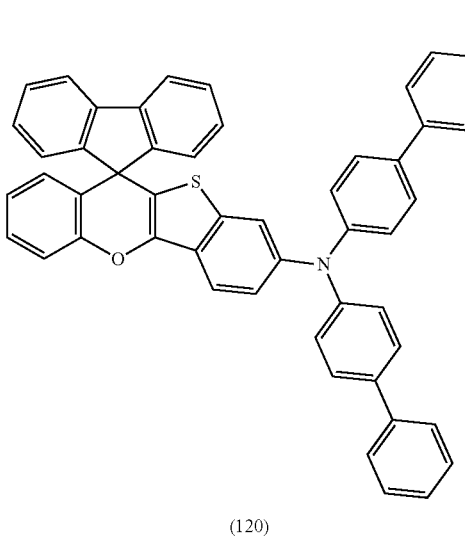

(120)

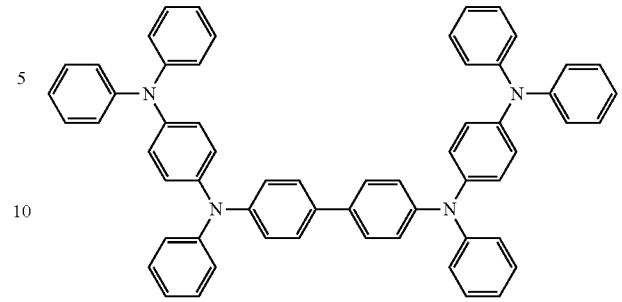

HI-1

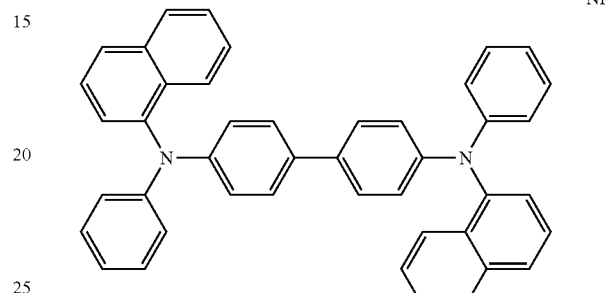

NPB

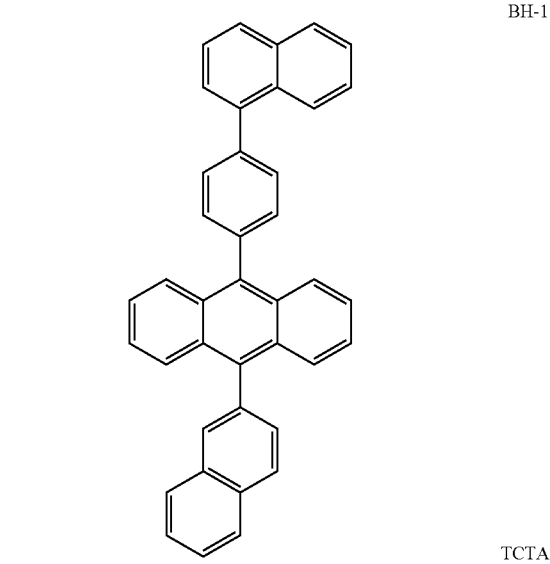

BH-1

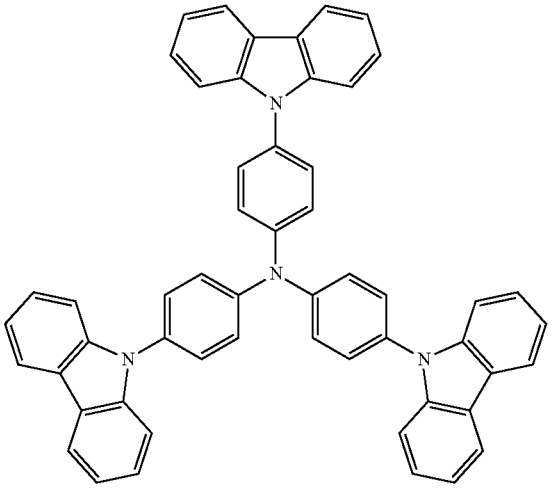

TCTA

The Compound 120-3 (9.3 g, 20 mmol), SM (starting material) (8.0 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 24 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, to obtain Compound 120 (12.2 g, yield:86%).

Example 1

After cleaning a glass substrate having an ITO (indium tin oxide) thin film coated thereon to a thickness of 1,000 Å, the substrate was ultrasonically washed with a solvent such as isopropyl alcohol, acetone, or methanol and was dried. Then, HI-1 as a hole injection material was deposited to a thickness of 60 nm on the ITO transparent electrode via thermal vacuum deposition. Then, Compound 3 as defined above as a hole transport material was thermally vacuum deposited to 80 nm thickness on the hole injection material. Subsequently, BH-1 and BD-1 were used as a host material and a dopant material (5 wt %) in a light-emitting layer respectively. Thus, the host material BH-1 was thermally vacuum-deposited to a thickness of 30 nm on the hole transport material while the dopants BD-1 were doped into the host material, thus forming the light-emitting layer. Then, ET-1:Liq (1:1 weight ratio) compounds as electron transport layer material:electron injection layer material respectively were thermally vacuum deposited at 30 nm thickness on the light-emitting layer. Then, aluminum as cathode material was deposited at a thickness of 100 nm on the electron injection layer resulting in an organic light-emitting device.

-continued

BD-1

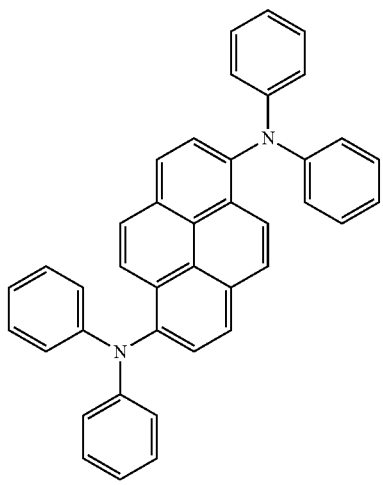

ET-1

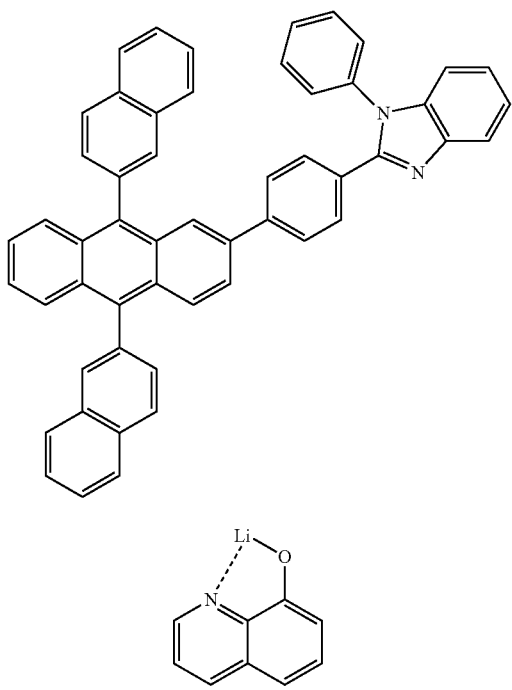

Liq

Examples 2 to 13

Organic light-emitting devices were fabricated in the same manner as in Example 1 except that compounds shown in Table 1 below were used in place of Compound 3 of Example 1.

Comparative Example 1

An organic light-emitting device was fabricated in the same manner as in Example 1 except that NPB compound was used instead of Compound 3 of Example 1.

Example 14

After cleaning a glass substrate having an ITO (indium tin oxide) thin film coated thereon to a thickness of 1,000 Å, the substrate was ultrasonically washed with a solvent such as isopropyl alcohol, acetone, or methanol and was dried. Then, HI-1 as a hole injection material was deposited to a thickness of 60 nm on the ITO transparent electrode via thermal vacuum deposition. Then, the NPB as defined above as a hole transport material was thermally vacuum deposited to 80 nm thickness on the hole injection material. Subsequently, the BH-1 and Compound 42 as defined above were used as a host material and a dopant material (5 wt %) in a light-emitting layer respectively. Thus, the host material BH-1 was thermally vacuum-deposited to a thickness of 30 nm on the hole transport material while the dopants made of Compound 42 as defined above were doped into the host material, thus forming the light-emitting layer. Then, ET-1: Liq (1:1 weight ratio) compounds as electron transport layer material:electron injection layer material respectively were thermally vacuum deposited at 30 nm thickness on the light-emitting layer. Then, aluminum as a cathode material was deposited at a thickness of 100 nm on the electron injection layer resulting in an organic light-emitting device.

Example 15

An organic light-emitting device was fabricated in the same manner as in Example 14 except that Compound 160 was used in place of Compound 42 of Example 14.

Example 16

An organic light-emitting device was fabricated in the same manner as in Example 14 except that Compound 174 was used in place of Compound 42 of Example 14.

Comparative Example 2

An organic light-emitting device was fabricated in the same manner as in Example 14 except that the BD-1 compound was used instead of Compound 42 of Example 14.

Example 17

After cleaning a glass substrate having an ITO (indium tin oxide) thin film coated thereon to a thickness of 1,000 Å, the substrate was ultrasonically washed with a solvent such as isopropyl alcohol, acetone, or methanol and was dried. Then, HI-1 as a hole injection material was deposited to a thickness of 60 nm on the ITO transparent electrode via thermal vacuum deposition. Then, the NPB compound as defined above as a hole transport material was thermally vacuum deposited to 80 nm thickness on the hole injection material. Subsequently, Compound 46 as defined above was thermally vacuum deposited to a thickness of 10 nm as an electron blocking layer material on the hole transport material layer. Subsequently, BH-1 and BD-1 were used as a host material and a dopant material (5 wt %) in a light-emitting layer respectively. Thus, the host material BH-1 was thermally vacuum-deposited to a thickness of 30 nm on the hole transport material while the dopants BD-1 were doped into the host material, thus forming the light-emitting layer. Then, ET-1:Liq (1:1 weight ratio) compounds as electron transport layer material:electron injection layer material respectively were thermally vacuum deposited at 30 nm thickness on the light-emitting layer. Then, aluminum as cathode material was deposited at a thickness of 100 nm on the electron injection layer resulting in an organic light-emitting device.

Example 18

An organic light-emitting device was fabricated in the same manner as in Example 17 except that Compound 53 was used in place of Compound 46 of Example 17.

Example 19

An organic light-emitting device was fabricated in the same manner as in Example 17 except that Compound 56 was used in place of Compound 46 of Example 17.

Comparative Example 3

An organic light-emitting device was fabricated in the same manner as in Example 17 except that the TCTA compound was used instead of Compound 46 of Example 17.

Experimental Example 1

Evaluation of Characteristics of Organic Light-Emission Device

The devices as fabricated in Examples 1 to 13 and Comparative Example 1 were evaluated in terms of device characteristics at room temperature using a current source (KEITHLEY) and a photometer (PR 650). Table 1 below shows a driving voltage (V), current density (mA/cm$^2$), luminance-current efficiency (Cd/A), and power efficiency (lm/w), CIE color coordinate measurements, and life-span characteristics as measured for the devices as fabricated in Examples 1 to 13 and Comparative Example 1. The life-span characteristics were measured using a time (LT95) (hr) consumed for a current luminance to reach 95% of an initial luminance.

TABLE 1

| Examples | Op. V | mA/cm$^2$ | Cd/A | lm/w | CIEx | CIEy | LT95 (hr) |
|---|---|---|---|---|---|---|---|
| Comparative Example 1 | 4.58 | 8.9 | 6.13 | 4.59 | 0.141 | 0.110 | 156 |
| Example 1 [Compound 3] | 4.22 | 9.9 | 6.64 | 5.03 | 0.141 | 0.112 | 179 |
| Example 2 [Compound 15] | 4.12 | 9.8 | 6.67 | 5.24 | 0.140 | 0.110 | 166 |
| Example 3 [Compound 26] | 4.06 | 9.9 | 6.69 | 5.63 | 0.139 | 0.111 | 167 |
| Example 4 [Compound 61] | 3.97 | 10 | 6.61 | 5.45 | 0.140 | 0.110 | 174 |
| Example 5 [Compound 72] | 4.02 | 10 | 6.67 | 5.34 | 0.141 | 0.112 | 170 |
| Example 6 [Compound 80] | 3.94 | 10 | 6.54 | 5.81 | 0.140 | 0.113 | 179 |
| Example 7 [Compound 92] | 4.08 | 9.9 | 6.53 | 5.11 | 0.141 | 0.111 | 168 |
| Example 8 [Compound 100] | 4.09 | 9.9 | 6.59 | 5.53 | 0.139 | 0.110 | 173 |
| Example 9 [Compound 102] | 4.11 | 9.9 | 6.56 | 5.56 | 0.139 | 0.110 | 179 |
| Example 10 [Compound 111] | 3.99 | 10 | 6.62 | 5.51 | 0.140 | 0.110 | 179 |
| Example 11 [Compound 120] | 4.02 | 9.8 | 6.46 | 5.44 | 0.139 | 0.110 | 170 |
| Example 12 [Compound 122] | 4.10 | 9.9 | 6.53 | 5.59 | 0.140 | 0.110 | 176 |
| Example 13 [Compound 131] | 4.06 | 9.9 | 6.56 | 5.47 | 0.140 | 0.111 | 171 |

Experimental Example 2

Evaluation of Characteristics of Organic Light-Emission Device

The devices as fabricated in Examples 14 to 16 and Comparative Example 2 were evaluated in terms of device characteristics at room temperature using a current source (KEITHLEY) and a photometer (PR 650). Table 2 below shows a driving voltage (V), current density (mA/cm$^2$), luminance-current efficiency (Cd/A), and power efficiency (lm/w), CIE color coordinate measurements, and life-span characteristics as measured for the devices as fabricated in Examples 14 to 16 and Comparative Example 2. The life-span characteristics were measured using a time (LT95) (hr) consumed for a current luminance to reach 95% of an initial luminance.

TABLE 2

| Examples | Op. V | mA/cm$^2$ | Cd/A | CIEx | CIEy |
|---|---|---|---|---|---|
| Comparative Example 2 | 4.33 | 10 | 5.6 | 0.143 | 0.131 |
| Example 14 [Compound 42] | 3.98 | 10 | 7.2 | 0.141 | 0.110 |
| Example 15 [Compound 160] | 3.86 | 10 | 7.7 | 0.137 | 0.111 |
| Example 16 [Compound 174] | 3.89 | 10 | 7.8 | 0.139 | 0.110 |

Experimental Example 3

Evaluation of Characteristics of Organic Light-Emission Device

The devices as fabricated in Examples 17 to 19 and Comparative Example 3 were evaluated in terms of device characteristics at room temperature using a current source (KEITHLEY) and a photometer (PR 650). Table 3 below shows a driving voltage (V), current density (mA/cm$^2$), luminance-current efficiency (Cd/A), and power efficiency (lm/w), CIE color coordinate measurements, and life-span characteristics as measured for the devices as fabricated in Examples 17 to 19 and Comparative Example 3. The life-span characteristics were measured using a time (LT95) (hr) consumed for a current luminance to reach 95% of an initial luminance.

TABLE 2

| Examples | Op. V | mA/cm$^2$ | Cd/A | lm/w | CIEx | CIEy | LT95 (hr) |
|---|---|---|---|---|---|---|---|
| Comparative Example 3 | 4.58 | 8.9 | 6.13 | 4.59 | 0.141 | 0.110 | 156 |
| Example 17 [Compound 46] | 4.49 | 9.9 | 7.74 | 6.33 | 0.140 | 0.110 | 170 |
| Example 18 [Compound 53] | 4.43 | 9.8 | 7.96 | 6.64 | 0.141 | 0.110 | 176 |
| Example 19 [Compound 56] | 4.46 | 9.9 | 7.90 | 6.61 | 0.140 | 0.112 | 173 |

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is apparent that a predictable effect resulting from the features of the present disclosure should be recognized.

What is claimed is:

1. A compound represented by Chemical Formula 1:

[Chemical Formula 1]

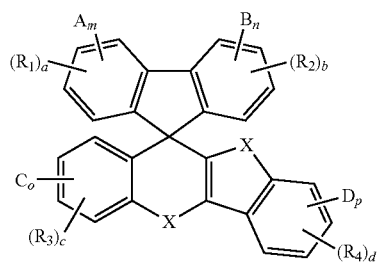

wherein, in the Chemical Formula 1, each of $R_1$ to $R_4$ independently represents one selected from a group consisting of hydrogen, deuterium, halogen, a substituted or unsubstituted C1 to C30 alkyl group, a substituted or unsubstituted C6 to C30 aryl group, a substituted or unsubstituted C2 to C60 heteroaryl group, a substituted or unsubstituted C3 to C30 cycloalkyl group, a C1 to C30 alkoxy group and a C6 to C30 aryloxy group;

each of a and b independently denotes an integer of 0 to 4, wherein when a or b denotes an integer of 2 or greater, each $R_1$ is the same or different and each $R_2$ is the same or different, each of c and d independently denotes an integer of 0 to 4, wherein when c or d denotes an integer of 2 or greater, each $R_3$ is the same or different and each $R_4$ is the same or different, each of m and n independently denotes an integer of 0 to 4, wherein when m or n denotes an integer of 2 or greater, each A is the same or different and each B is the same or different, each of o and p independently denotes an integer of 0 to 4, wherein when o or p denotes an integer of 2 or greater, each C is the same or different and each D is the same or different, wherein 0≤a+m≤4, 0≤b+n≤4, 0≤c+o≤4 and 0≤d+p≤4;

X represents O or S; and each of A to D is represented by Chemical Formula 2:

[Chemical Formula 2]

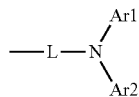

wherein, in the Chemical Formula 2, L represents a direct bond or represents one selected from a group consisting of a substituted or unsubstituted C1 to C10 alkylene group, a substituted or unsubstituted C6 to C30 arylene group or a divalent group of a heteroaromatic ring having 6 to 30 aromatic ring atoms; and each of $Ar_1$ and $Ar_2$ independently represents one selected from a group consisting of a substituted or unsubstituted C6 to C60 aryl group or a monovalent group of a heteroaromatic ring having 6 to 60 aromatic ring atoms, wherein $Ar_1$ and $Ar_2$ are optionally bonded to each other to form a ring.

2. The compound of claim 1, wherein each of $Ar_1$ and $Ar_2$ in the Chemical Formula 2 are independently selected from:

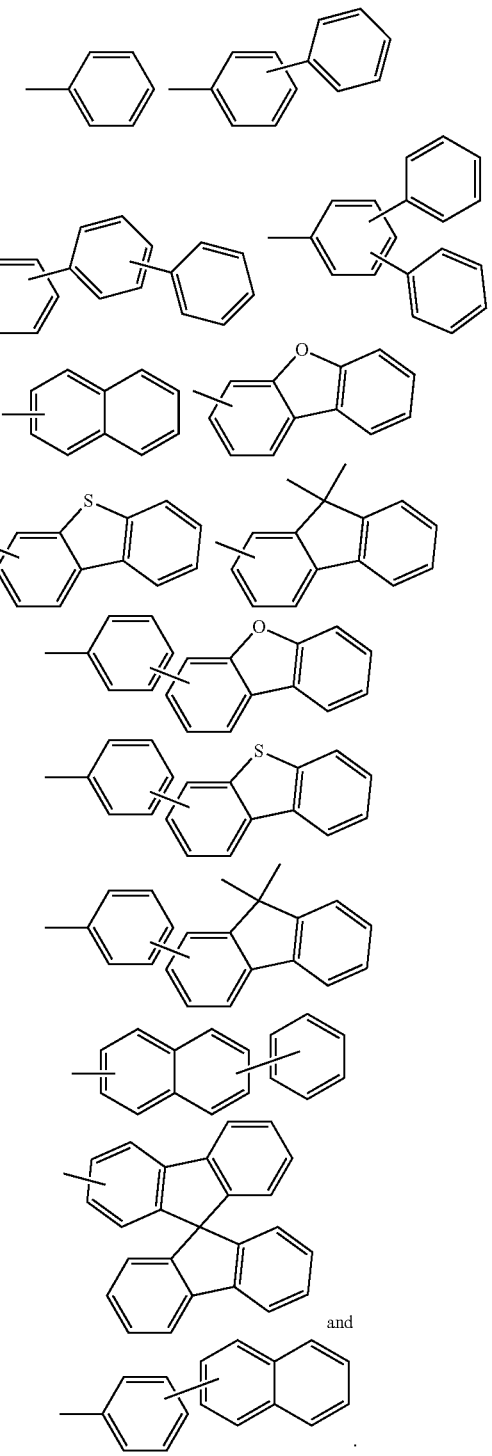

3. The compound of claim 1, wherein the compound represented by Chemical Formula 1 is represented by one of following Chemical Formulas:

1
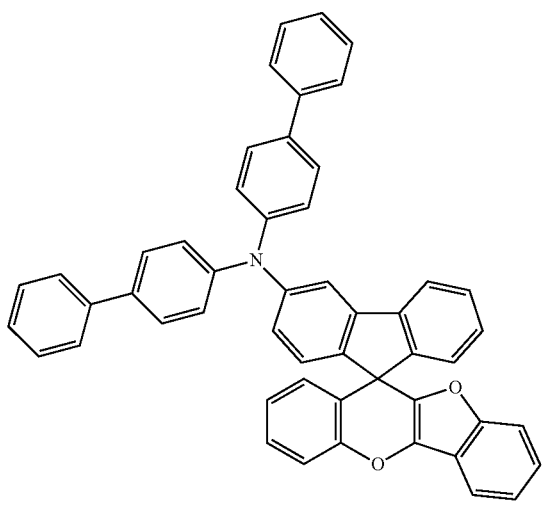
2
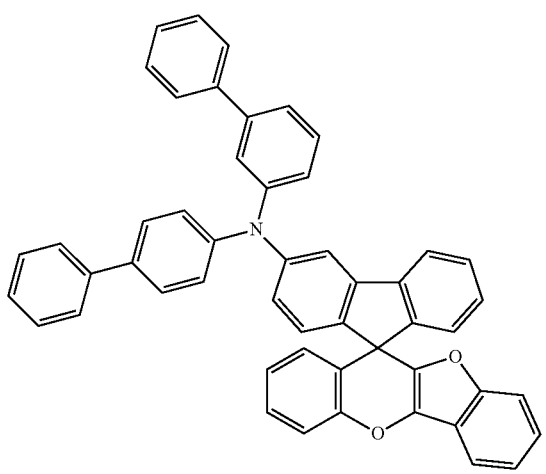
3
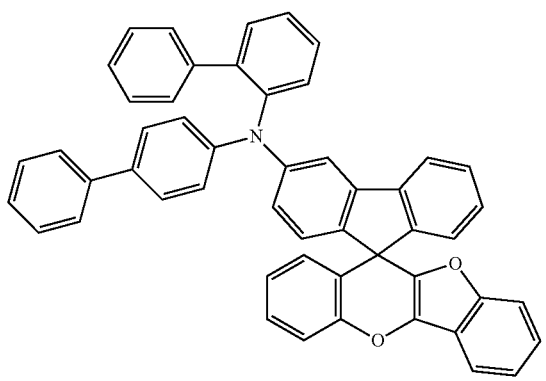
4
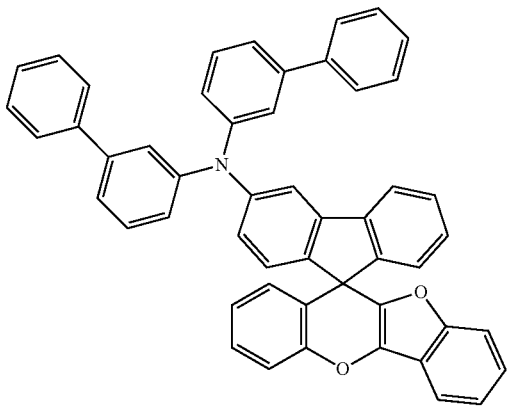
5
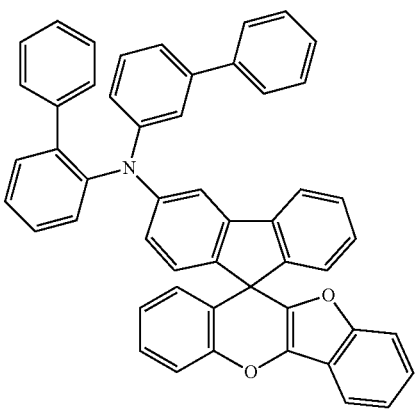
6
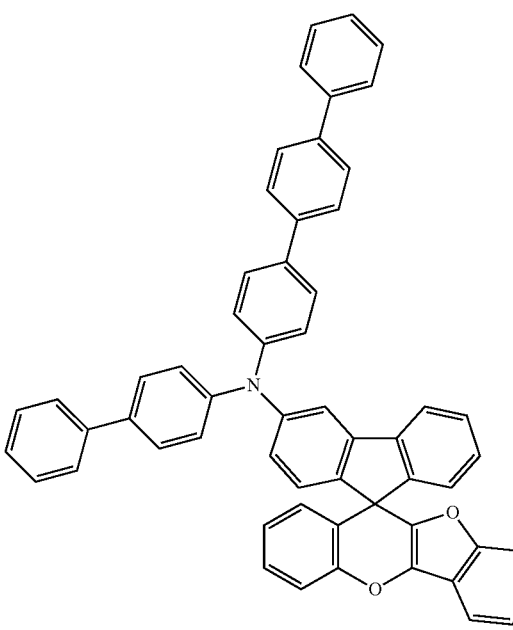

121
-continued
7
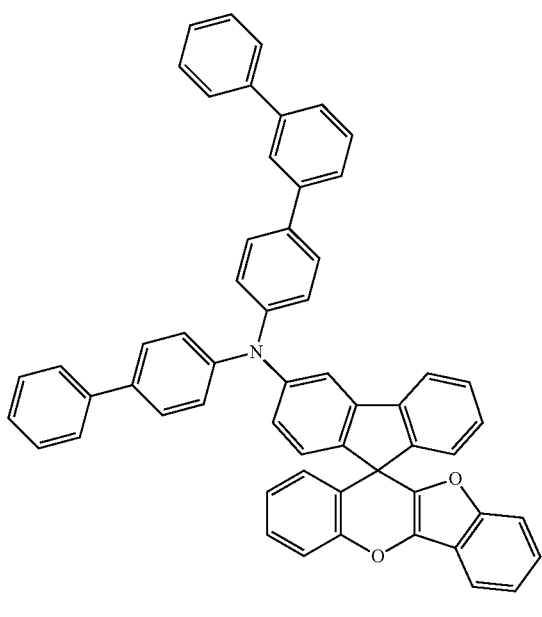
8
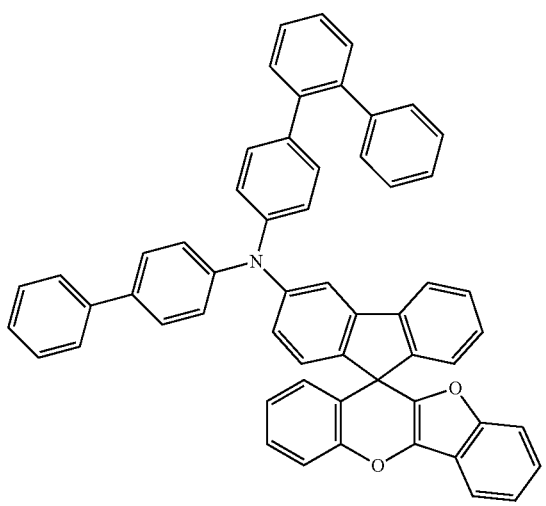
9
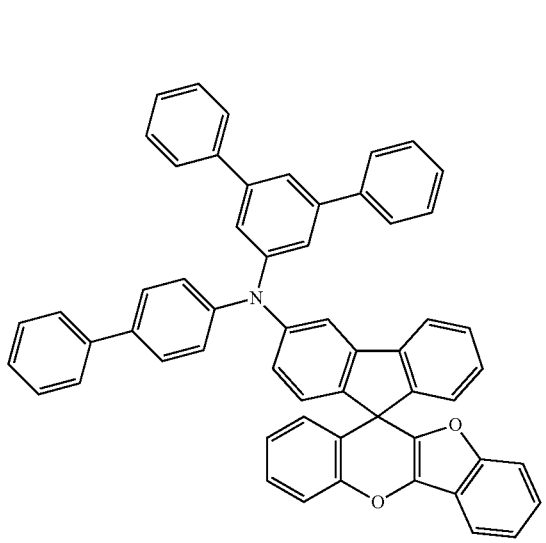
122
-continued
10
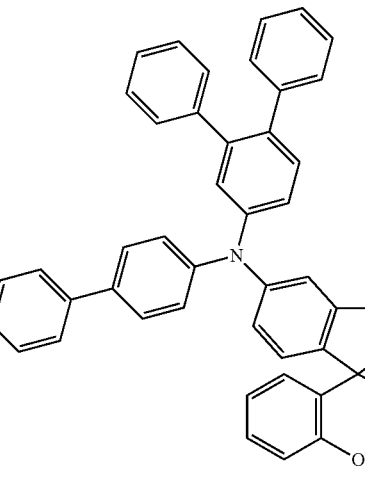
11
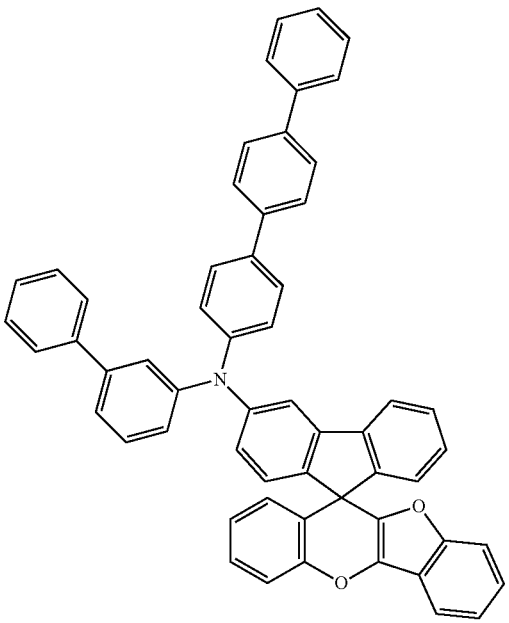
12
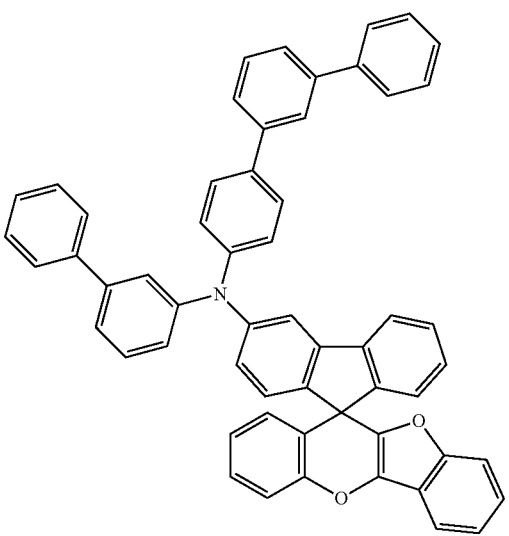

| 13 | | 16 |
|---|---|---|
| 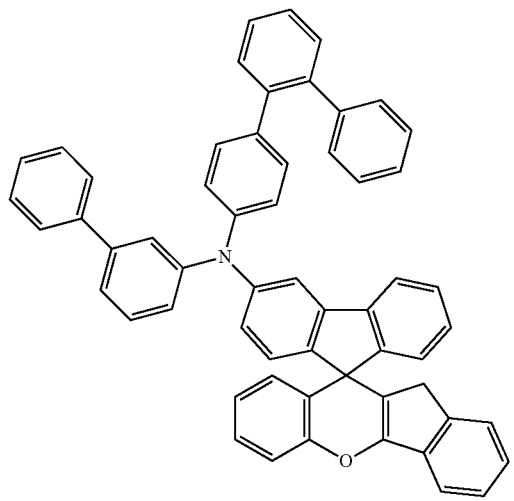 | | 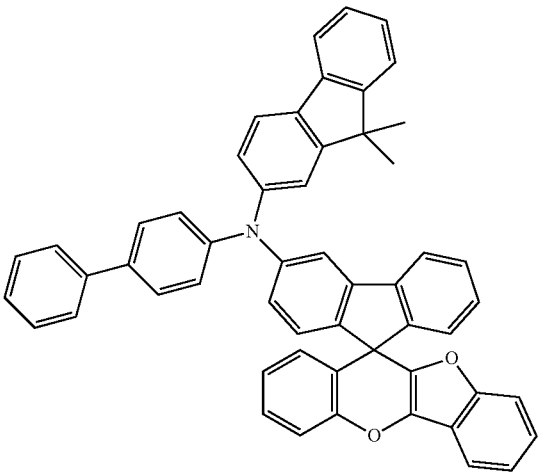 |
| 14 | | 17 |
| 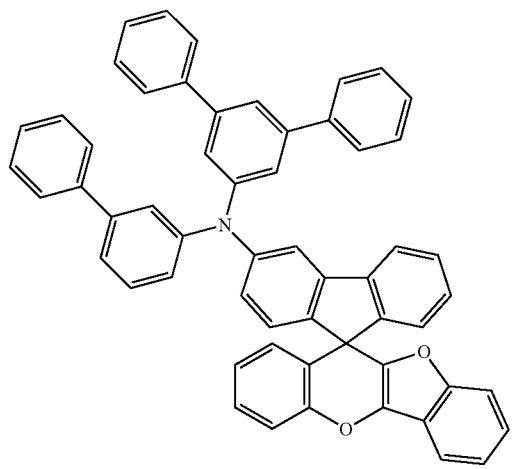 | | 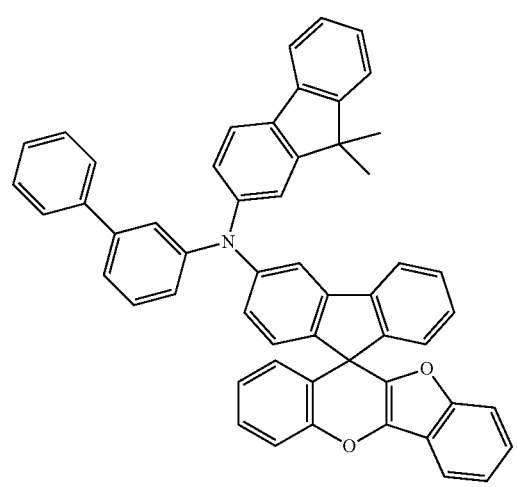 |
| 15 | | 18 |
| 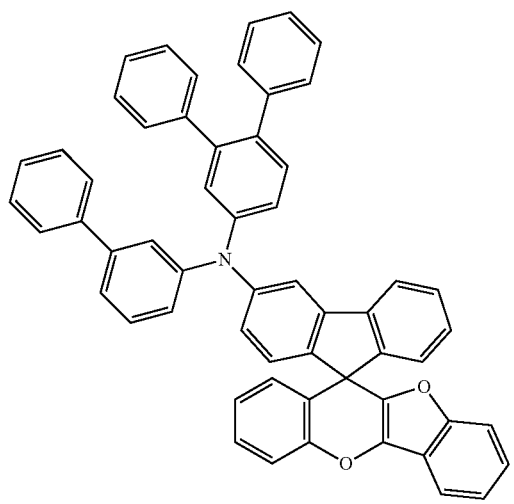 | | 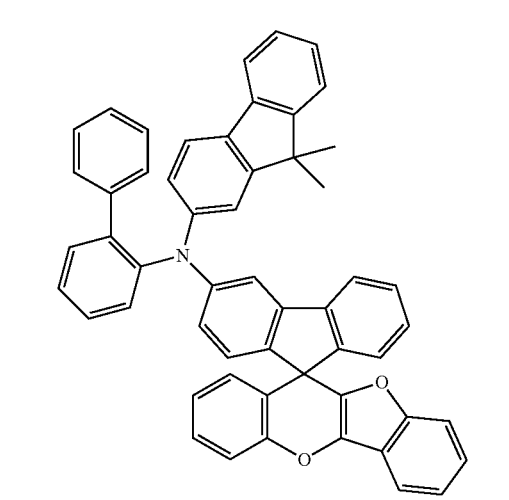 |

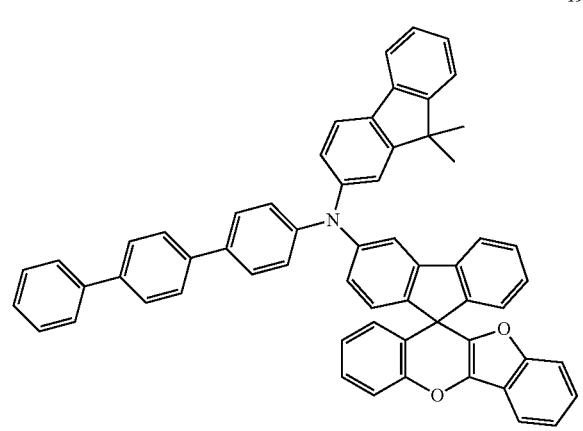
19
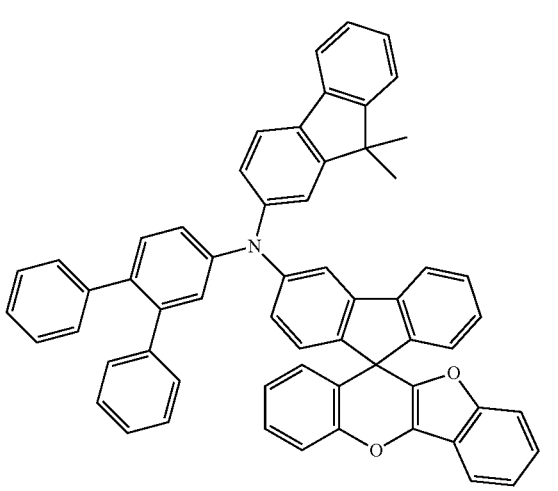
22
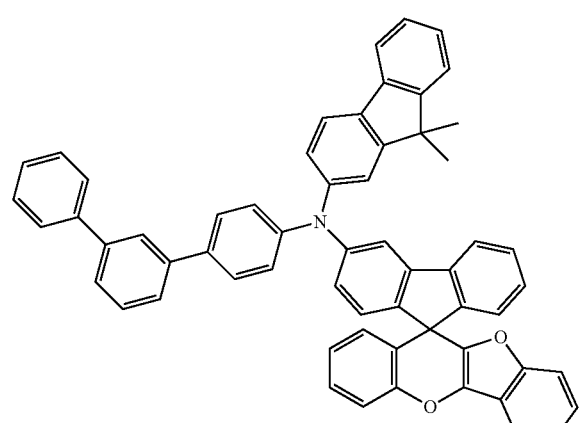
20
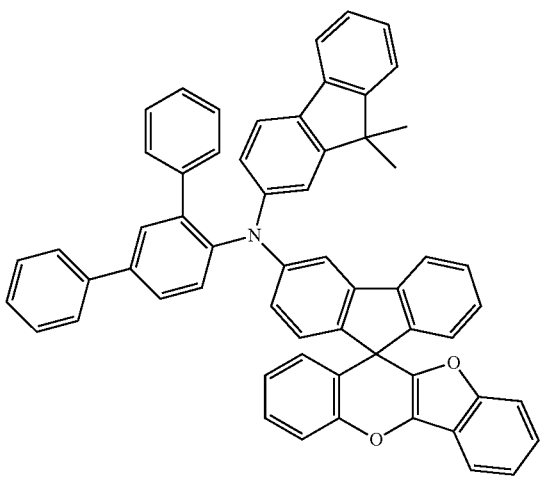
23
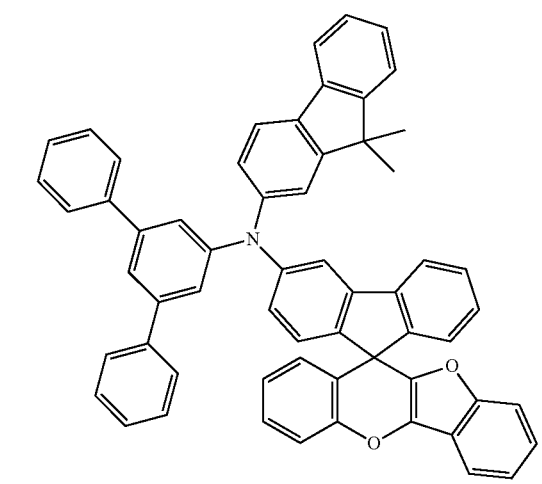
21
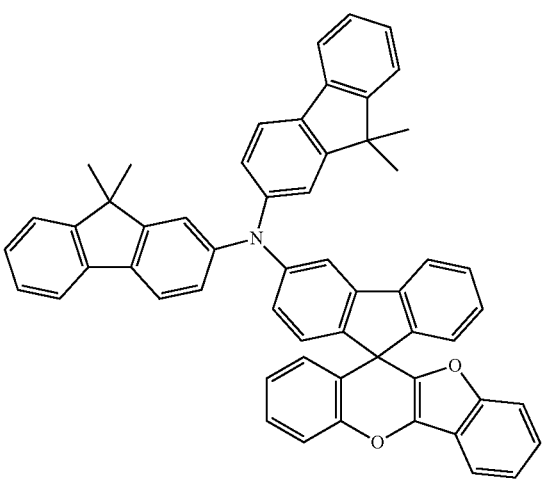
24

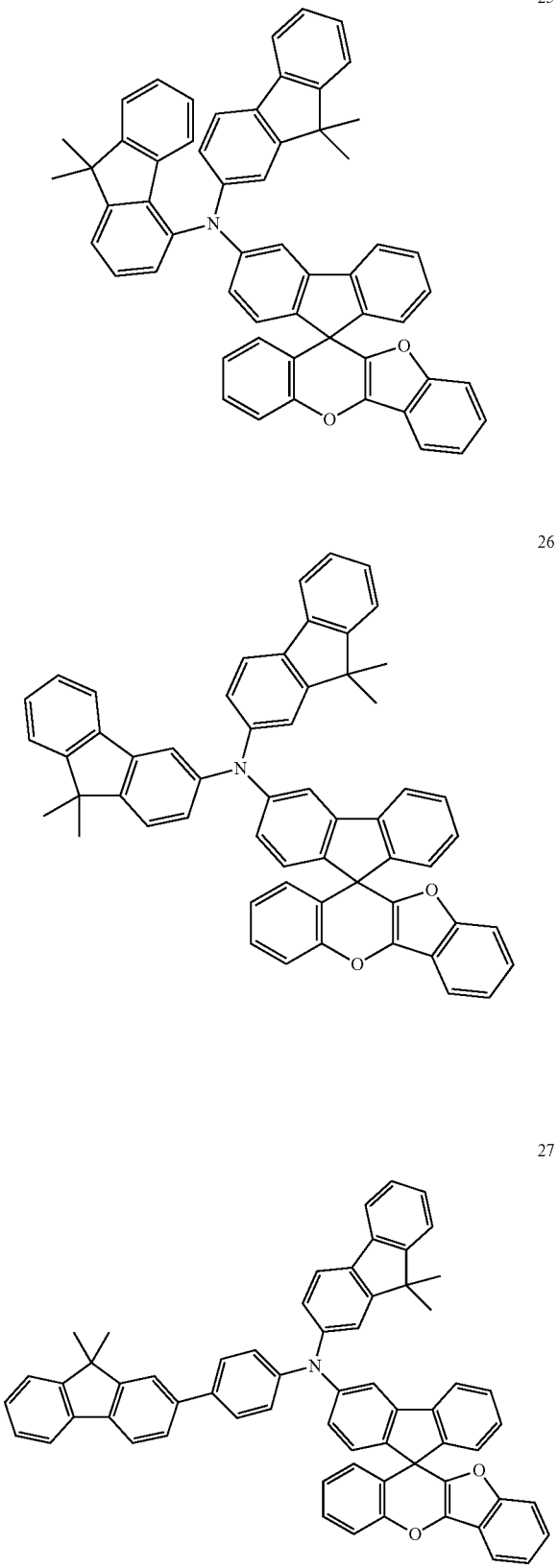
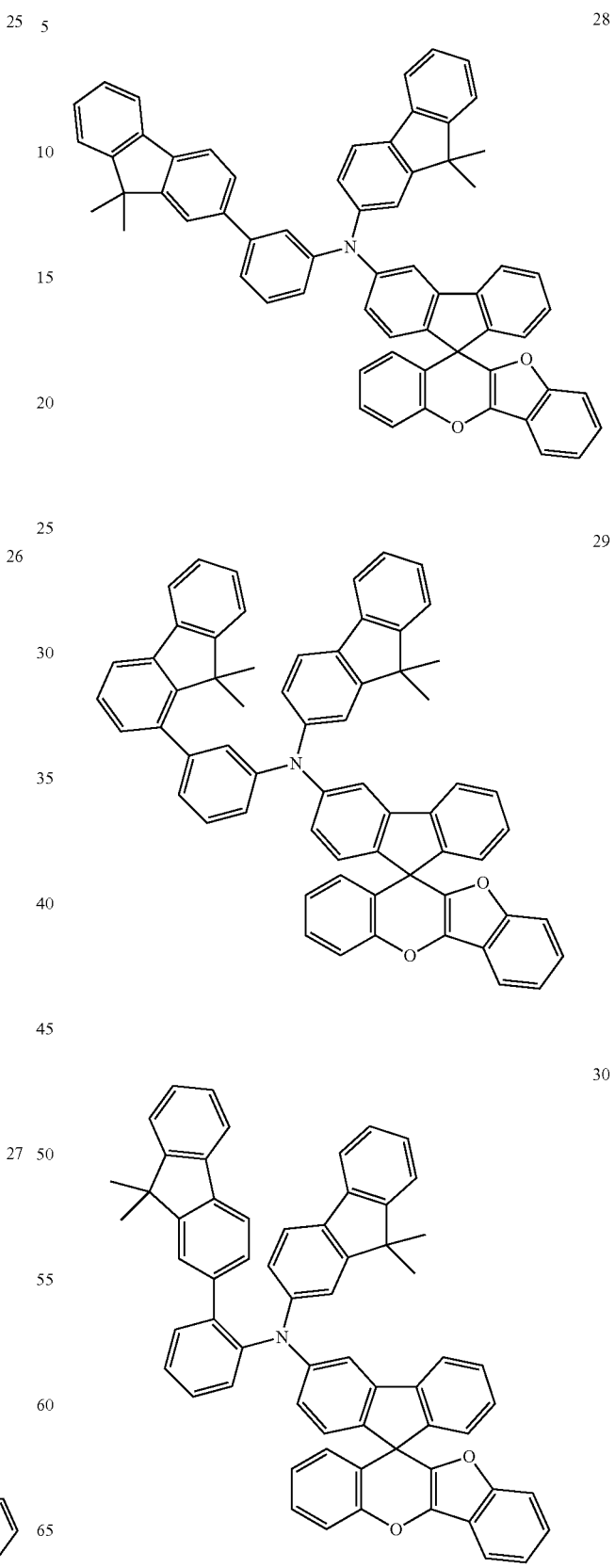

31
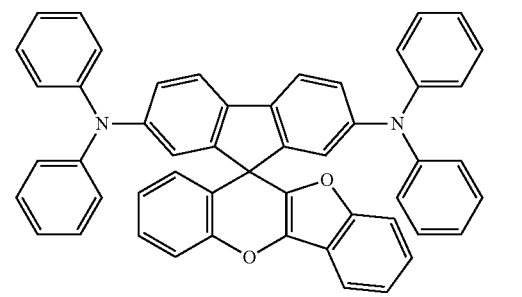
32
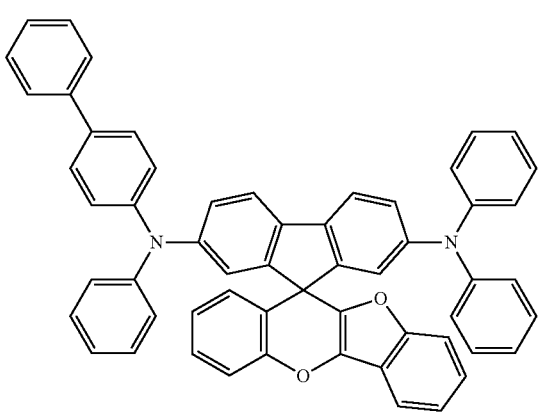
33
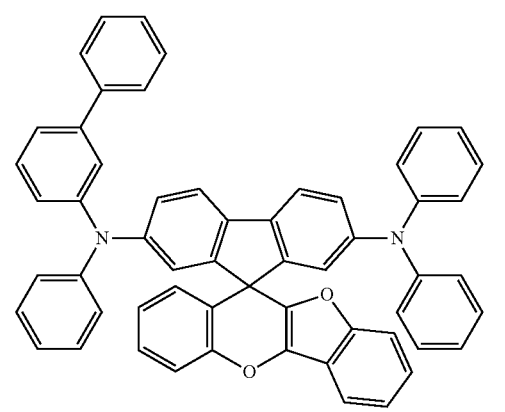
34
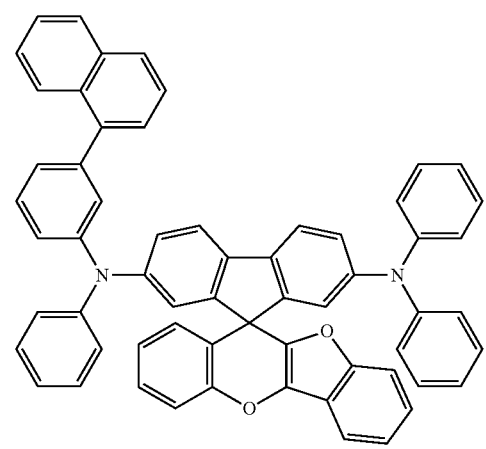
35
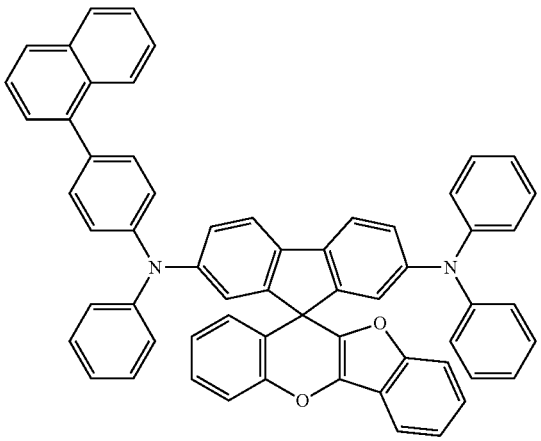
36
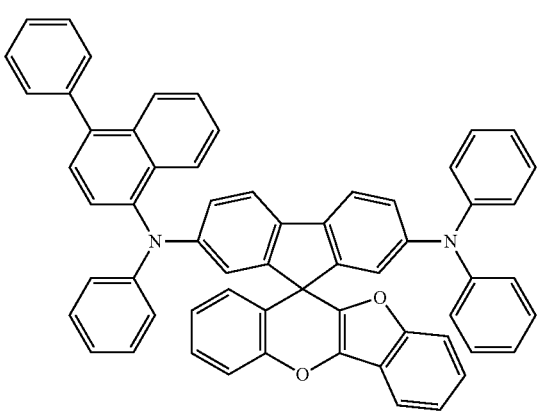
37
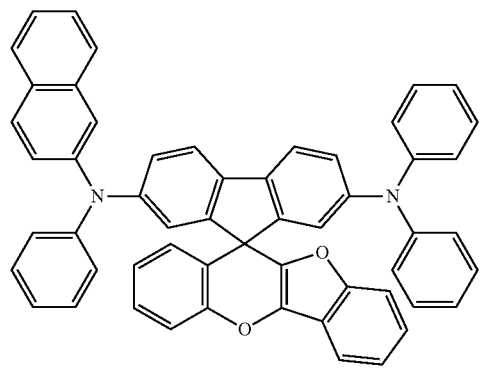

38
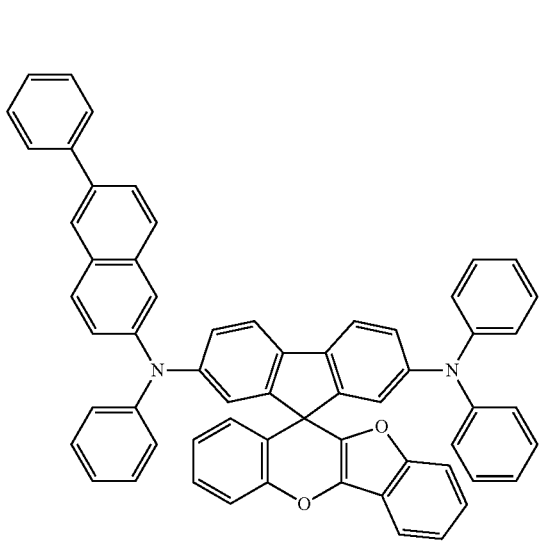
39
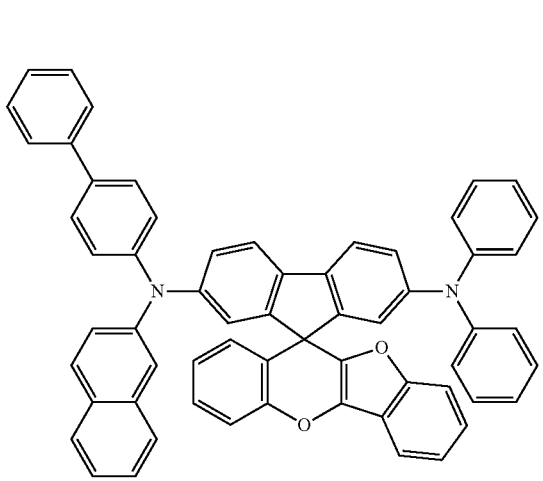
40
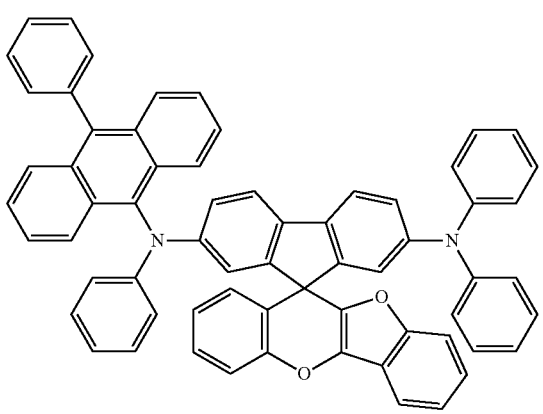
41
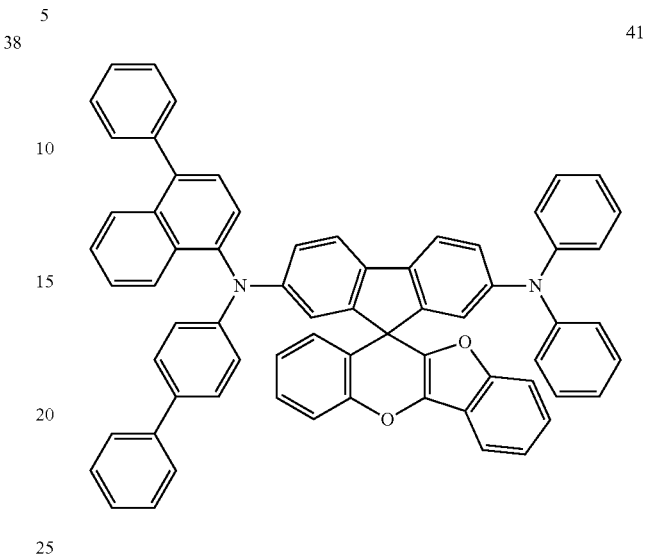
42
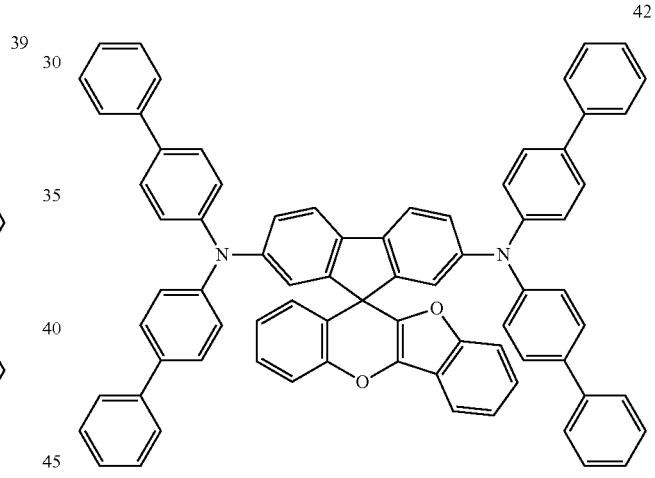
43
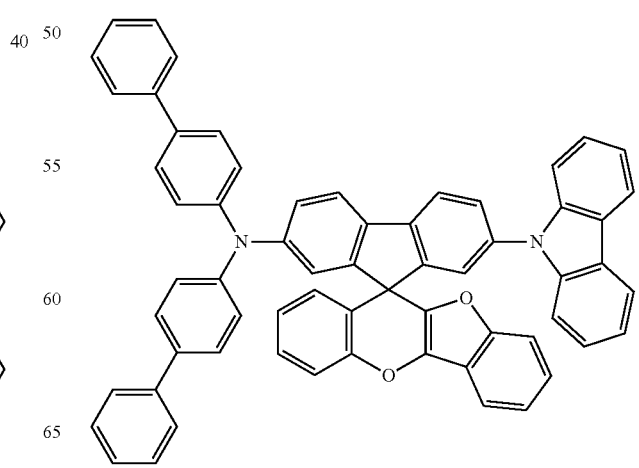

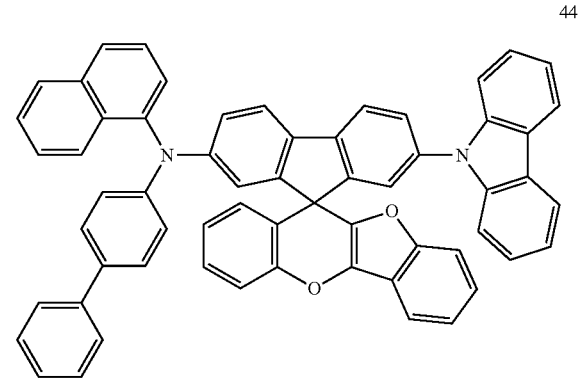
44
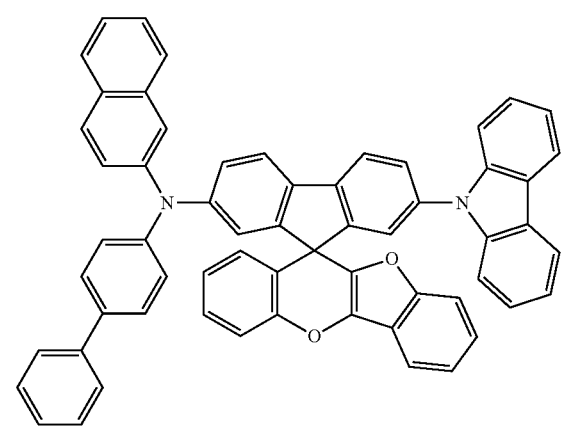
45
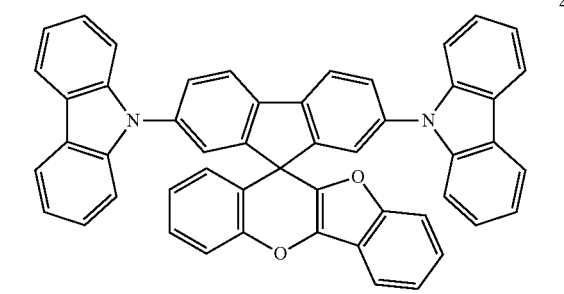
46
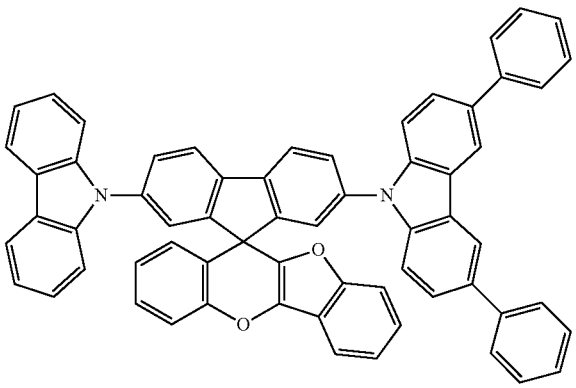
47
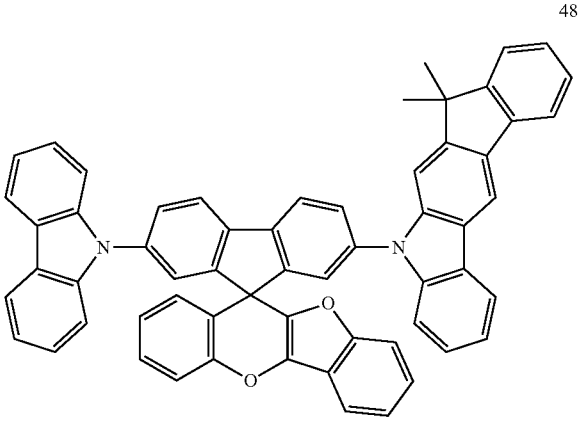
48
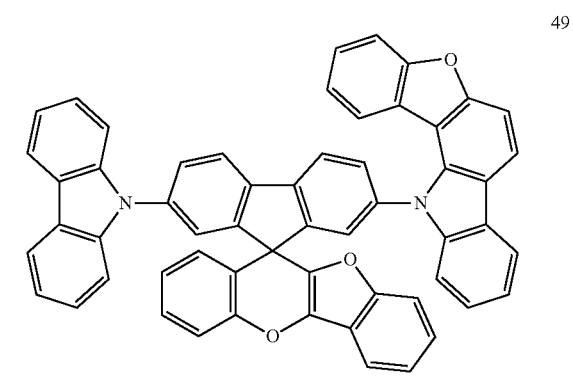
49
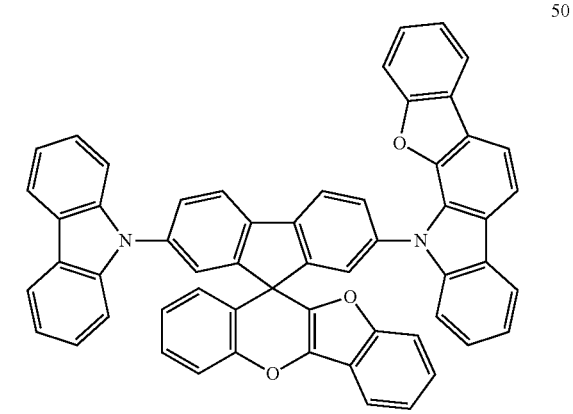
50
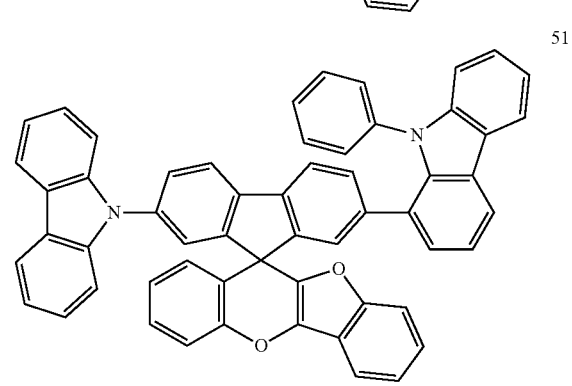
51

-continued
52
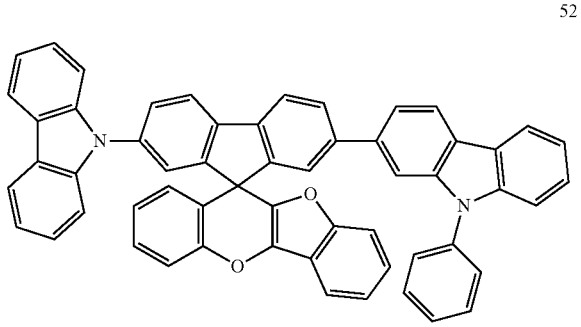
53
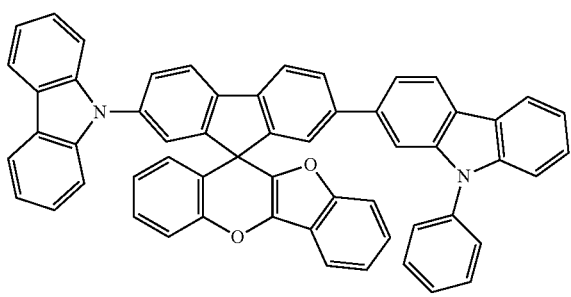
54
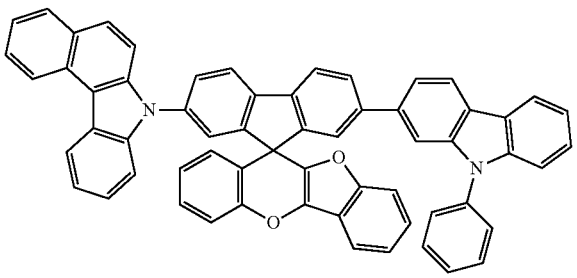
55
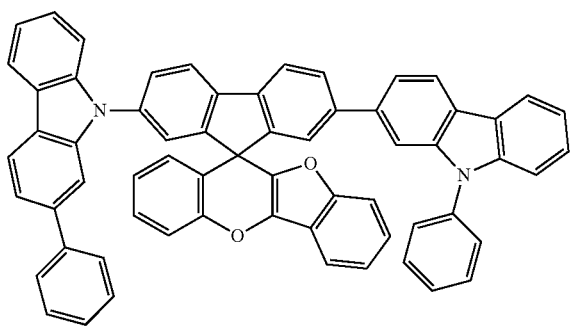
56
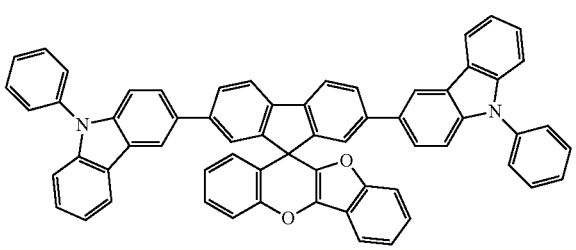
-continued
57
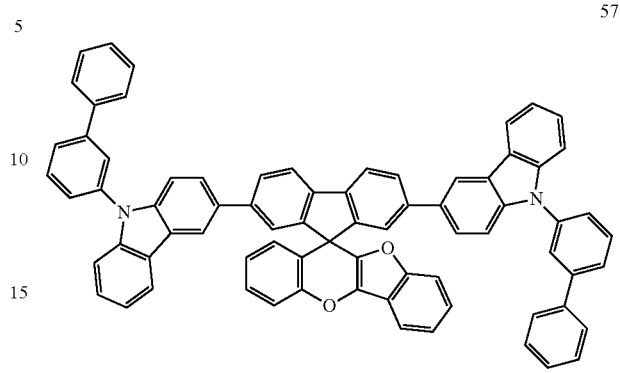
58
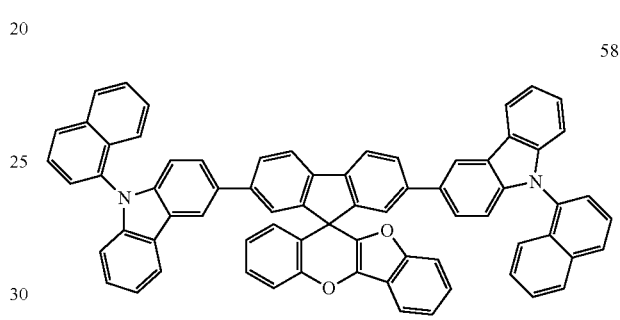
59
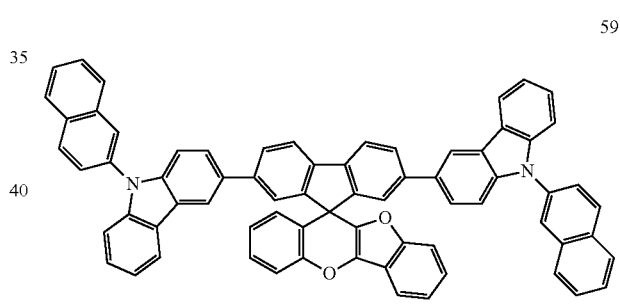
60
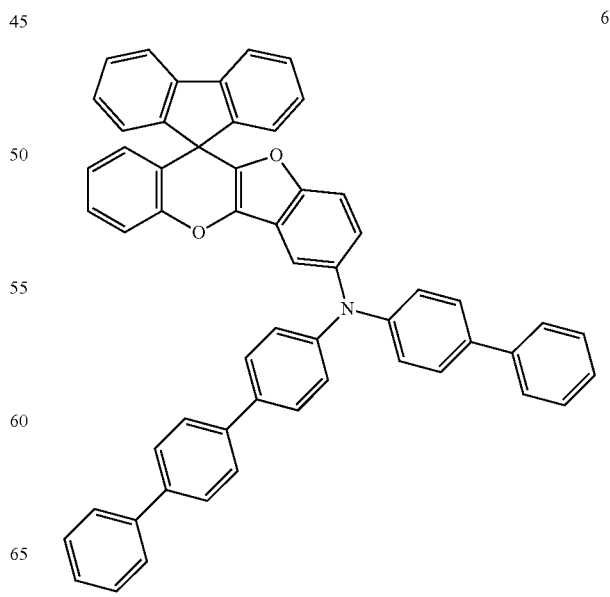

61
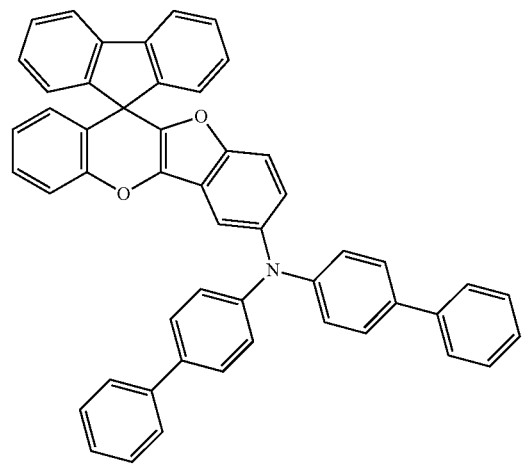
62
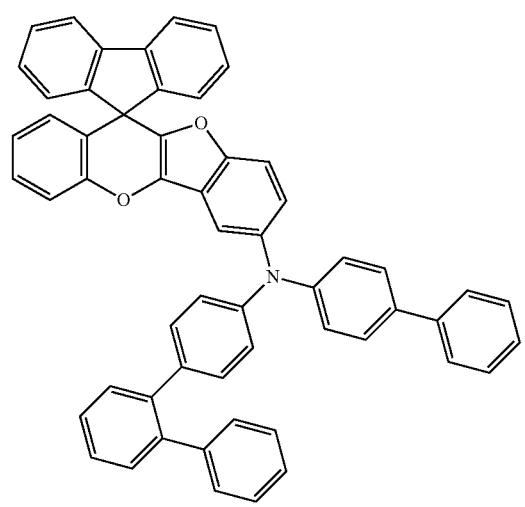
63
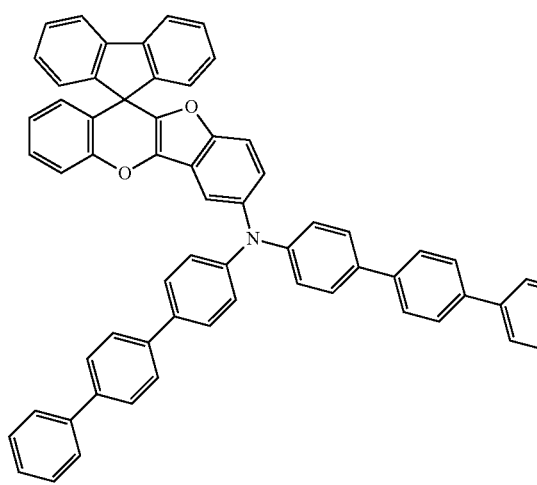
64
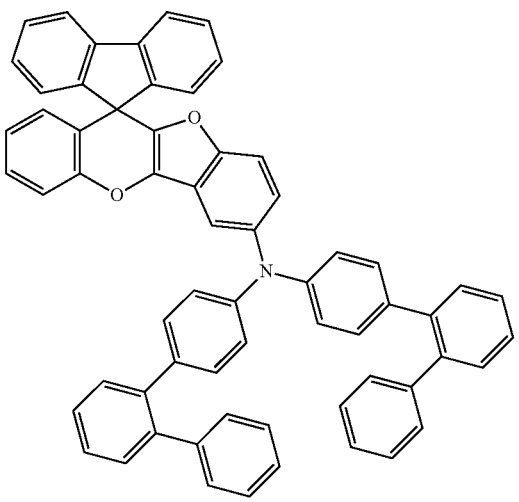
65
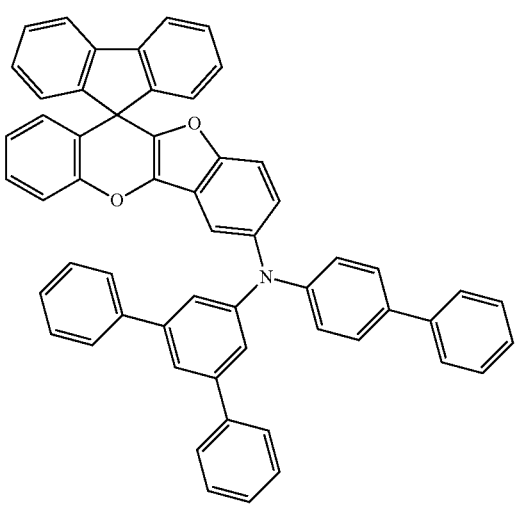
66
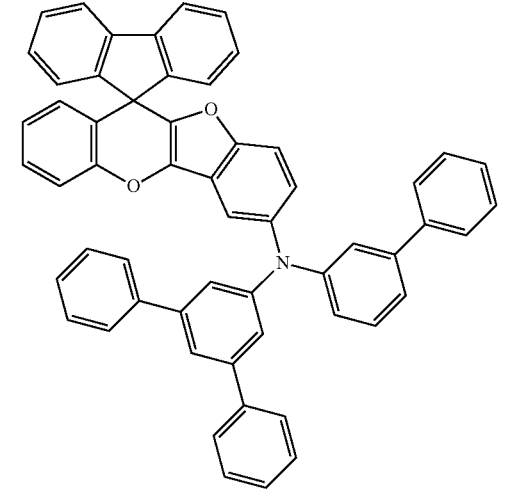

139
-continued
67
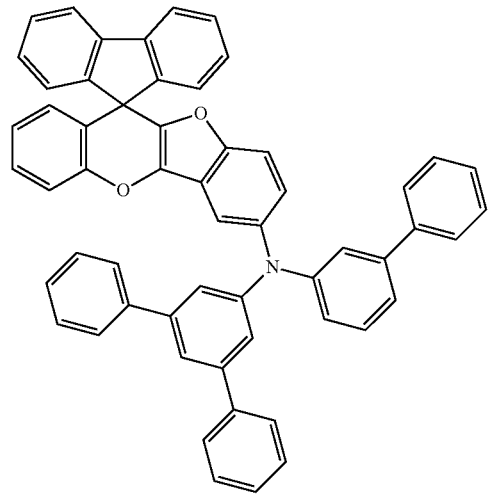
68
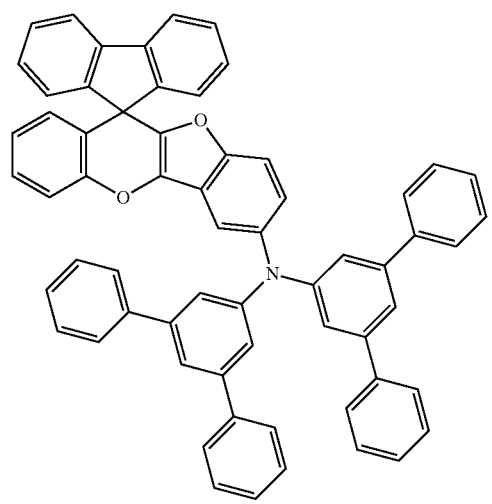
69
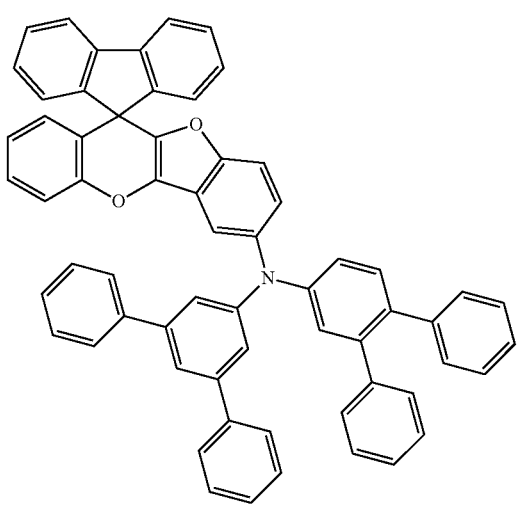
140
-continued
70
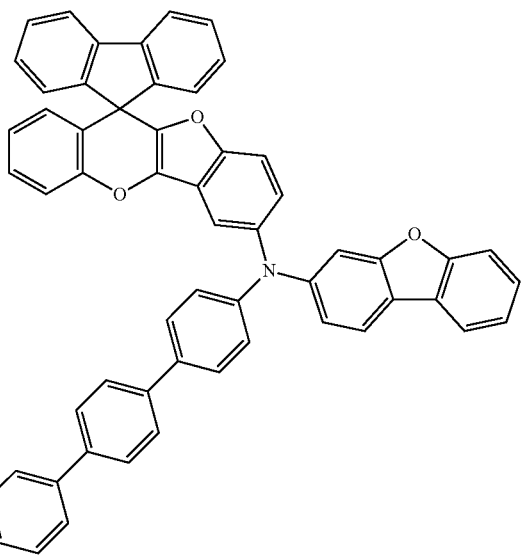
71
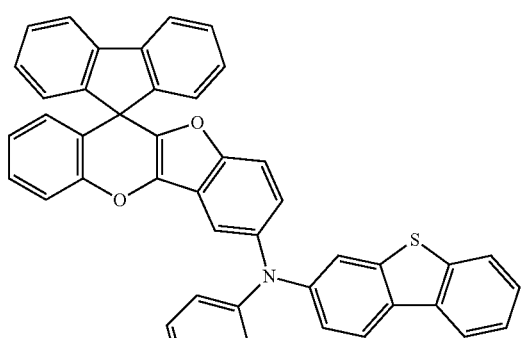
72

73
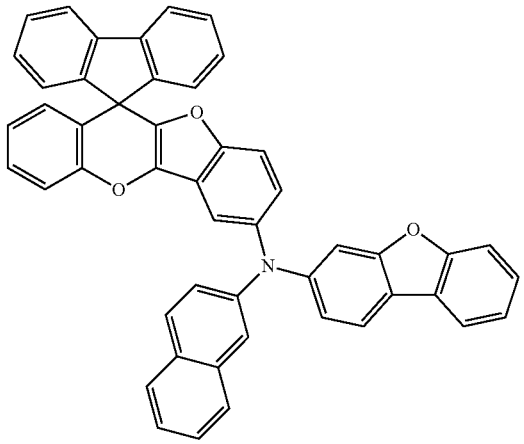
74
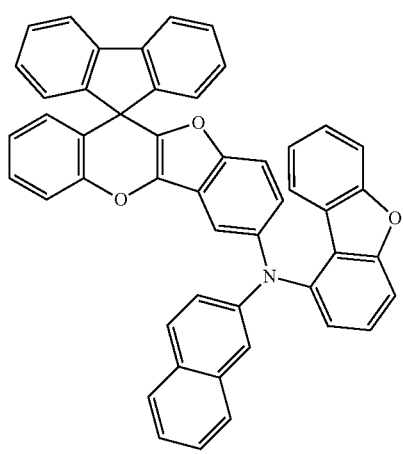
75
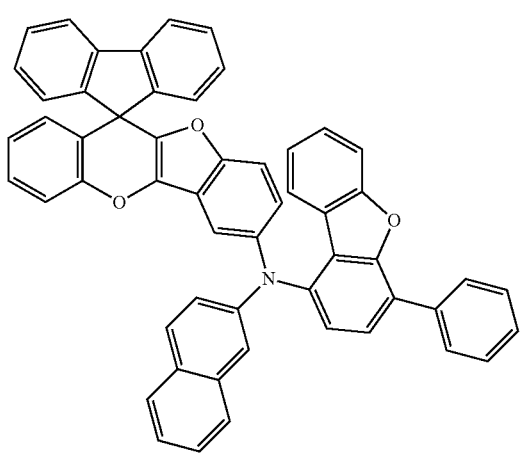
76
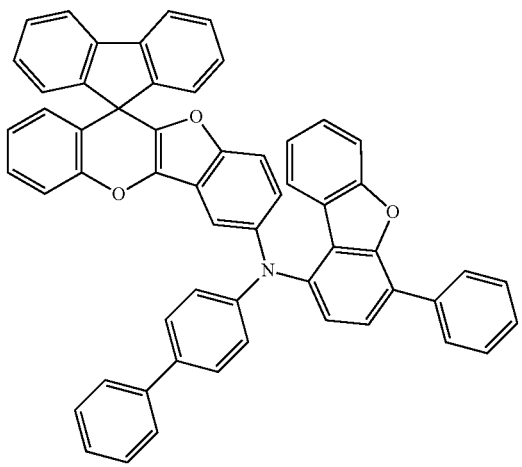
77
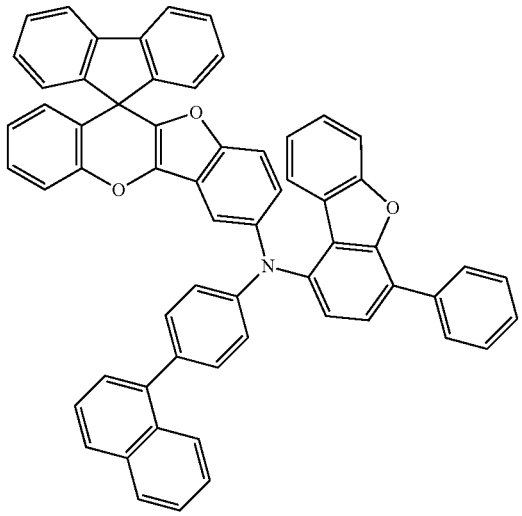
78
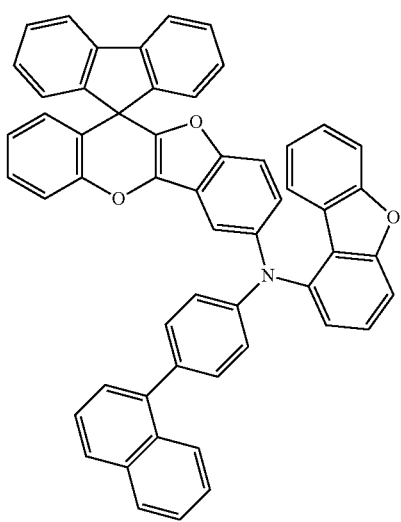

79
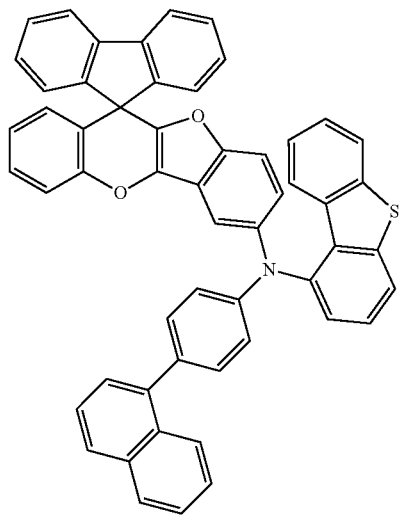
80
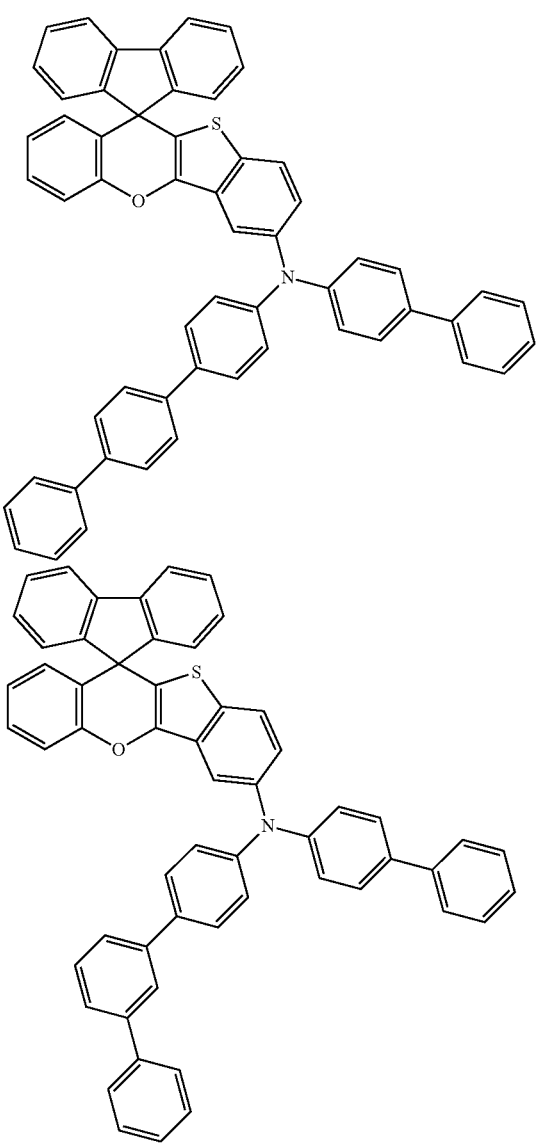
81
82
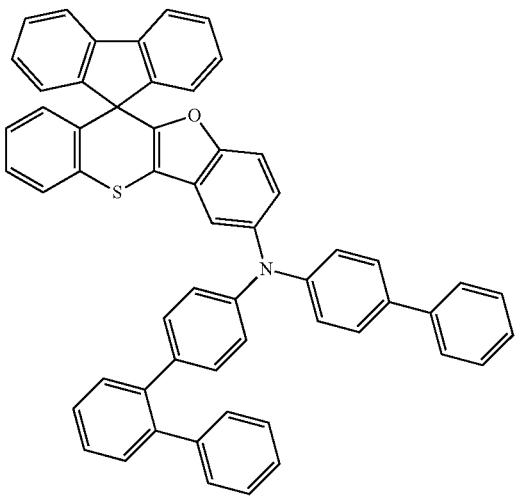
83
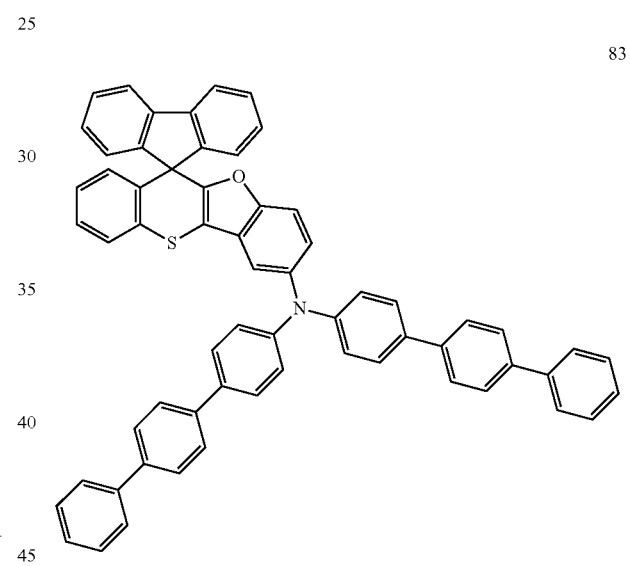
84
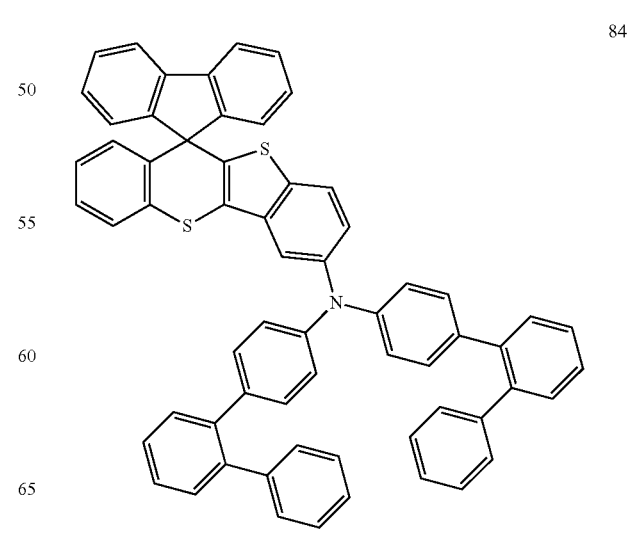

85
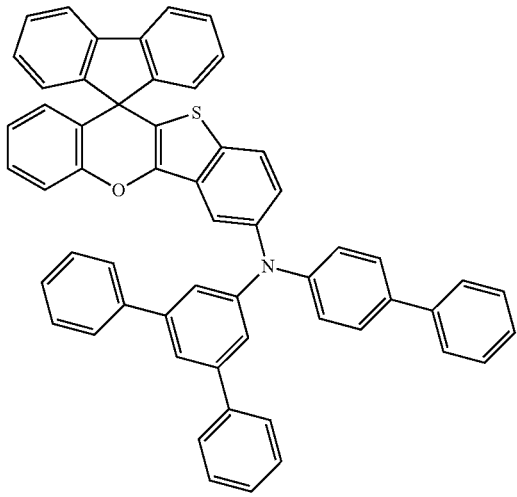
86
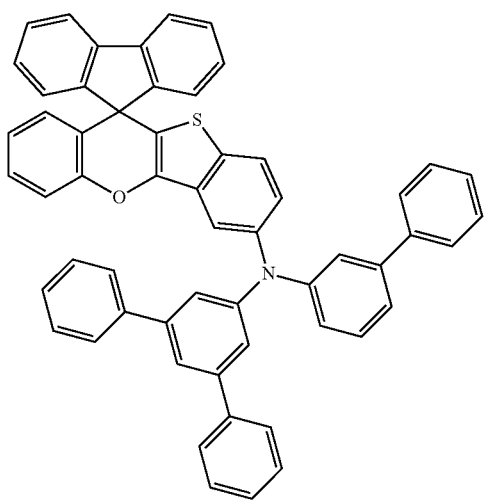
87
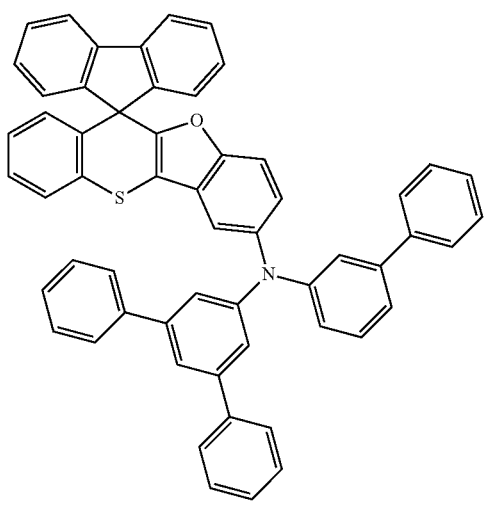
88
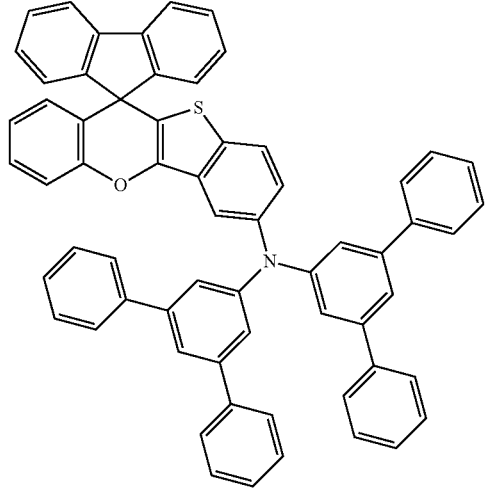
89
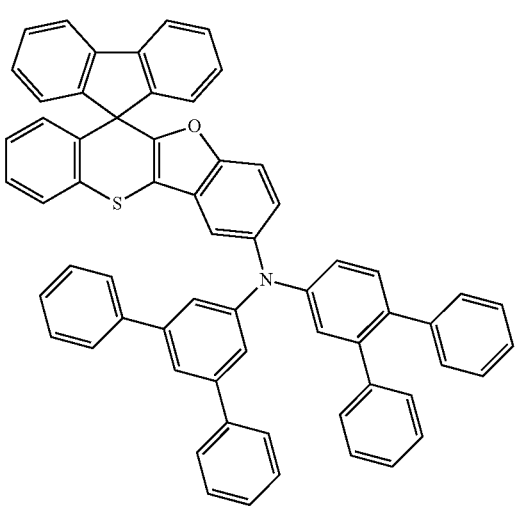
90
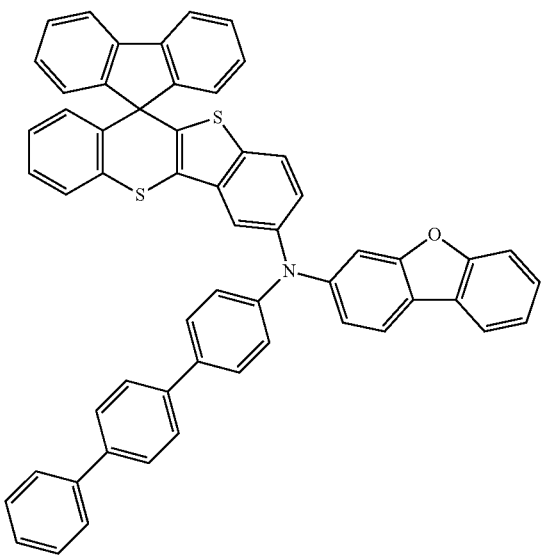

91
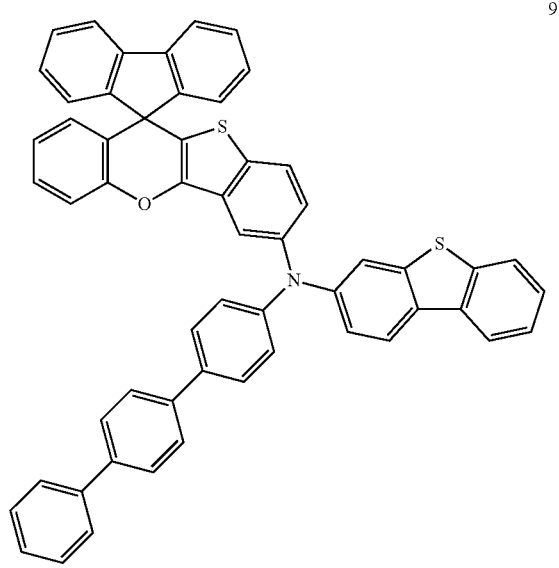
92
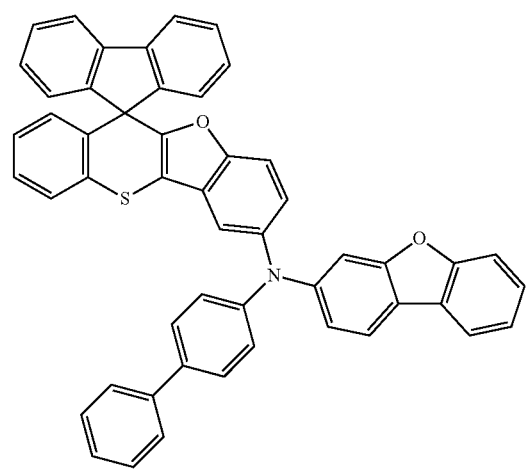
93
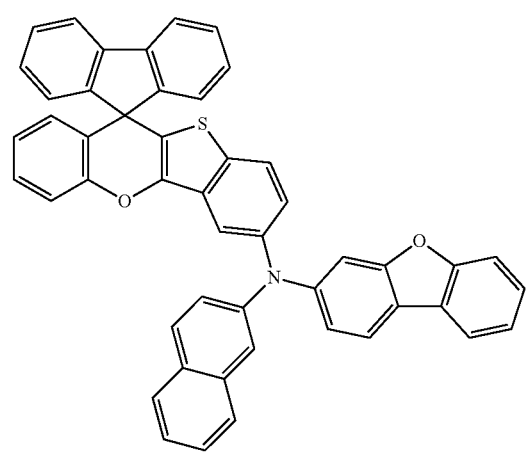
94
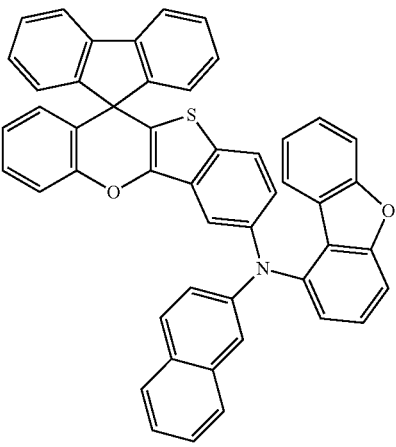
95
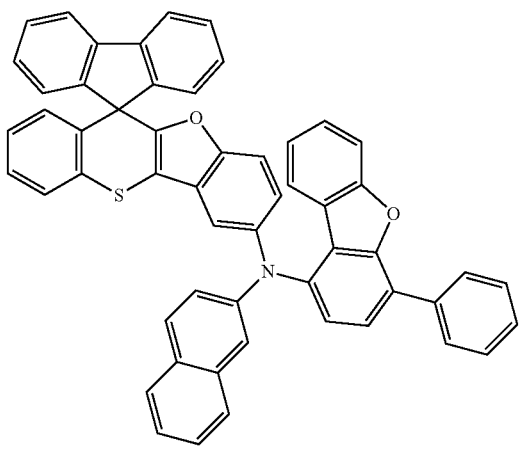
96
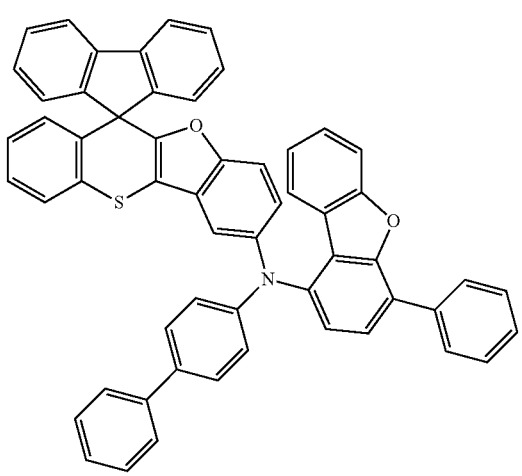

149
-continued
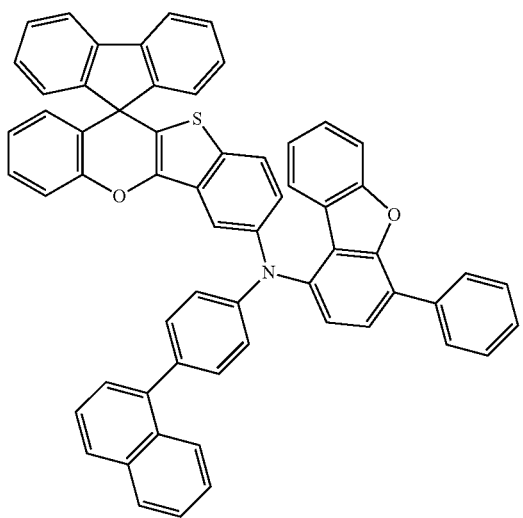
97
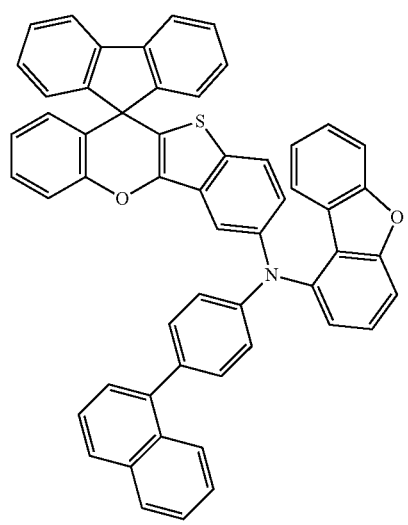
98
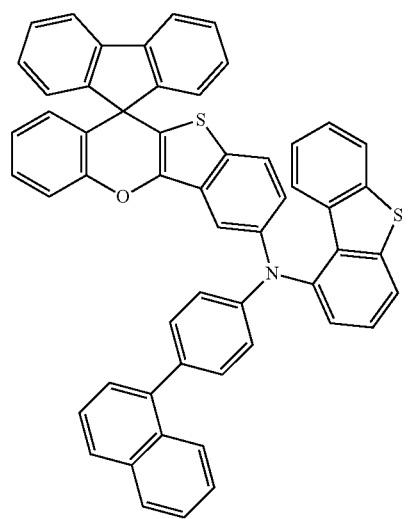
99
150
-continued
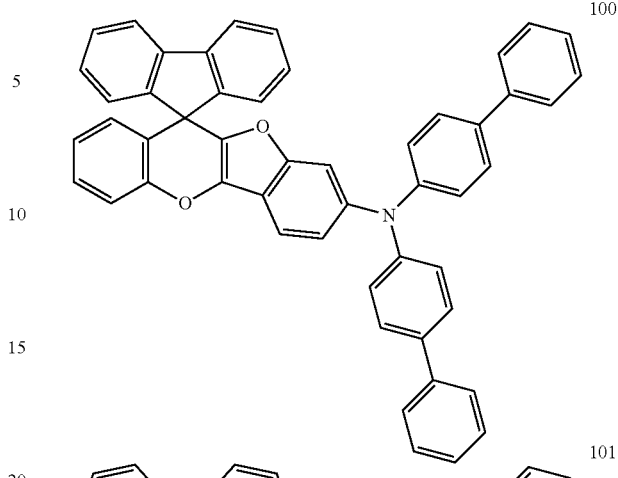
100
101
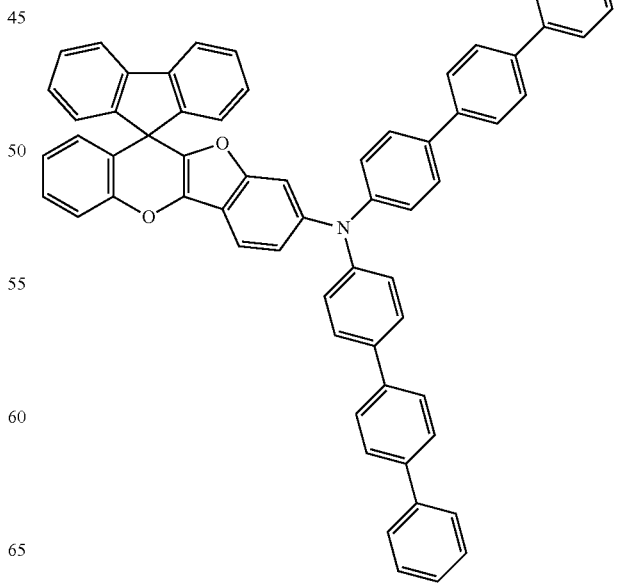
102

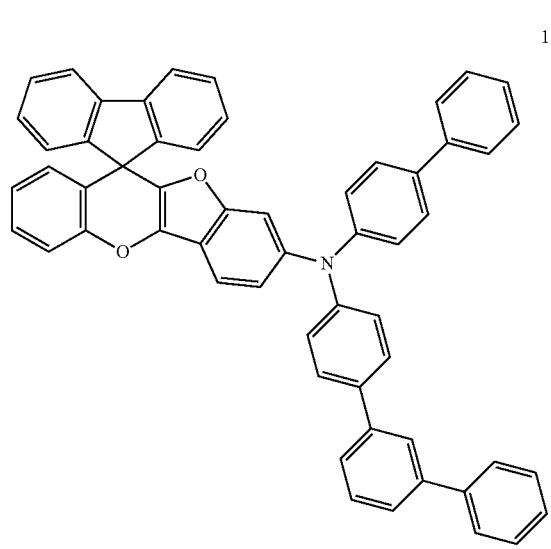
103
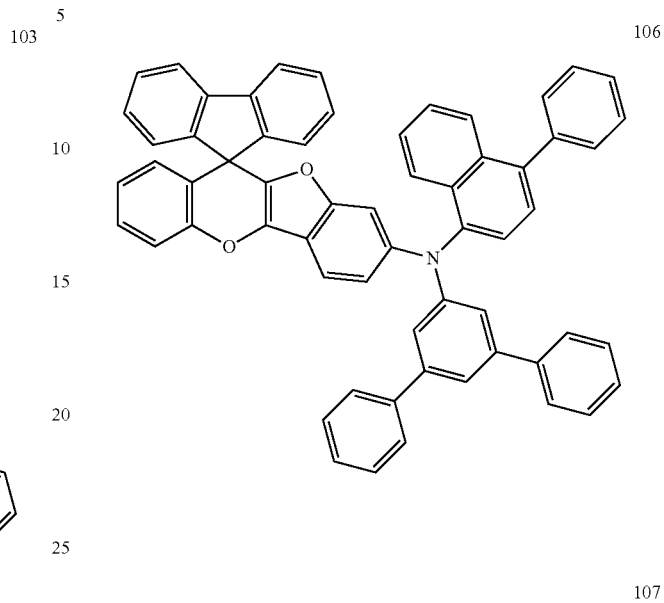
106
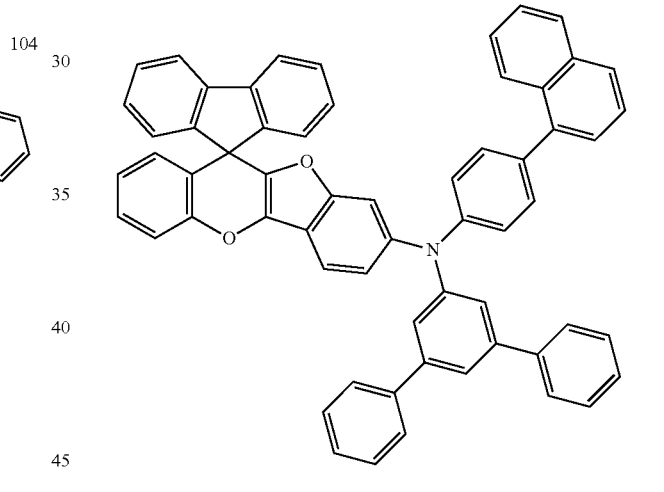
107
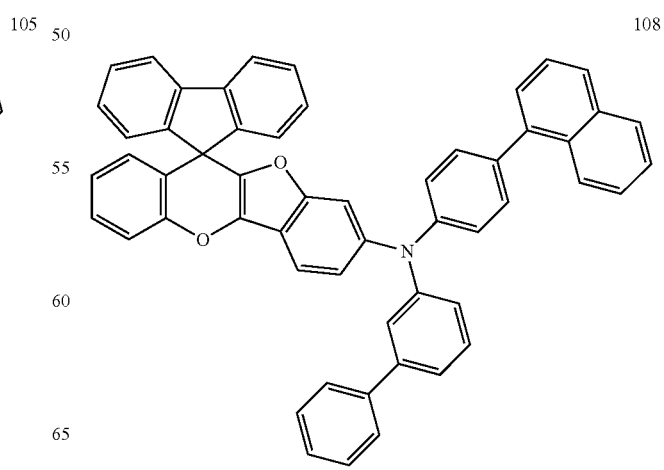
108

109
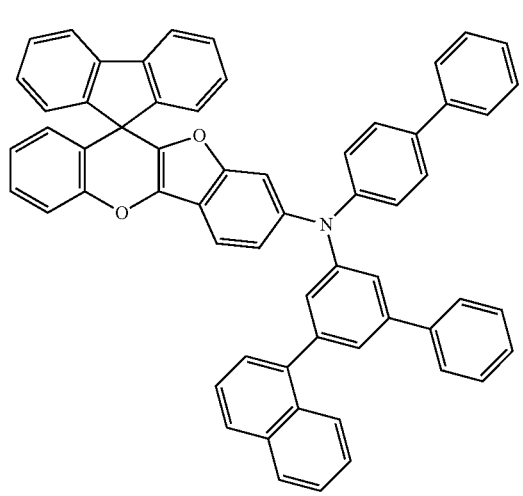
110
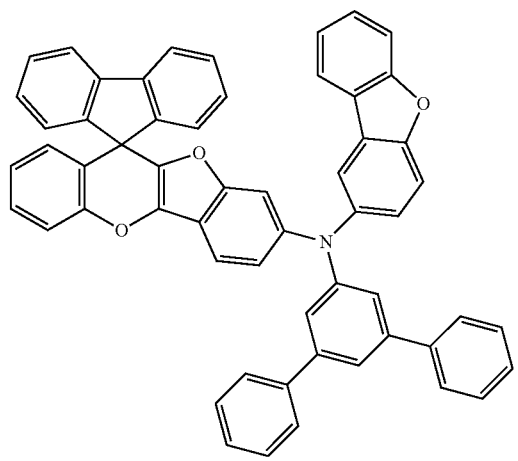
111
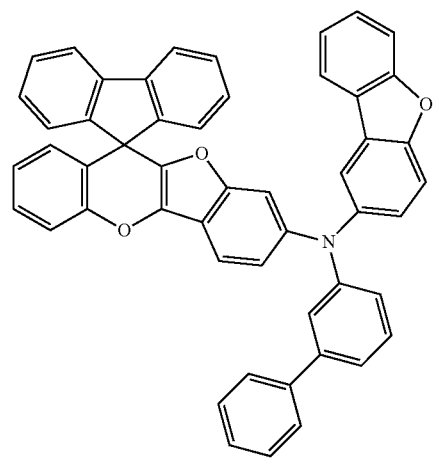
112
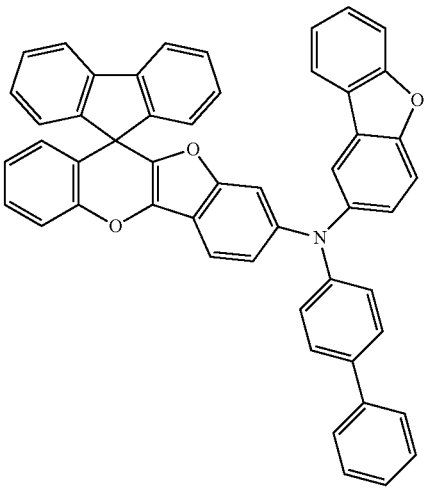
113
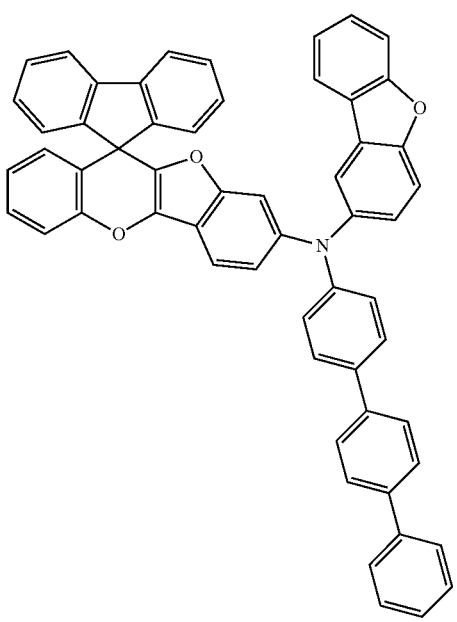
114
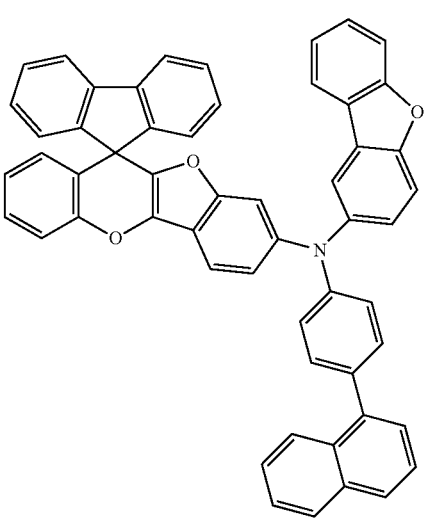

155
-continued
156
-continued
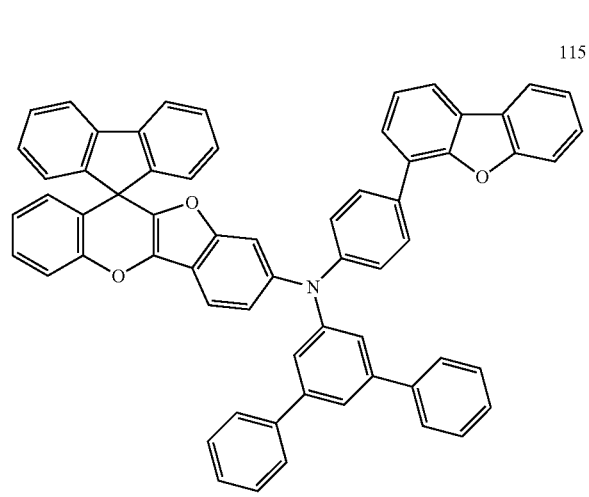
115
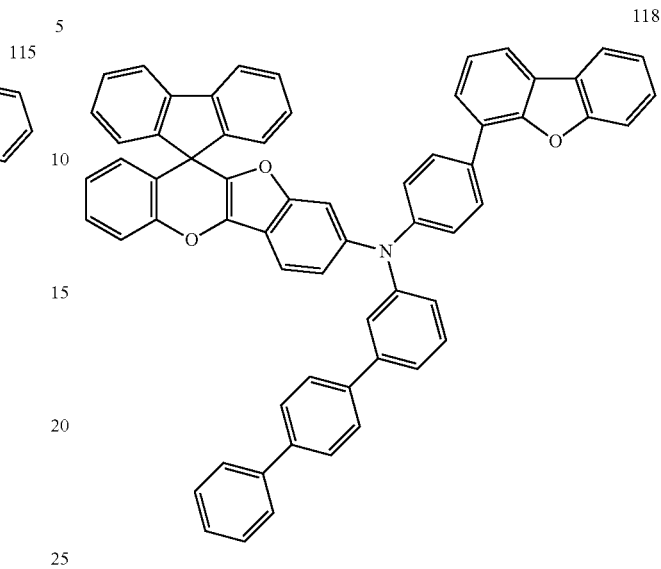
118
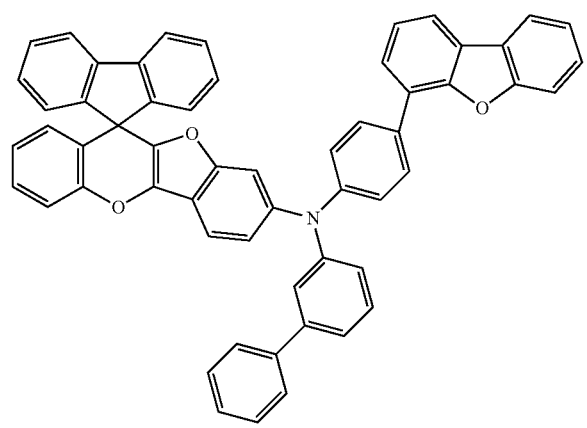
116
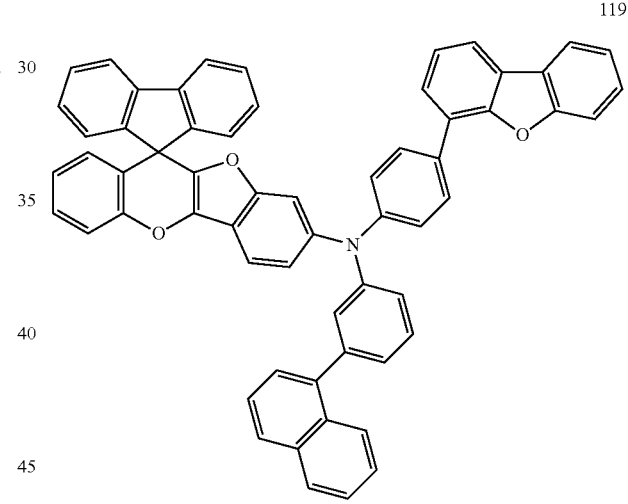
119
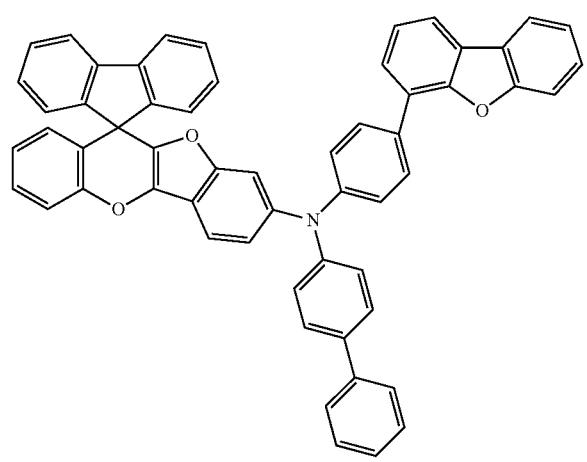
117
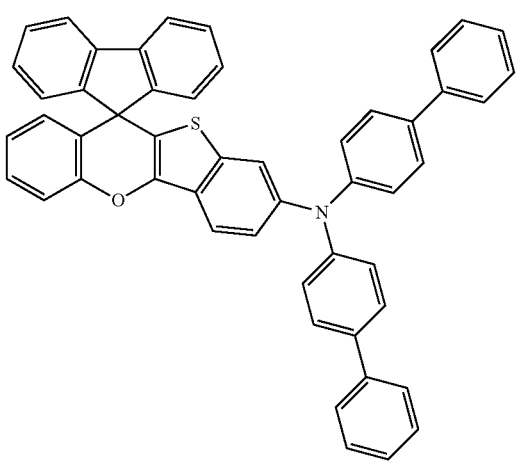
120

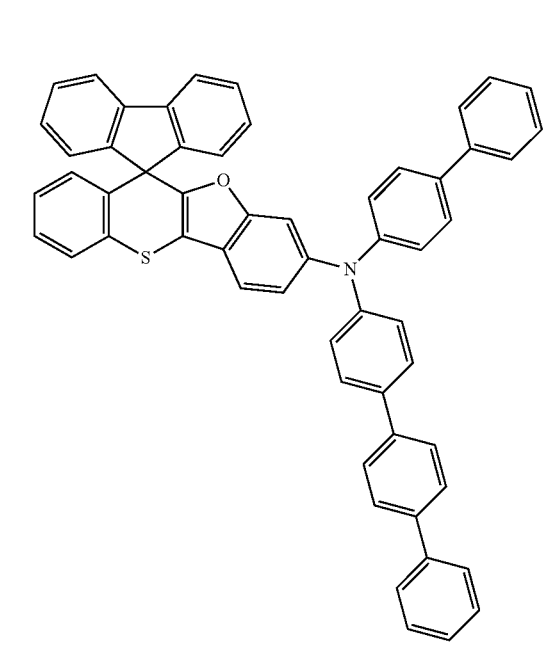
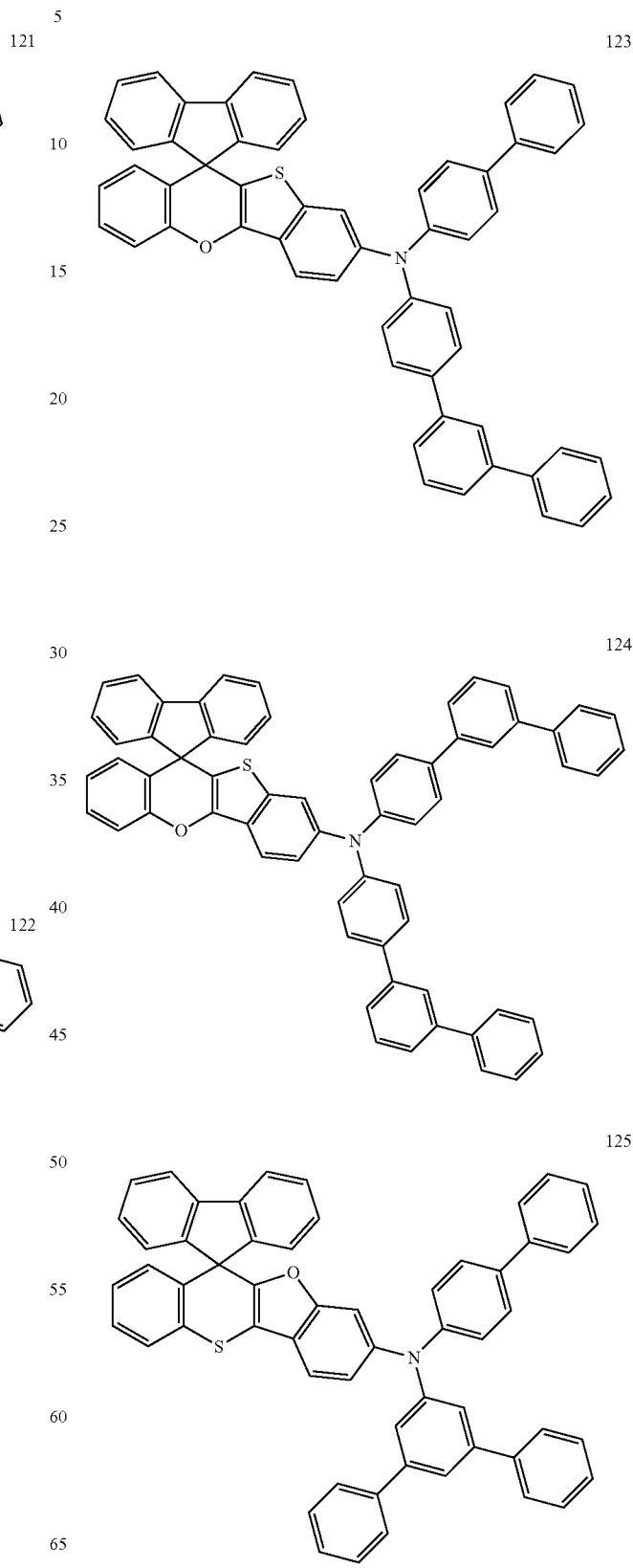

126
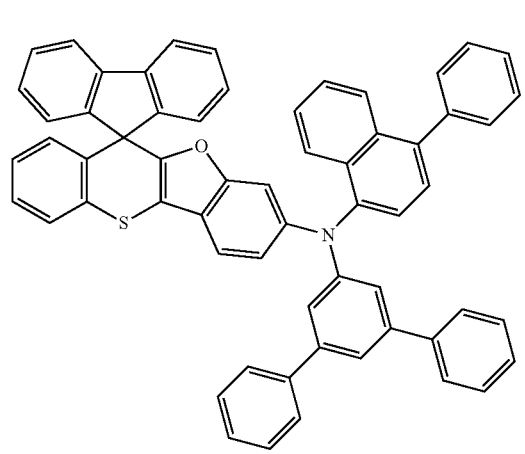
127
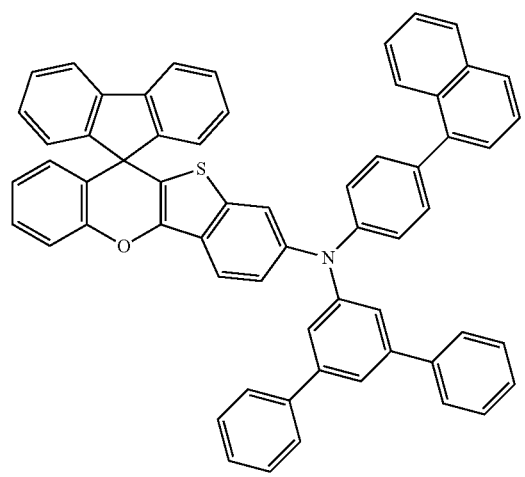
128
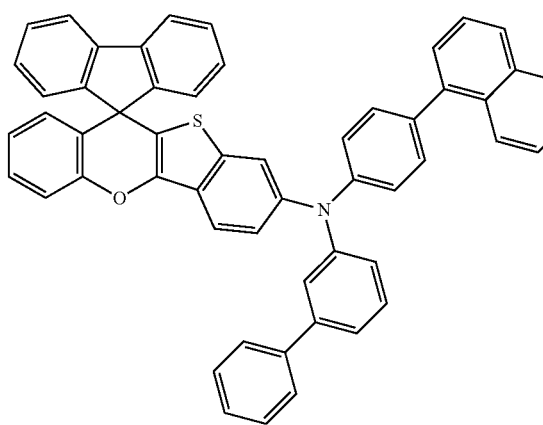
129
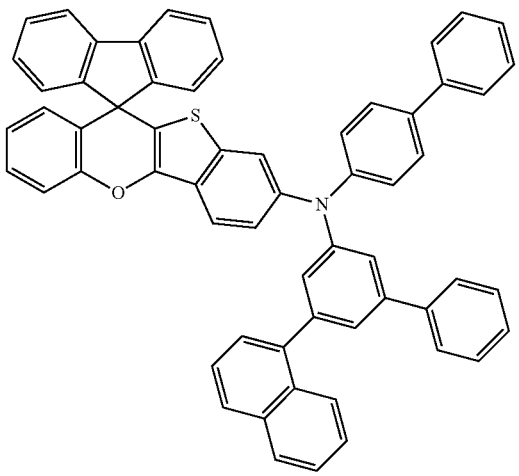
130
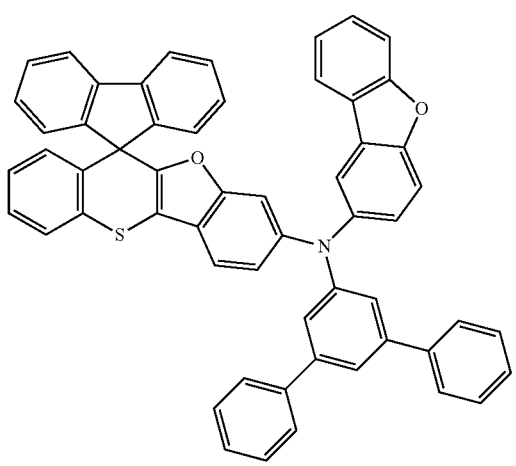
131
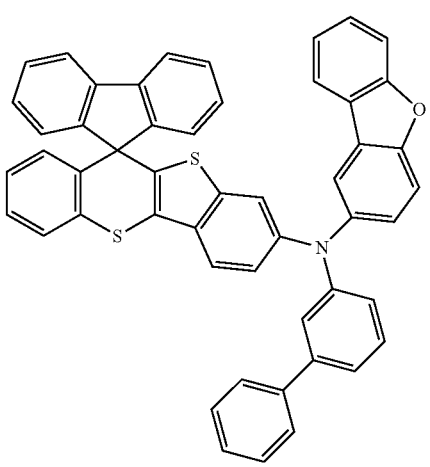

161
-continued
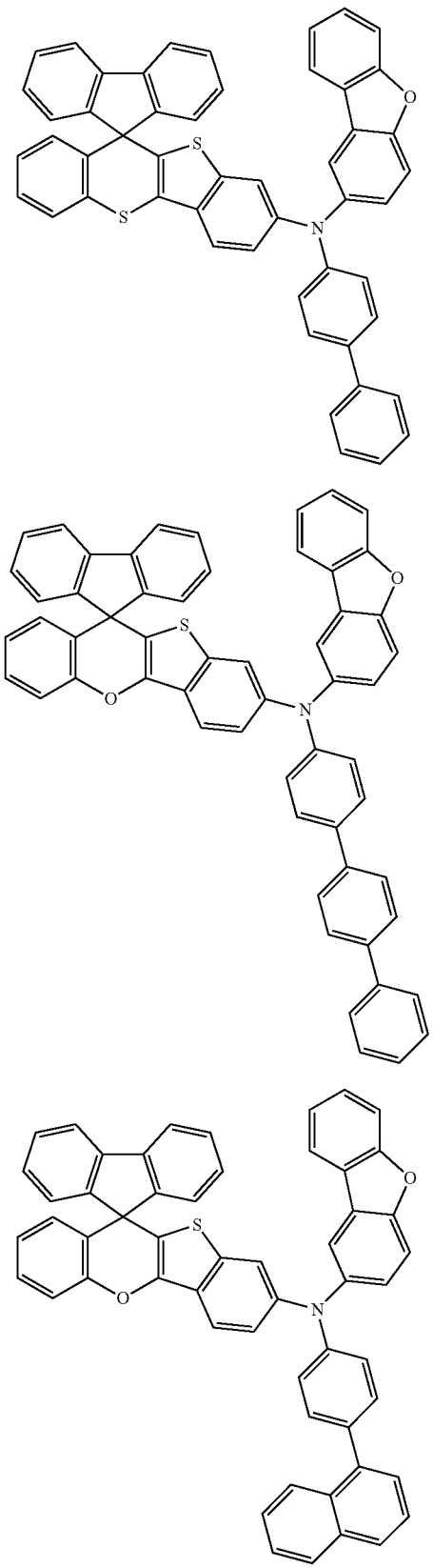
162
-continued
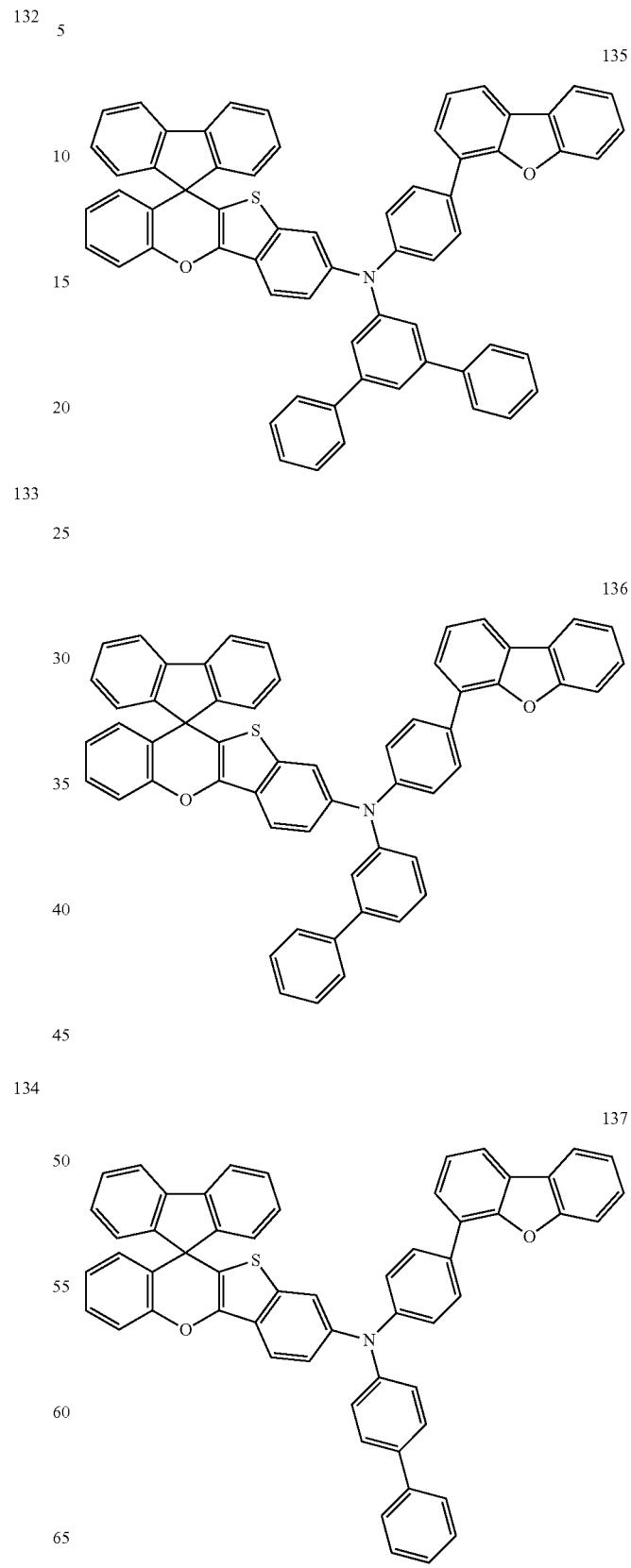

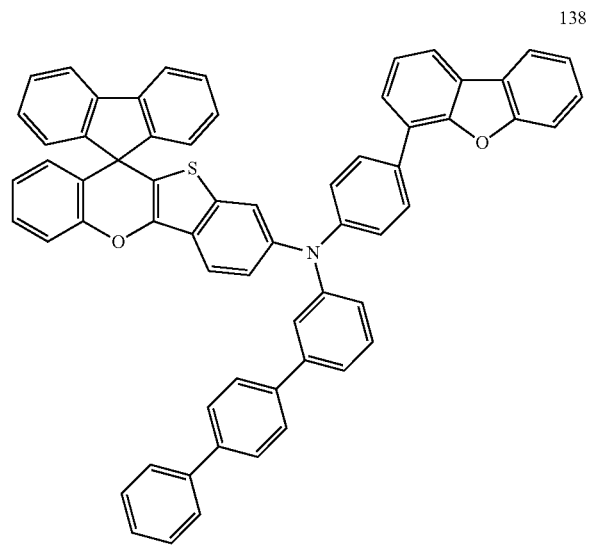
138
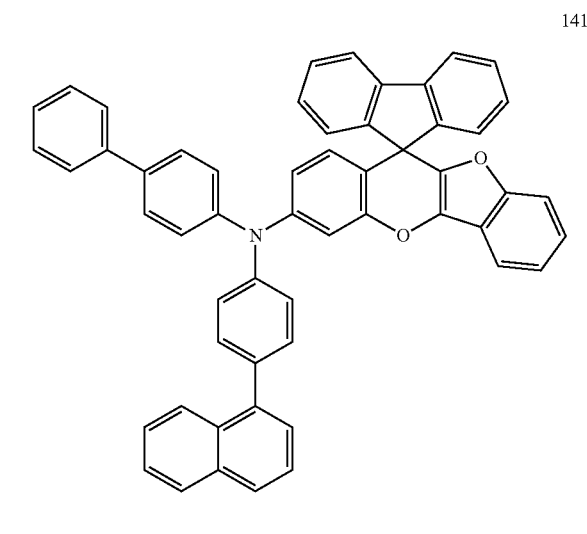
141
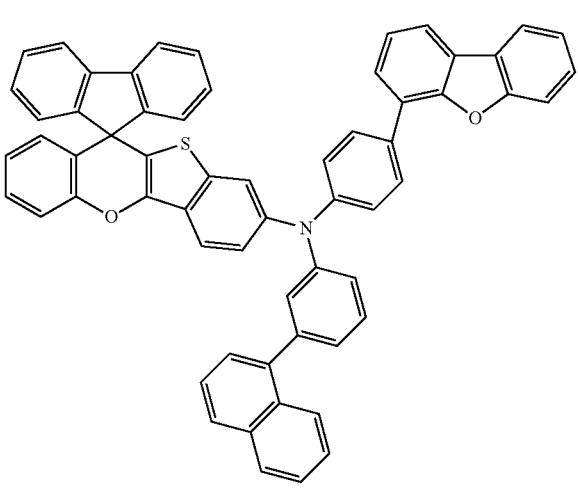
139
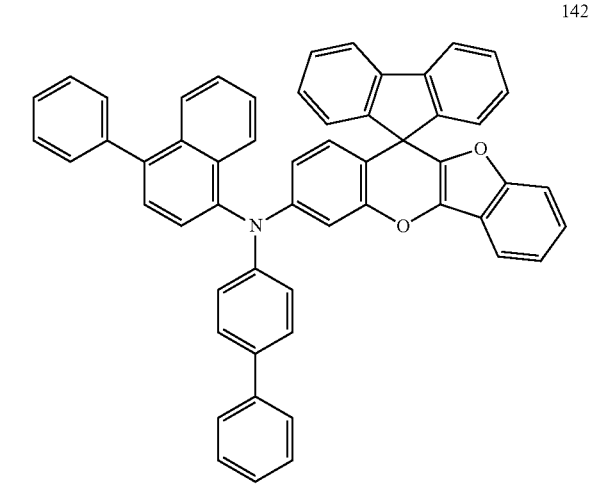
142
140
143

144
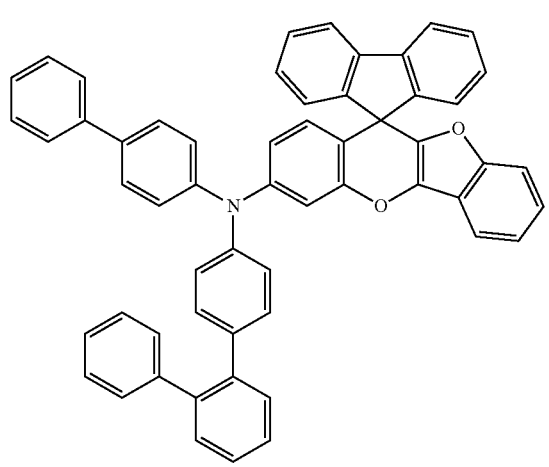
145
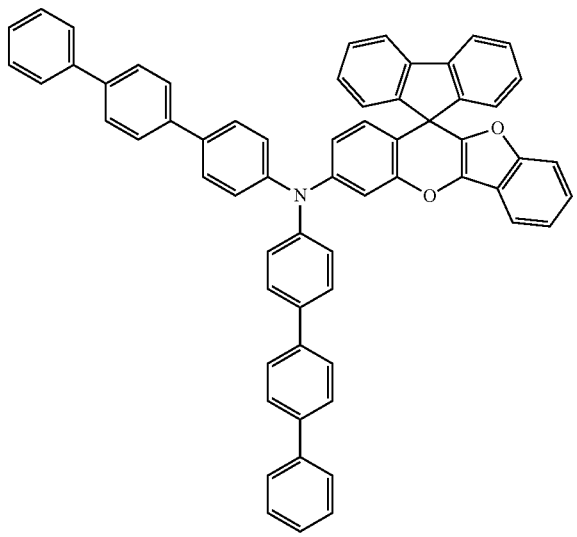
146
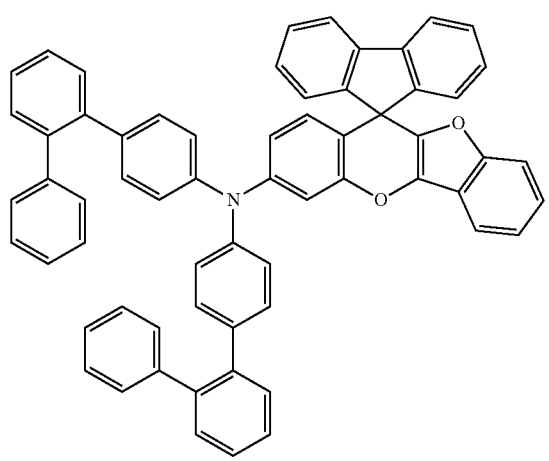
147
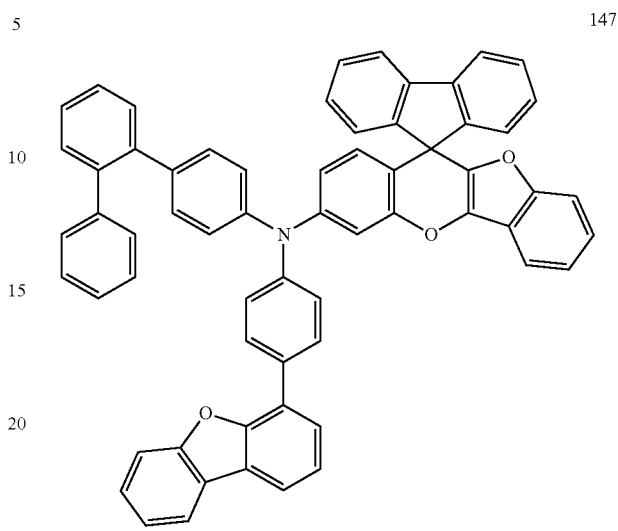
148
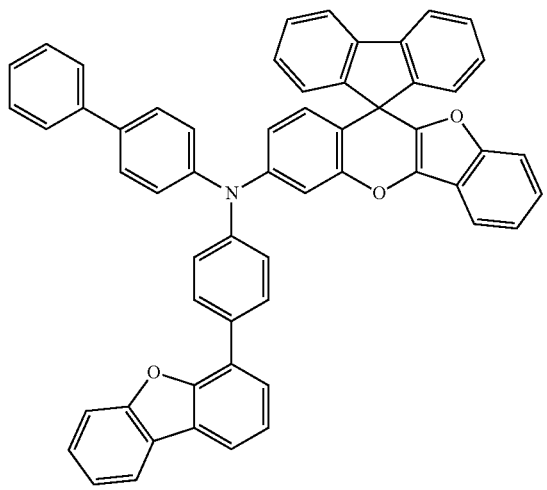
149
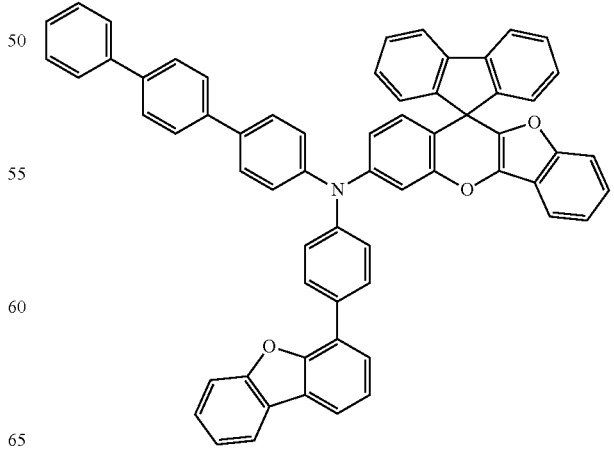

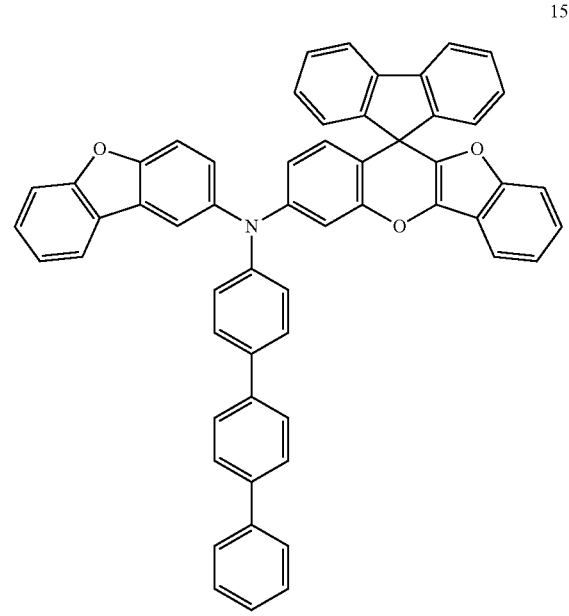
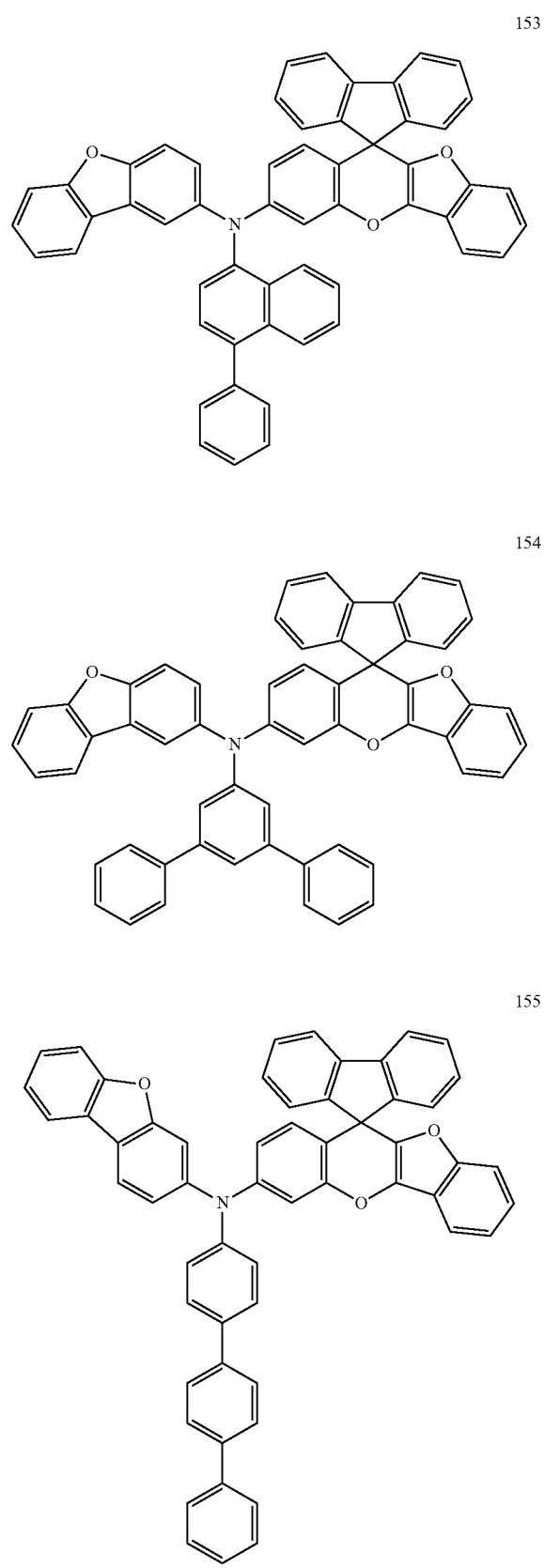

169
-continued
156
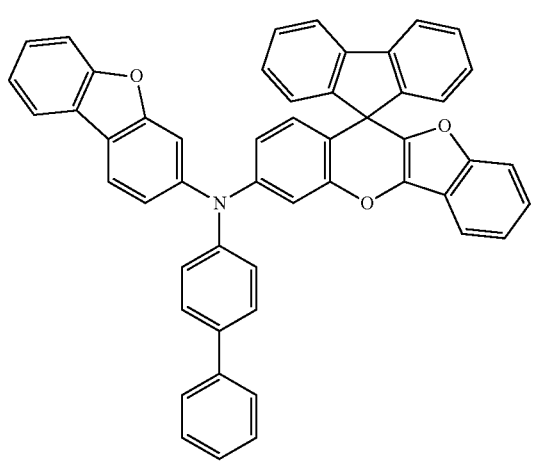
157
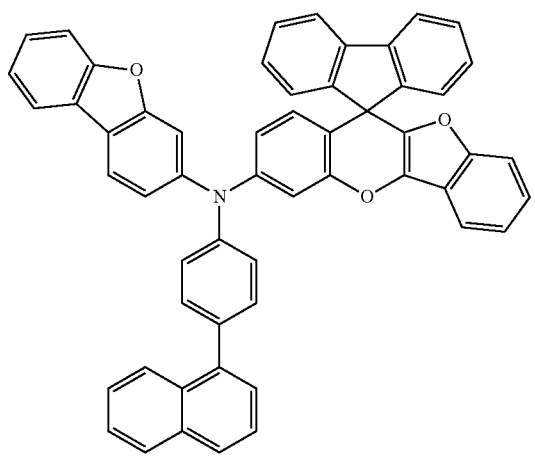
158
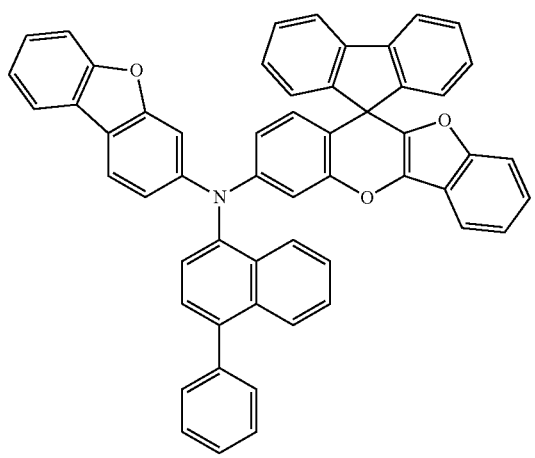
170
-continued
159
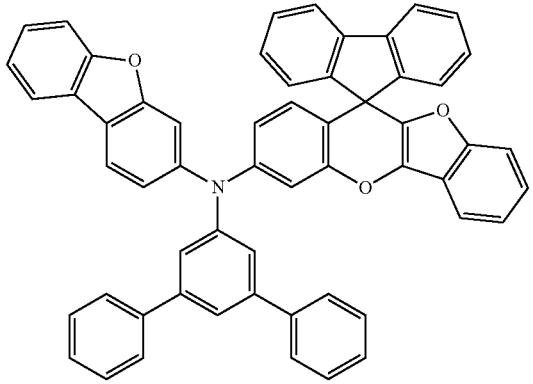
160
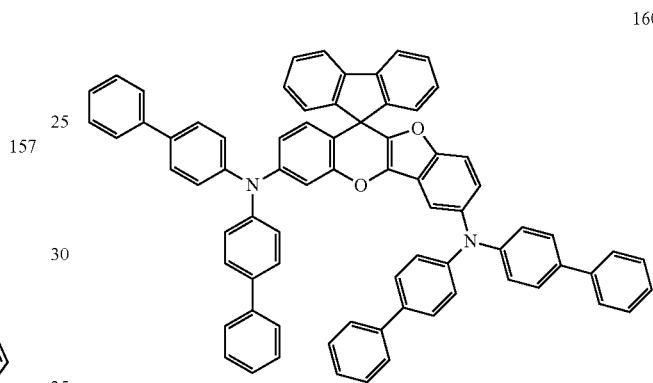
161
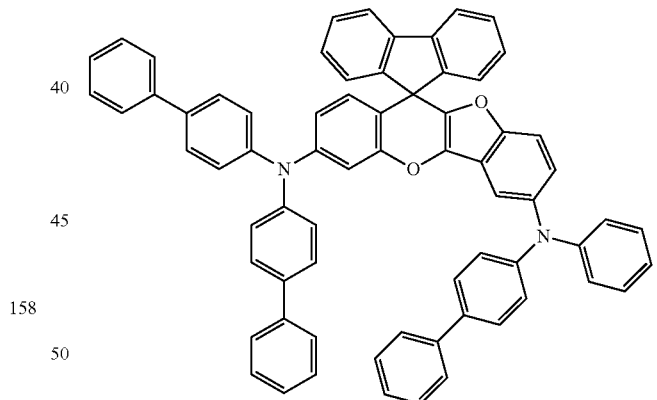
162
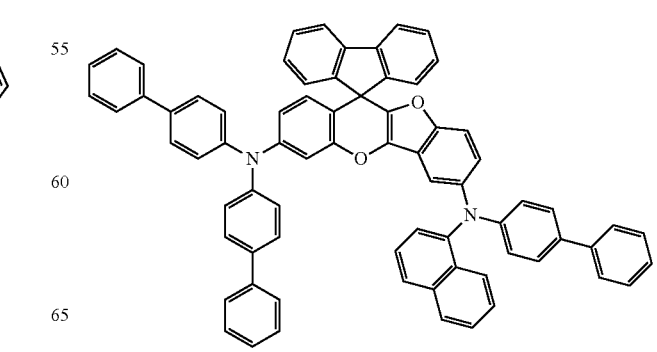

163
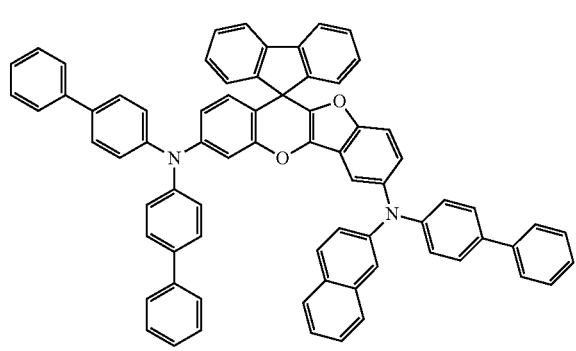
164
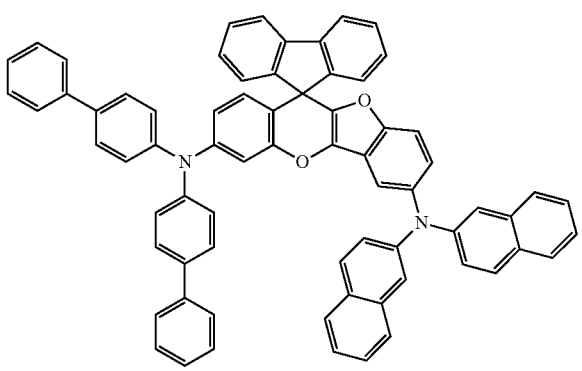
165
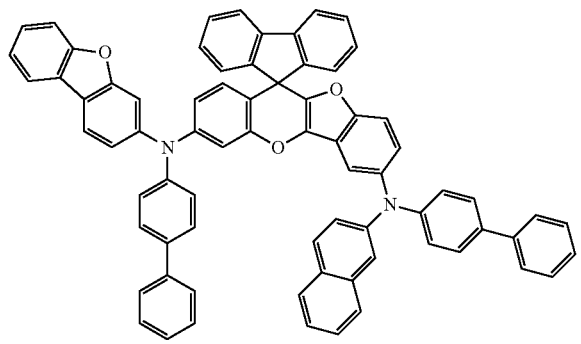
166
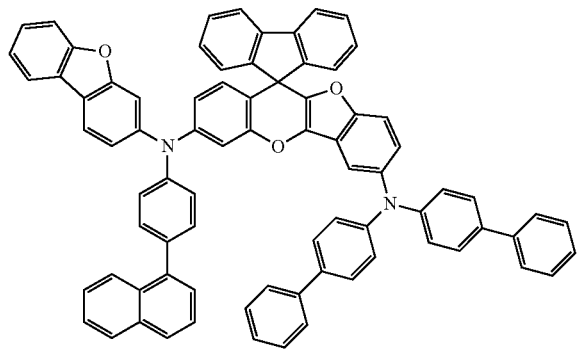
167
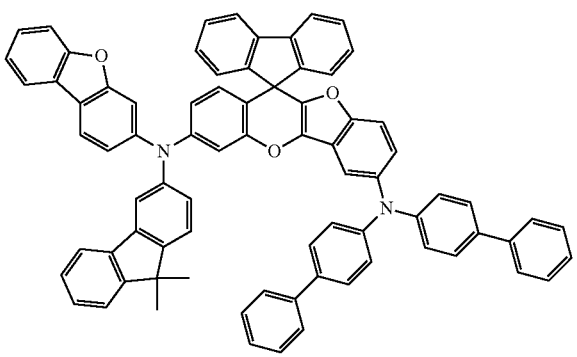
168
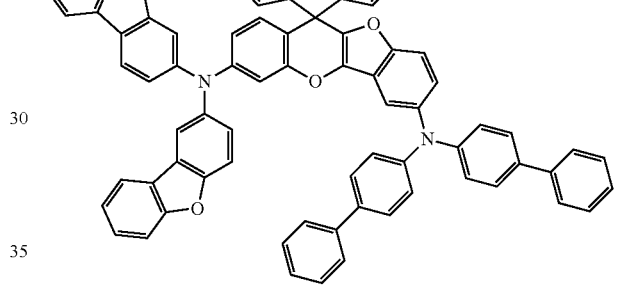
169
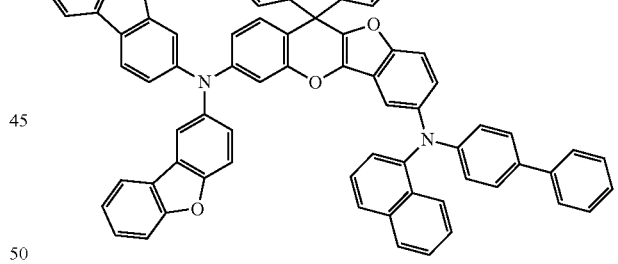
170
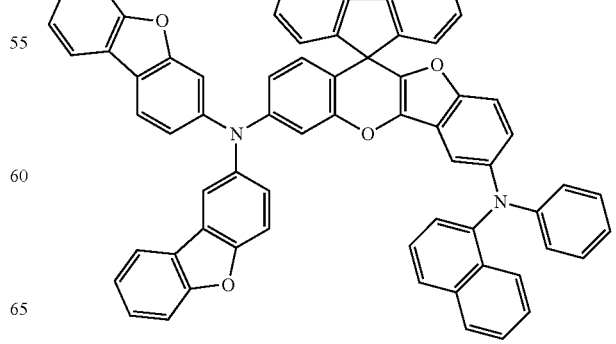

171 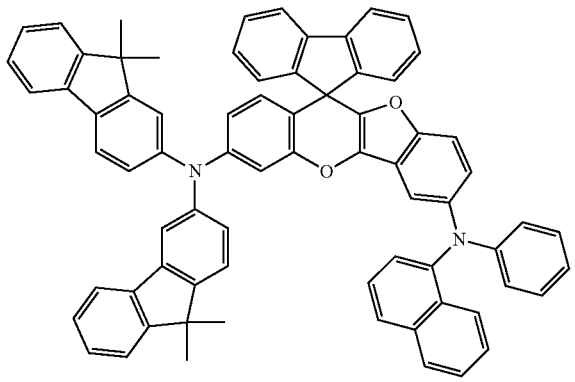

172 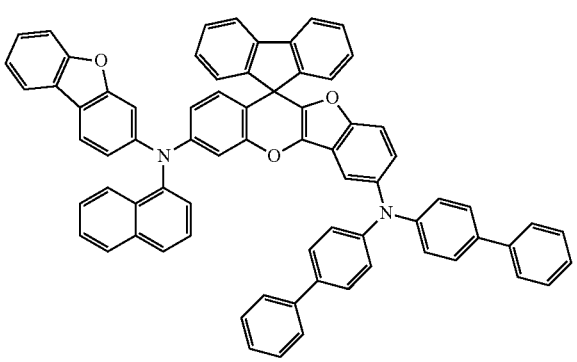

173 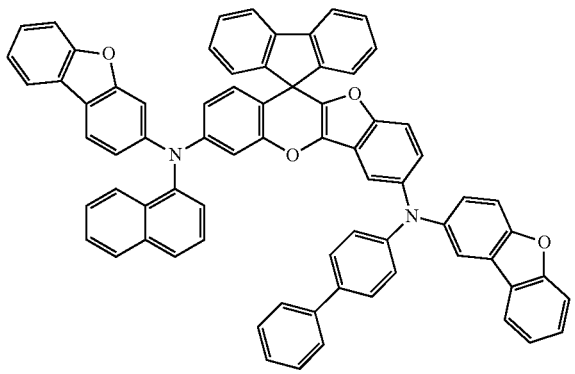

174 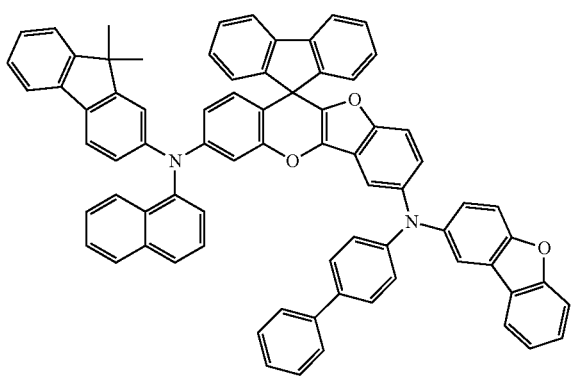

175 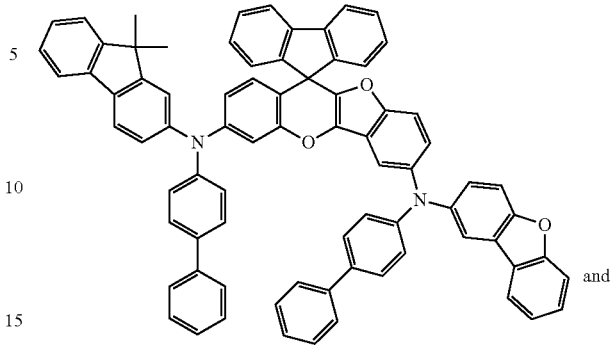

and

176 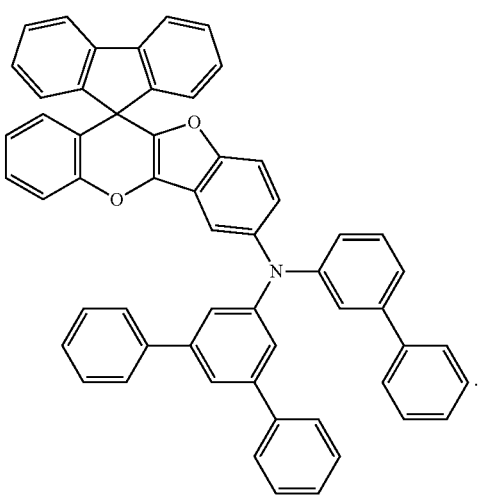

.

4. An organic light-emission device comprising:
an anode,
a cathode, and
at least one organic material layer therebetween, wherein the organic material layer comprises a compound of claim 3.

5. The organic light-emission device of claim 4, wherein the organic material layer includes at least one of a hole transport layer, an auxiliary hole transport layer and an electron blocking layer, wherein the at least one of the hole transport layer, the auxiliary hole transport layer and the electron blocking layer comprises the compound represented by Chemical Formula 1.

6. The organic light-emission device of claim 4, wherein the organic material layer comprises a blue light-emission layer comprising the compound represented by Chemical Formula 1 as a blue light-emission material.

7. The organic light-emission device of claim 4, wherein the organic material layer includes at least one of an electron transport layer and a hole blocking layer, wherein the at least one of the electron transport layer and the hole blocking layer comprises the compound represented by Chemical Formula 1.

8. The organic light-emission device of claim 7, wherein the electron transport layer comprises the compound represented by Chemical Formula 1.

9. The organic light-emission device of claim 7, wherein the hole blocking layer comprises the compound represented by Chemical Formula 1.

10. The organic light-emission device of claim 4, wherein the organic material layer comprises a blue light-emission layer, wherein the blue light-emission layer comprises the compound represented by Chemical Formula 1 as a phosphorescent host material.

11. An organic light-emission device comprising:
an anode,
a cathode, and
at least one organic material layer therebetween, wherein the organic material layer comprises a compound of claim 1.

12. The organic light-emission device of claim 11, wherein the organic material layer includes at least one of a hole transport layer, an auxiliary hole transport layer and an electron blocking layer, wherein the at least one of the hole transport layer, the auxiliary hole transport layer and the electron blocking layer comprises the compound represented by Chemical Formula 1.

13. The organic light-emission device of claim 12, wherein the hole transport layer comprises the compound represented by Chemical Formula 1.

14. The organic light-emission device of claim 12, wherein the auxiliary hole transport layer comprises the compound represented by Chemical Formula 1.

15. The organic light-emission device of claim 12, wherein the electron blocking layer comprises the compound represented by Chemical Formula 1.

16. The organic light-emission device of claim 11, wherein the organic material layer comprises a blue light-emission layer comprising the compound represented by Chemical Formula 1 as a blue light-emission material.

17. The organic light-emission device of claim 11, wherein the organic material layer includes at least one of an electron transport layer and a hole blocking layer, wherein the at least one of the electron transport layer and the hole blocking layer comprises the compound represented by Chemical Formula 1.

18. The organic light-emission device of claim 17, wherein the electron transport layer comprises the compound represented by Chemical Formula 1.

19. The organic light-emission device of claim 17, wherein the hole blocking layer comprises the compound represented by Chemical Formula 1.

20. The organic light-emission device of claim 11, wherein the organic material layer comprises a blue light-emission layer, wherein the blue light-emission layer comprises the compound represented by Chemical Formula 1 as a phosphorescent host material.

* * * * *